United States Patent
Hersel et al.

(10) Patent No.: US 9,238,686 B2
(45) Date of Patent: *Jan. 19, 2016

(54) POLYMERIC PRODRUG WITH SELF-IMMOLATIVE LINKER

(71) Applicant: Ascendis Pharma GmbH, Heidelberg (DE)

(72) Inventors: Ulrich Hersel, Heidelberg (DE); Harald Rau, Heidelberg (DE); Robert Schnepf, Dossenheim (DE); Dirk Vetter, Heidelberg (DE); Thomas Wegge, Heidelberg (DE)

(73) Assignee: Ascendis Pharma GmbH, Heidelberg (DE)

( * ) Notice: Subject to any disclaimer, the term of this patent is extended or adjusted under 35 U.S.C. 154(b) by 332 days.

This patent is subject to a terminal disclaimer.

(21) Appl. No.: 13/759,440

(22) Filed: Feb. 5, 2013

(65) Prior Publication Data

US 2013/0150281 A1 Jun. 13, 2013

Related U.S. Application Data

(63) Continuation of application No. 10/594,097, filed as application No. PCT/EP2005/003061 on Mar. 22, 2005, now Pat. No. 8,377,917.

(30) Foreign Application Priority Data

| Mar. 23, 2004 | (EP) | 04075892 |
| Jul. 5, 2004 | (GB) | 0415043.9 |
| Aug. 13, 2004 | (EP) | 04019293 |

(51) Int. Cl.
C07K 14/61 (2006.01)
A61K 47/48 (2006.01)
(Continued)

(52) U.S. Cl.
CPC ............ *C07K 14/62* (2013.01); *A61K 47/4823* (2013.01); *A61K 47/48176* (2013.01); *A61K 47/48215* (2013.01); *A61K 47/48284* (2013.01); *A61K 47/48784* (2013.01); *C07C 69/96* (2013.01); *C07D 207/46* (2013.01); *C07D 401/12* (2013.01); *C07K 14/00* (2013.01); *C07K 14/61* (2013.01)

(58) Field of Classification Search
None
See application file for complete search history.

(56) References Cited

U.S. PATENT DOCUMENTS

| 5,510,121 A | 4/1996 | Rhee et al. |
| 6,624,142 B2 | 9/2003 | Zhao et al. |

(Continued)

FOREIGN PATENT DOCUMENTS

| EP | 1 525 890 | 4/2005 |
| WO | WO-99/30727 | 6/1999 |

(Continued)

OTHER PUBLICATIONS

Bhatt et al., "Synthesis and in Vivo Antitumor Activity of Poly(L-glutamic acid) Conjugates of 20(S)-Camptothecin," *J. Med. Chem.*, (2003), pp. 190-193, vol. 46.

(Continued)

*Primary Examiner* — Nissa Westerberg
(74) *Attorney, Agent, or Firm* — Novak Druce Connolly Bove + Quigg LLP

(57) ABSTRACT

A cascade carrier linked prodrug is described comprising a biologically active moiety and a masking group having at least one nucleophile and being distinct from the carrier.

28 Claims, 7 Drawing Sheets

(51) Int. Cl.
*C07K 14/62* (2006.01)
*C07C 69/96* (2006.01)
*C07D 207/46* (2006.01)
*C07D 401/12* (2006.01)
*C07K 14/00* (2006.01)

(56) References Cited

U.S. PATENT DOCUMENTS

| 6,720,306 B2 | 4/2004 | Greenwald et al. |
| 2004/0038892 A1 | 2/2004 | Finn et al. |
| 2004/0254197 A1 | 12/2004 | Tasaka et al. |

FOREIGN PATENT DOCUMENTS

| WO | WO-99/33483 | 7/1999 |
| WO | WO-02/083180 | 10/2002 |
| WO | WO-02/089789 | 11/2002 |
| WO | WO-03/026577 | 4/2003 |
| WO | WO-03/057716 | 7/2003 |
| WO | WO-2004/019993 | 3/2004 |
| WO | WO-2004/043493 | 5/2004 |
| WO | WO-2005/034909 | 4/2005 |
| WO | WO-2005/082023 | 9/2005 |

OTHER PUBLICATIONS

Caliceti et al., "Pharmacokinetic and biodistribution properties of poly(ethylene glycol)-protein conjugates," *Advanced Drug Delivery Reviews*, (2003), pp. 1261-1277, vol. 55.
Cavallaro et al., "Polymeric Prodrug for Release of an Antitumoral Agent by Specific Enzymes," *Bioconjugate Chem.*, (2001), pp. 143-151, vol. 12.
Cheng et al., "Synthesis of Linear, β-Cyclodextrin-Based Polymers and Their Camptothecin Conjugates," *Bioconjugate Chem.*, (2003), pp. 1007-1017, vol. 14.
Duncan et al., "Polymer-drug conjugates, PDEPT and PELT; basic principles for design and transfer from the laboratory to clinic," *Journal of Controlled Release*, (2001), pp. 135-146, vol. 74.
Duncan, "The Dawning Era of Polymer Therapeutics," *Nature Reviews*, (May 2003), pp. 347-360, vol. 2.
Greenwald et al., "Drug Delivery Systems Employing 1,4- or 1,6-Elimination: Poly(ydroxyl e glycol) Prodrugs of Amine-Containing Compounds," *J. Med. Chem.*, (1999), pp. 3657-3667.
Luo et al., "A Hyaluronic Acid-Taxol Antitumor Bioconjugate Targeted to Cancer Cells," *Biomacromolecules*, (2000), pp. 208-218, vol. 1.
Matsumura et al., "A New Concept for Macromolecular Therapeutics in Cancer Chemotherapy: Mechanism of Tumoritropic Accumulatin of Proteins and the Antitumor Agent Smancs," *Cancer Research*, (Dec. 1986), pp. 6387-6392, vol. 46.
Na et al., "Monitoring of peptide acylation inside degrading PLGA microspheres by capillary electrophoresis and MALDI-TOF mass spectrometry," *Journal of Controlled Release*, (2003), pp. 291-299, vol. 92.
Peleg-Schulman et al., "Reversible PEGylation: A Novel Technology to Release Native Interferon α2 over a Prolonged Time Period," *J. Med. Chem.*, (2004), pp. 4897-4904, vol. 47.
Satchi-Fainaro et al., "PDEPT: Polymer-Directed Enzyme Prodrug Therapy. 2. HPMA Copolymer-β-lactamase and HPMA Copolymer-C-Dox as a Model Combination", *Bioconjugate Chem.*, (2003), pp. 797-804, vol. 14.

Testa et al., "Metabolic Hydrolysis and Prodrug Design," *Hydrolysis in Drug and Prodrug Metabolism*, (2003), pp. 4-5.
Testa et al., "The Hydrolysis of Carboxylic Acid Ester Prodrugs," *Hydrolysis in Drug and Prodrug Metabolism*, (2003), pp. 420-534, Chapter 8.
Wiwattanapatapee et al.,"Dendrimers conjugates for colonic delivery of 5-aminosalicyclic acid," *Journal of Controlled Release*, (2003), pp. 1-9, vol. 88.
Amir et al., "Self-Immolative Dendrimers," *Angew. Chem. Int. Ed.*, (2003), pp. 4494-4499, vol. 42.
Boas et al., "Dendrimers in drug research," *Chem. Soc. Rev.*, (2004), pp. 43-63, vol. 33.
De Groot et al., "Elongated Multiple Electronic Cascade and Cyclization Spacer Systems in Activatible Anticancer Prodrugs for Enhanced Drug Release," *J. Org. Chem.*, (2001), pp. 8815-8830, vol. 66.
Esfand et al., "Poly(amidoamine) (PAMAM) dendrimers: from biomimicry to drug delivery and biomedical applications," *DDT*, (Apr. 2001), pp. 427-436, vol. 6, No. 8.
Garman et al., "The preparation and properties of novel reversible polymer-protein conjugates," *FEBS Letters*, (Nov. 1987), pp. 361-365, vol. 223, No, 2.
Grayson et al., "Convergent Dendrons and Dendrimers: from Synthesis to Applications," *Chem. Rev.*, (2001), pp. 3819-3867, vol. 101.
Greene et al., "Protective Groups in Organic Synthesis," *John Wiley & Sons*, (1999), Third Edition.
Greenwald et al., "A New Aliphatic Amino Prodrug System for the Delivery of Small Molecules and Proteins Utilizing Novel PEG Derivatives," *J. Med. Chem.*, (2004), pp. 726-734, vol. 47.
Greenwald et al., "Drug Delivery Systems Based on Trimethyl Lock Lactonization: Poly(ethylene glycol) Prodrugs of Amino-Containing Compounds," *J. Med. Chem.*, (2000), pp. 475-487, vol. 43.
Hennink et al., "Novel crosslinking methods to design hydrogels," *Advanced Drug Delivery Reviews*, (2002), pp. 13-36, vol. 54.
Lee et al., "Drug Delivery Systems Employing 1,6-Elimination: Releasable Poly(ethylene glycol) Conjugates of Proteins," *Bioconjugate Chem.*, (2001), pp. 163-169, vol. 12.
Lee et al., "Targeted Enzyme-Responsive Drug Carriers: Studies on the Delivery of a Combination of Drugs," *Angew. Chem.*, (2004), pp. 1707-1710, vol. 116.
Peppas of al., "Hydrogels in pharmaceutical formulations," *European Journal of Pharmaceutics and Biopharmaceutics*, (2000), pp. 27-46, vol. 50.
Polonelli, et al., "Infect Immun.", vol. 71, No. 11, (2003), p. 6205-6212.
Sauerbrei et al., "An Enzyme-Labile Linker Group for Organic Syntheses on Solid Supports," *Angew. Chem. Int. Ed.*, (1998), pp. 1143-1146, vol. 37, No. 8.
Shabat et al., "Chemical Adaptor Systems," *Chem. Eur. J.*, (2004), pp. 2626-2634, vol. 10.
Veronese, "Biomaterial", vol. 22, (2001), p. 405-417.
Antczak et al., "A New Acivicin Prodrug Designed for Tumor-Targeted Delivery," *Bioorganic & Medicinal Chemistry*, (2001), pp. 2843-2848, vol. 9.
Drobnik, "The activation of ydroxyl groups of carriers with 4-nitrophenyl and N-hydroxysuccinimidyl chloroformates," *Biotechnology and Bioengineering*, 1982, vol. 24, pp. 487-493.
International Search Report for PCT/EP2005/003061. Mailing date Mar. 26, 2006.
Japanese Office Action and English Translation issued in related Japanese Patent Application No. 2007-504348 on Jun. 14, 2011.

POLYMERIC PRODRUG WITH SELF-IMMOLATIVE LINKER

RELATED APPLICATIONS

This application is a continuation application of U.S. Pat. application Ser. No. 10/594,097, filed May 6, 2008, which is a national stage application (under 35 U.S.C. §371) of PCT/EP2005/003061, filed Mar. 22, 2005, which claims benefit under 35 U.S.C. §119 to European Patent Application No. 04075892.2, filed on Mar. 23, 2004, British Patent Application No. 0415043.9, filed on Jul. 5, 2004, and European Patent Application No. 4019293.2, filed on Aug. 13, 2004.

FIELD

The present invention is directed to polymeric prodrugs having temporary linkages to amino groups of biologically active entities such as peptides, proteins, natural products or synthetic chemical compounds.

BACKGROUND

Typically, polymers are either used in a non-covalent fashion, with the drug compound physicochemically formulated into a solvent-polymer mixture, or by permanent covalent attachment of a polymer reagent to one of the drug's functional groups.

Non-covalent drug encapsulation has been applied to depot formulations for long-acting release profiles. Typically, drug is mixed with polymer material and processed in sash fashion, that the drug becomes distributed throughout the bulk polymer material. Such polymer-protein aggregates may be shaped as microparticles which are administered as an injectable suspension or they are formulated as gels which are administered in a single bolus injection. Drug release occurs when the polymer swells or degradation of the polymer allows for diffusion of the drug to the exterior. Such degradation processes may be autohydrolytic or enzyme-catalyzed. An example for a marketed drug based on bolus administration of a drug-polymer gel is Lupron Depot. An example for a marketed drug based on suspended microparticles is Nutropin Depot.

A disadvantage of the non-covalent approach is that in order to prevent uncontrolled, burst-type release of the drug, encapsulation has to be highly efficient by creating a sterically highly crowded environment. Restraining the diffusion of an unbound, water soluble drug molecule requires strong van der Waals contacts, frequently mediated through hydrophobic moieties. Many conformationally sensitive therapeutics such as proteins or peptides are rendered dysfunctional during the encapsulation process and/or during subsequent storage. In addition, such amino-containing drug compounds readily undergo side reactions with polymer degradation products (D. H. Lee et al., J. Cont. Rel., 2003, 92, 291-299). Furthermore, dependence of the release mechanism upon biodegradation may cause interpatient variability.

Alternatively, drugs may be conjugated to polymers through permanent covalent bonds. This approach is applied to various classes of molecules, from so-called small molecules, through natural products up to larger proteins.

Many small molecule medicinal agents, like alkaloids and anti-tumor agents, show low solubility in aqueous fluids. One way to solubilize these small molecule compounds is to conjugate them to hydrophilic polymers. A variety of water-soluble polymers, such as human serum albumin, dextran, lectins, poly(ethylene glycol) (PEG), poly(styrene-co-maleic anhydride), poly(N-hydroxypropylmethacrylamide), poly(divinyl ether-co-maleic anhydride), hyaluronic acid have been described for this purpose (R. Duncan, Nature Rev. Drug Disc., 2003, 2, 347-360).

A major challenge in cancer therapy is to selectively target cytotoxic agents to tumor cells. A promising method to accumulate small molecule anticancer agents in tumor tissue and decrease undesirable side effects of these agents is the attachment of the cytotoxin to a macromolecular carrier. The passive targeting of polymeric drug conjugates to tumors is based on the so-called enhanced permeability and retention effect (EPR) as described by Matsumura, Y. and Maeda, H., in Cancer Res., 1986, vol 6, pp 6387-6392. As a result, several polymer-drug conjugates have entered clinical trial as anticancer agents.

Covalent modification of biological molecules with poly(ethylene glycol) has been extensively studied since the late 1970s. So-called PEGylated proteins have shown improved therapeutic efficacy by increasing solubility, reducing immunogenicity, and increasing circulation half-live in vivo due to reduced renal clearance and proteolysis by enzymes (see, for example, Caliceti P., Veronese F. M., Adv. Drug Deliv. Rev. 2003, 55, 1261-1277).

However, many medicinal agents such as INFalfa2, saquinavir or somatostatin are inactive or show decreased biological activity when a polymer is covalently conjugated to the drag molecule (T. Peleg-Shulman et al., J. Med. Chem., 2004, 47, 4897-4904).

In order to avoid shortcomings imposed by either non-covalent polymer mixtures or permanent covalent attachment, it may be preferable to employ a prodrug approach for chemical conjugation of drug to polymer carrier. In such polymeric prodrugs, the biologically active moieties are typically linked to the polymeric carrier moiety by a temporary bond formed between the carrier moiety and a hydroxy, amino or carboxy group of the drug molecule (such as is shown in FIG. 1).

Prodrugs are therapeutic agents that are almost inactive per se but are predictably transformed into active metabolites (see B. Testa, J. M: Mayer in Hydrolysis in Drug and Prodrug Metabolism, Wiley-VCH 2003, page 4). The carrier prodrug approach may be applied in such a fashion that the medicinal agent is released in vivo from the polymer in order to regain its biological activity. The reduced biological activity of the prodrug as compared to the released drug is of advantage if a slow or controlled release of the drug is desired. In this case, a relatively large amount of prodrug may be administered without concomitant side effects and the risk of overdosing. Release of the drug occurs over time, thereby reducing the necessity of repeated and frequent administration of the chug.

Prodrug activation may occur by enzymatic or non-enzymatic cleavage of the temporary bond between the carrier and the drug molecule, or a sequential combination of both, i.e. an enzymatic step followed by a non-enzymatic rearrangement. In an enzyme-free in vitro environment such as an aqueous buffer solution, a temporary bond such as an ester or amide may undergo hydrolysis, but the corresponding rate of hydrolysis may be much too slow and not therapeutically useful. In an in vivo environment, esterases or amidases are typically present and may cause significant catalytic acceleration of the kinetics of hydrolysis from twofold up to several orders of magnitude (see, for example, R. B. Greenwald et al. J. Med. Chem., 1999, 42 (18), 3857-3867).

Definitions Based on IUPAC
(as given under http://www.chem.qmul.ac.uk/iupac/medchem/ (accessed on 8 Mar. 2004)

Prodrug

A prodrug is any compound that undergoes biotransformation before exhibiting its pharmacological effects. Prodrugs can thus be viewed as drugs containing specialized non-toxic protective groups used in a transient manner to alter or to eliminate undesirable properties in the parent molecule.

Carrier-linked Prodrug (Carrier Prodrug)

A carrier-linked prodrug is a prodrug that contains a temporary linkage of a given active substance with a transient carrier group that produces improved physicochemical or pharmacokinetic properties and that can be easily removed in vivo, usually by a hydrolytic cleavage. This is shown graphically in FIG. 1.

Cascade Prodrug

A cascade prodrug is a carrier prodrug for which the cleavage of the carrier group becomes effective only after unmasking an activating group.

Polymeric Cascade Prodrug

A polymeric cascade prodrug is a carrier prodrug that contains a temporary linkage of a given active substance with a transient polymeric carrier group for which the cleavage of the carrier becomes effective only after unmasking an activating group.

Bioprecursor Prodrug

A bioprecursor prodrug is a prodrug that does not imply the linkage to a carrier group, but results from a molecular modification of the active principle itself. This modification generates a new compound, able to be transformed metabolically or so chemically, the resulting compound being the active principle.

Biotransformation

Biotransformation is the chemical conversion of substances by living organisms or enzyme preparations.

Prodrugs fall in two classes, bioprecursors and carrier-linked prodrugs. Bioprecursors do not contain a carrier group and are activated by the metabolic creation of a functional group. In carrier-linked prodrugs the active substance is linked to a carrier moiety by a temporary linkage. This invention is concerned with polymeric carrier-linked or macromolecular prodrugs, where the carrier itself is a macromolecule such as a carrier protein or polysaccharide or polyethylene glycol. Specifically, the invention relates to polymeric carrier-linked prodrugs for which this cleavage between polymer and drug proceeds in two steps according to a cascade mechanism.

Cleavage of a carrier prodrug generates a molecular entity (drug) of increased bioactivity and at least one side product, the carrier. This side product may be biologically inert (for instance PEG) or may have targeting properties (for instance antibodies). After cleavage, the bioactive entity will reveal at least one previously conjugated and thereby protected functional group, and the presence of this group typically contributes to the drug's bioactivity.

In order to implement a prodrug strategy, at least one certain functional group in the drug molecule is employed for attachment of the carrier polymer. Preferred functional groups are hydroxyl or amino groups. Consequently, both the attachment chemistry and hydrolysis conditions vary greatly between these two functionalities.

In a simple one-step mechanism, the prodrug's temporary linkage is characterized by an intrinsic lability or enzyme dependence. The susceptibility of this linkage to hydrolysis in an aqueous environment with our without enzyme catalysis controls the cleavage kinetics between polymeric carrier and drug. Numerous macromolecular prodrugs are described in the literature where the temporary linkage is a labile ester bond. In theses cases, the functional group provided by the bioactive entity is either a hydroxyl group or a carboxylic acid (e.g. Y. Luo, M R Ziebell, G D Prestwich, "A Hyaluronic Acid-Taxol Antitumor Bioconjugate Targeted to Cancer Cells", Biomacromolecules 2000, 1, 208-215, Cheng et al. Synthesis of Linear, beta-Cyclodextrin Based Polymers and Their Camptothecin Conjugates, Bioconjugate Chem. 2003, 14, 1007-1017, R. Bhatt et al, Synthesis and in Vivo Antitumor Activity of Poly(L-glutamic acid) Conjugates of 20(S)-Camptothecin, J. Med. Chem. 2003, 46, 190-193; R. B. Greenwald, A. Pendri, C. D. Conover, H. Zhao, Y. H. Choe, A. Martinez, K. Shum, S. Guan, J. Med. Chem., 1999, 42, 3657-3667; B. Testa, J. M: Mayer in Hydrolysis in Drug and Prodrug Metabolism, Wiley-VCH, 2003, Chapter 8).

Especially for therapeutic biomacromolecules but also for certain small molecule drugs, it may be desirable to link the macromolecular carrier to amino groups of the bioactive entity (i.e. N-terminus or lysine amino groups of proteins). This will be the case if masking the drug's bioactivity requires conjugation of a certain amino group of the bioactive entity, for instance an amino group located in an active center or a region or epitope involved in receptor binding. Also, during preparation of the prodrug, amino groups may be more chemoselectively addressed and serve as a better handle for conjugating carrier and drug because of their greater nucleophilicity as compared to hydroxylic or phenolic groups. This is particularly true for proteins which may contain a great variety of different reactive functionalities, where non-selective conjugation reactions lead to undesired product mixtures which require extensive characterization or purification and may decrease reaction yield and therapeutic efficiency of the product.

Amide bonds as well as aliphatic carbamates are much more stable towards hydrolysis than ester bonds, and the rate of cleavage would be too slow for therapeutic utility in a carrier-linked prodrug. Therefore it is advantageous to add structural chemical components such as neighbouring groups in order to exert control over the cleavability of the prodrug amide bond. Such additional cleavage-controlling chemical structures that are not provided by the carrier entity nor by the drug are called linker. Prodrug linkers can have a strong effect on the rate of hydrolysis of a given temporary bond. Variation of the chemical nature of these linkers allows to engineer the linker properties to a great extent.

For instance, prodrug linkers may be designed for enzyme-selectivity. Prerequisite for enzymatic dependence is that the linker structure displays a structural motif that is recognized as a substrate by a corresponding endogenous enzyme (FIG. 2).

Enzyme-catalyzed acceleration of prodrug cleavage is a desirable feature for organ or cellular targeting applications. Targeted release of the bioactive entity is effected, if an enzyme, that selectively cleaves the linkage, is specifically present in the organ or cell-type chosen for treatment.

A typical property of an enzyme-dependent temporary linkage is its stability with respect to hydrolysis. The temporary linkage itself will not undergo autohydrolysis at a rate that would release drug to such an extent that a therapeutic effect could be induced in a normal dosing regime. It is only in the presence of the enzyme, that the attack of the enzyme on the linkage causes a significant acceleration of cleavage and concomitant an enhancement of free drug concentration.

Several examples have been published for the prodrug activation of amine-containing biologically active moieties by specific enzymes for targeted release. In these cases, cleavage occurs in a one-step process which is catalyzed by the enzyme. G. Cavallaro et al., Bioconjugate Chem. 2001, 12, 143-151 describe the enzymatic release of an antitumoral agent by the protease plasmin. Cytarabin is coupled via the tripeptide sequence D-Val-Leu-Lys to the polymer alpha; beta-poly(N-hydroxyethyl)-DL-aspartamide (PHEA). Enzymatic release of cytarabin is effected by the protease plasmin which concentration is relatively high in various kinds of tumor mass.

Further examples for antitumoral polymeric prodrugs activated by specific enzymes like beta lactamase (R. Satchi-Fainaro et al., Bioconjugate, Chem. 2003, 14, 797-804) and cysteine proteases like cathepsin B (R. Duncan et al. J. Contr. Release 2001, 74, 135-146) have been described. Wiwattanapatapee et al. (2003) outline a dendrimer prodrug for colonic delivery of 5-aminosalicylic acid. The drug molecule is conjugated by an azo bond to "generation 3" PAMAM dendrimer. 5-aminosalicylic acid is released in the colon by a bacterial enzyme called azo reductase (W. R. Wiwattanapatapee, L. Loralim, K. Saramunee, 3. Controlled Release, 2003, 88: 1-9).

A. J. Garman et al. (A. J. Garman, S. B. Kalindjan, FEBS Lett. 1987, 223 (2), 361-365 1987) use PEG5000-maleic anhydride for the reversible modification of amino groups in tissue-type plasminogen activator and urokinase. Regeneration of functional enzyme from PEG-uPA conjugate upon incubation at pH 7.4 buffer by cleavage of the maleamic acid linkage follows first order kinetics with a half-life of 6.1 h. The prodrug cleavage was not investigated in the presence of enzymes, and it can be expected—as explained above—that proteases present in the in vivo environment will significantly contribute to the cleavage of the temporary amide linkage. A further disadvantage of this linkage is the lack of stability of the conjugate at lower pH values. This limits the applicability of the linker to active agents which are stable at basic pH values, as purification of the active agent polymer conjugate has to be performed under basic conditions to prevent premature prodrug cleavage.

Cascade mechanisms have proven particularly useful in the controlled release of drugs containing amino-group functionalities because linker cleavage characteristics can be optimized with greater flexibility than in simple one-step prodrugs.

Cascade cleavage is enabled by linker compounds that are composed of a structural combination of a masking group and an activating group. The masking group is attached to the activating group by means of a first temporary linkage such as an ester or a carbamate. The activating group is attached to an amino-group of the drug molecule through a second temporary linkage, for instance a carbamate. The stability, or susceptibility to hydrolysis of the second temporary linkage is dependent on the presence or absence of the masking group. In the presence of the masking group, the second temporary linkage is highly stable and unlikely to release drug with therapeutically useful kinetics. In the absence of the masking group, this linkage becomes highly labile, causing rapid cleavage and drug release.

Cleavage of the first temporary linkage is the rate-limiting step in the cascade mechanism. This first step may induce a molecular rearrangement of the activating group such as a 1,6-elimination. The rearrangement renders the second temporary linkage so much more labile that its cleavage is induced, Ideally, the cleavage rate of the first temporary linkage is identical to the desired release rate for the drug molecule in a given therapeutic scenario. Furthermore, it is desirable that cleavage of the second temporary linkage is instantaneous after its lability has been induced by cleavage of the first temporary bond.

A variety of examples exist for cascade carrier prodrugs where the masking group functionality is performed by the carrier polymer itself as shown diagrammatically in FIG. 3. In the systems discussed below, the masking group is not only part of the carrier but has also been engineered for enzyme-dependence (FIG. 4). Only in the presence of a corresponding enzyme is the rate of cleavage of the first temporary linkage sufficiently accelerated for therapeutic use.

R. B. Greenwald, A. Pendri, C. D. Conover, H. Zhao, Y. H. Choe, A. Martinez, K. Sham, S. Guan, J. Med. Chem., 1999, 42, 3657-3667 & PCT Patent Application WO-A-99/30727 describe a methodology for synthesizing poly(ethylene glycol) prodrugs of amino-containing small molecule compounds based on 1,4- or 1,6-benzyl elimination. In this approach, poly(ethylene glycol) as the polymeric carrier is attached to the benzyl group by means of a first temporary linkage such as an ester, carbonate, carbamate, or amide bond. The benzyl group serves as the activating group, and the PEG polymer also has the function of the masking group in this cascade cleavage mechanism. The amino group of the drug molecule is linked via a second temporary linkage, containing a carbamate group, to the benzyl moiety. The release of PEG from the drug molecule is initiated by enzymatic cleavage of the first temporary linkage followed by a rapid 1,4- or 1,6-benzyl elimination, initiating cleavage of the second temporary linkage.

The same linker system is also used for releasable poly(ethylene glycol) conjugates of proteins (S. Lee, R. B, Greenwald at al. Bioconj. Chem. 2001, 12 (2), 163-169). Lysozyme is used as model protein because it loses its activity when PEGylation takes place on the epsilon-amino group of lysine residues, Various amounts of PEG linker were conjugated to the protein. Regeneration of native protein from the PEG conjugates occurs by enzymatic cleavage in rat plasma or in non-physiological high pH buffer.

Greenwald et al. published in 2000 a poly(ethylene glycol) drug delivery system of amino-containing prodrugs based on trimethyl lock lactonization Greenwald et al. J. Med. Chem. 2000, 43(3), 457-487; PCT Patent Application No. WO-A-02/089789). In this prodrug system, substituted o-hydroxyphenyl-dimethylpropionic acid is linked to PEG by an ester, carbonate, or carbamate group as a first temporary linkage and to amino groups of drug molecules by means of an amide bond as second temporary linkage. The rate-determining step in drug release is the enzymatic cleavage of the first linkage. This step is followed by fast amide cleavage by lactonization, liberating a potentially toxic aromatic lactone side product.

Similar prodrug systems were described by F. M. H. DeGroot et al. (WO02083180 and WO04043493A1) and D. Shabat et al. (WO04019993A1). WO02083180 discloses a prodrug system with elongated and multiple linkers based on 1,(4+2n) The masking moieties in these examples were specifically designed for enzymatic cleavage. This approach was extended to dendritic prodrug system where one enzymatic activating event triggered the release of more than one drag molecule (WO04043493A1). WO04019993A1 discloses a similar prodrug system based on a self-immolative dendrimer releasing many drug moieties upon a single enzymatic activating event. These systems are characterized by the absence of a polymeric carrier. Instead, oligomerization of prodrug linker components provides for a high molecular weight of the prodrug, and prodrug cleavage generates linker residues and free drug, but no polymeric entity is released.

The disadvantage in the abovementioned prodrug systems described by Greenwald, DeGroot and Shabat is the release of potentially toxic aromatic small molecule side products like quinone methides after cleavage of the temporary linkage. The potentially toxic entities are released in a 1:1 stoichiometry with the drug and can assume high in vivo concentrations. This risk factor is even greater if self-immolative dendritic structures based on oligomers of the activating group are employed and more aromatic side products than drug molecules are released.

More recently; R. B. Greenwald et al. (Greenwald et al. J. Med. Chem. 2004, 47, 726-734) described a PEG prodrug system based on bis-(N-2-hydroxyethyl)glycin amide (bicin amide) linker. In this system two PEG molecules are linked to a bicin molecule coupled to an amino group of the drug molecule. The first two steps in prodrug activation is the enzymatic cleavage of both PEG molecules. Different linkages between PEG and bicin are described resulting in different prodrug activation kinetics. The main disadvantage of this system is the slow hydrolysis rate of bicin amide conjugated to the drug molecule (t1/2=3 h in phosphate buffer) which results in the release of a bicin-modified prodrug intermediate that may show different pharmacokinetic and pharmacodynamic properties as compared to the parent drug molecule.

Cascade prodrugs with masking groups that are part of the carrier polymer are limited in the control of drug release kinetics. As masking group cleavage is the rate-limiting step in the cascade mechanism, its molecular structure governs the kinetics. If the carrier polymer is identical to the masking group, the structural flexibility is restricted to the polymers' features. Alternatively, if the polymer requires structural modification in order to match the requirements for controlled cleavage, synthesis of corresponding structures may become more difficult. Also, the incorporation of masking group features into a polymer may change its safety profile.

Therefore is it preferred to structurally separate the masking group and the carrier. This may be achieved by employing a permanent bond between polymer carrier and activating group. This stable bond does not participate in the cascade cleavage mechanism. If the carrier is not serving as a masking group and the activating group is coupled to the carrier by means of a stable bond, release of potentially toxic side products such as the activating group is avoided. The stable attachment of activating group and polymer also suppresses the release of drug-linker intermediates with undefined pharmacology.

Systems have been developed for targeted delivery of therapeutic agents by rendering the masking group enzyme-dependent. Only in the presence of a corresponding enzyme is the rate of cleavage of the first temporary linkage connecting the masking group with the activating group sufficiently accelerated for therapeutic use.

Antczak et al. (Bioorg Med Chem 9 (2001) 2843-48) describe a reagent which forms the basis for a macromolecular cascade prodrug system for amine-containing drug molecules. In this approach an antibody serves as carrier, a stable bond connects the antibody to an activating moiety, carrying an enzymatically cleavable masking group. Upon enzymatic removal of the ester-Linked masking group, a second temporary bond cleaves and releases the drug compound, as shown in FIG. 6.

D. Shabat et al. (Chem. Eur. J. 2004, 10, 2626-2634) describe a polymeric prodrug system based on a mandelic acid activating moiety. In this system the masking group is linked to the activating moiety by a carbamate bond. The activating moiety is conjugated permanently to a polyacrylamide polymer via an amide bond. After enzymatic activation of the masking group by a catalytic antibody, the masking group is cleaved by cyclization and the drug is released. The activating moiety is still connected to the polyacrylamide polymer after drug release.

M.-R. Lee et al. describe (Angew. Chem., 2004, 116, 1707-1710) a similar prodrug system based on mandelic acid activating moiety and an enzymatically cleavable ester-linked masking group.

In all of these described prodrug-polymer systems the masking group is specifically designed to be substrate to an enzyme, and masking group cleavage will almost entirely depend upon enzymatic catalysis with the disadvantages of interpatient variability, injection site variability and poor in vitro-in vivo correlation.

A major drawback of predominantly enzymatic cleavage is interpatient variability. Enzyme levels may differ significantly between individuals resulting in biological variation of prodrug activation by enzymatic cleavage. Enzyme levels may also vary depending on the site of administration, for instance it is known that in the case of subcutaneous injection, certain areas of the body yield more predictable therapeutic effects than others. To reduce this unpredictable effect, non-enzymatic cleavage or intramolecular catalysis is of particular interest (see, for example, B. Testa, J. M: Mayer in Hydrolysis in Drug and Prodrug Metabolism, Wiley-VCH, 2003, page 5).

Furthermore, it is difficult to establish an in vivo-in vitro correlation of the pharmacokinetic properties for such enzyme-dependent carrier-linked prodrugs. In the absence of a sound in vivo-in intro correlation the optimization a release profile becomes a cumbersome task.

Also, the need for enzyme selectivity imposes a severe limitation on the structural features that can be used in the prodrug linker. This restriction greatly hinders the development of a sound structure-activity relationship and consequently the optimization of linker cleavage kinetics.

For these reasons, there is a need to provide novel linker and/or carrier technologies for forming polymeric prodrugs of amine containing active agents in order to overcome the limitations of the described polymeric prodrugs.

A BRIEF DESCRIPTION OF THE FIGURES

FIG. 1 shows a carrier-linked prodrug.

FIG. 2 shows an enzyme-dependent carrier-linked prodrug.

FIG. 3 shows a cascade prodrug where the masking group is part of the carrier.

FIG. 4 shows an enzyme-dependent cascade prodrug where the masking group is part of the carrier.

FIG. 5 shows a self-cleaving cascade prodrug where the masking group is separate from the carrier.

FIG. 6. shows an enzyme-dependent cascade prodrug where the masking group is separate from the carrier.

FIG. 7. shows a cascade prodrug where the carrier is sterically protecting the masking group.

FIG. 8 shows cleavage of the masking group by intramolecular cyclisation.

FIG. 9 shows a possible side reaction of polymeric prodrug activation.

FIG. 10 shows general synthesis methods.

FIG. 11 shows mass spectra of prodrug released insulin molecules.

DETAILED DESCRIPTION OF THE INVENTION

The present invention addresses the disadvantages described above. The invention provides for polymeric cascade prodrugs characterized by a masking group containing a nucleophile and being distinct from the carrier.

The nucleophile is in a suitable distance to a first temporary linkage with an aromatic activating group capable of undergoing a 1,(4+0.2p) elimination reaction (with p=0, 1, 2, 3, 4, . . . ) after cleavage of the first temporary linkage. The invention is further characterized by the activating group being connected to the amino group of a drug molecule through a second temporary bond which is cleaved as a consequence of the 1,(4+2p) elimination. An additional structural feature is the attachment of a polymeric carrier to the activating group by means of a permanent bond.

The masking groups according to the present invention contain at least one nucleophile Nu. This nucleophile, which can be for example a primary, secondary or tertiary amino group can assist the cleavage of the masking group from the activating moiety by intramolecular catalysis or cyclization.

The invention provides for polymeric cascade prodrugs and corresponding polymeric cascade prodrug linker reagents of Formula Ia or Ib.

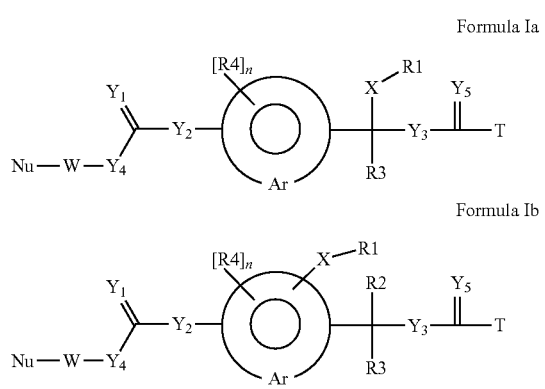

Formula Ia

Formula Ib wherein $Y_1$ to $Y_5$, R1 to R4, T, X, W, Nu and Ar are defined below:

Native drag release is effected by a two step mechanism. The first step is the rate-determining cleavage of the first temporary linkage between the masking group

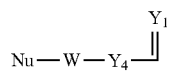

and the activating moiety

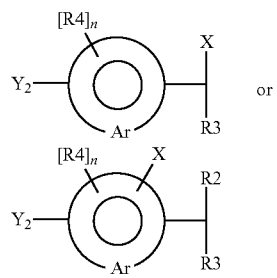

from the polymeric prodrug in vivo.

As described above, cleavage of the masking group may be mediated by an enzymatic or a non-enzymatic step, such as pH-dependent hydrolysis or intramolecular cyclization. In the preferred embodiment of the invention, cleavage is effected non-enzymatically by intramolecular cyclization or catalysis. The half-life of the cleavage kinetics in an aqueous buffer of pH 7.4 at 37° C. of the masking group according to the present invention is preferably between 1 hour and 6 months, more preferably between 1 day and 3 months, and most preferably between 1 day and 2 months.

The second and final step in release of the regenerated native drug is the fast, spontaneous and irreversible so-called 1,4- or 1, 6 or 1,(4+2p) (in which p=2, 3, 4 or higher) elimination of the

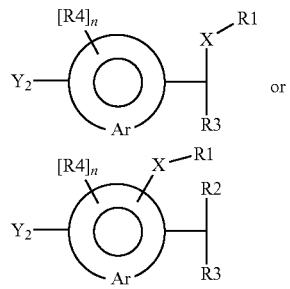

moiety of the remaining polymeric prodrug of formula Ia or formula Ib, respectively.

This mechanism of native drug release from a polymeric prodrug triggered by hydrolytic cleavage of the masking group followed by a 1,6-elimination step of the activating group is exemplified by a polymeric prodrug according to the present invention.

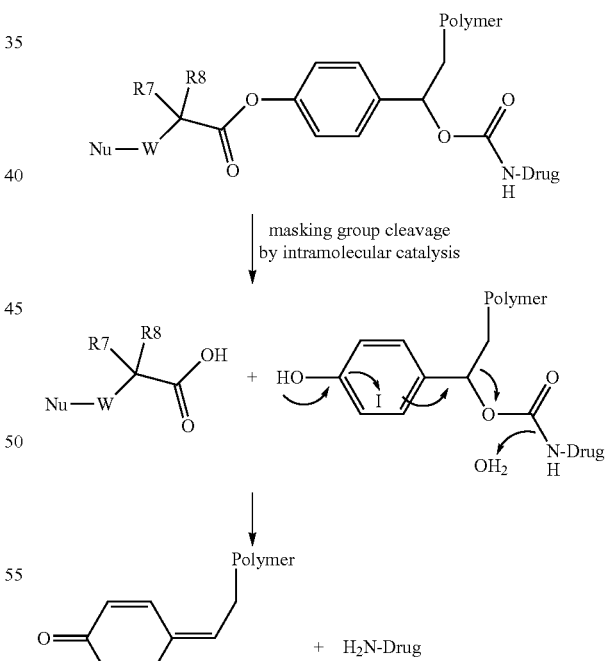

Definition of $Y_1$ to $Y_5$, R1 to R4, T, X, W, Nu and Ar in Formula Ia or Ib
T is D or A
In the case where the inventive structure is a polymeric cascade prodrug linker reagent, T is A, and A is a leaving group. Non-limiting examples of suitable leaving groups A include but are not limited to chloride, bromide, fluoride, nitrophenoxy, imidazolyl, N-hydroxysuccinimidyl, N-hydroxybenzotriazolyl, hydroxyazobenzotriazolyl, pentafluorphenoxy, N-hydroxysulfosuccinimidyl, or any other leaving group known by those skilled in the art.

In the case where the inventive structure is a polymeric cascade prodrug, T is D, and D is a residue of an amine-containing biologically active material including but not limited to small molecule bioactive agents or biopolymers like proteins, polypeptides and oligonucleotides (RNA, DNA), peptide nucleic acids (PNA), Note that in this description reference is often made to prodrugs. A true prodrug is found when T is the residue of the amine-containing biologically active material or moiety. If T is a leaving group A then the formula represents a polymeric cascade prodrug linker reagent. For simplicity these will be referred to prodrugs in this description. It will be understood from the context whether a true prodrug or a reagent as a predursor is meant.

Suitable organic small molecule bioactive moieties include, without limitation, moieties such as central nervous system-active agents, anti-infective, anti-neoplastic, antibacterial, anti-fungal, analgesic, contraceptive, anti-inflammatory, steroidal, vasodilating, vasoconstricting, and cardiovascular agents with at least one primary or secondary amino group. Non-exclusive examples of such compounds are daunorubicin, doxorubicin, idarubicin, mitoxantron, aminoglutethimide, amantadine, diaphenylsulfon, ethambutol, sulfadiazin, sulfamerazin, sulframethoxazol, sulfalen, clinafloxacin, moxifloxacin, ciprofioxaxin, enoxacin, norfloxacin, neomycin B, sprectinomycin, kanamycin A, meropenem, dopamin, dobutamin, lisinopril, serotonin, carbutamid, acivicin, etc.

Suitable proteins and polypeptides having at least one free amino group include but are not limited to ACTH, adenosine deaminase, agalsidase, albumin, alfa-1 antitrypsin (AAT), alfa-1 proteinase inhibitor (API), alteplase, anistreplase, ancrod serine protease, antibodies (monoclonal or polyclonal, and fragments or fusions), antithrombin III, antitrypsins, aprotinin, asparaginases, biphalin, bone-morphogenic proteins, calcitonin (salmon), collagenase, DNase, endorphins, enfuvirtide, enkephalins, erythropoietins, factor VIIa, factor VIII, factor VIIIa, factor IX, fibrinolysin, fusion proteins, follicle-stimulating hormones, granulocyte colony stimulating factor (G-CSF), galactosidase, glucagon, glucagon-like peptides like GLP-1, glucocerebrosidase, granulocyte macrophage colony stimulating factor (GM-CSF), phospholipase-activating protein (PLAP), gonadotropin chorionic (hCG), hemoglobins, hepatitis B vaccines, hirudin, hyaluronidases, idurnonidase, immune globulins, influenza vaccines, interleukins (1 alfa, 1 beta, 2, 3, 4, 6, 10, 11, 12), IL-1 receptor antagonist (rhIL-1ra), insulins, interferons (alfa 2a, alfa 2b, alfa 2c, beta 1a, beta 1b, gamma 1a, gamma 1b), keratinocyte growth factor (KGF), transforming growth factors, lactase, leuprolide, levothyroxine, luteinizing hormone, lyme vaccine, natriuretic peptide, pancrelipase, papain, parathyroid hormone, PDGF, pepsin, platelet activating factor acetylhydrolase (PAF-AH), prolactin, protein C, octreotide, secretin, sermorelin, superoxide, dismutase (SOD), somatropins (growth hormone), somatostatin, streptokinase, sucrase, tetanus toxin fragment, tilactase; thrombins, thymosin, thyroid stimulating hormone, thyrotropin, tumor necrosis factor (TNT), TNF receptor-IgG Fc, tissue plasminogen activator (tPA), TSH, urate oxidase, urokinase, vaccines, plant proteins such as lectins and ricins.

Also included herein is any synthetic polypeptide or any portion of a polypeptide with in vivo bioactivity. Furthermore, proteins prepared by recombinant DNA methodologies including mutant versions of aforementioned proteins, antibody fragments, single chain binding proteins, catalytic antibodies and fusion proteins are included.

Preferred proteins are antibodies, calcitonin, G-CSF, GM-CSF, erythropoietins, hemoglobins, interleukins, insulins, interferons, SOD, somatropin, TNF, TNF-receptor-IgG Fc, and GLP-1.

X is a spacer moiety such as R5-Y6.

$Y_1$, $Y_2$ can each be either O, S, or NR6, independently of each other.

$Y_3$, $Y_5$ can each be either O or S, independently of each other.

$Y_4$ is O, NR6, or —C(R7)(R8)-$Y_6$ is O, S, NR6, succinimide, maleimide, unsaturated carbon-carbon bonds or any heteratom containing a free electron pair, or is not present.

R2 and R3 are selected independently from hydrogen, substituted or non-substituted linear, branched or cyclical alkyl or heteroalkyl, aryls, substituted aryls, substituted or non-substituted heteroaryls, cyano, nitro, halogen, carboxy, carboxyalkyl, alkylcarbonyl, carboxamidoalkyl, etc.

The term "heteroalkyl" in the context of the present invention denotes (linear, cyclical or branched) alkyl chains where the alkyl chains contain or are substituted with at any position one or more heteroatoms, selected independently from O, S, N, P, Si, Cl, F, Br, I, etc, or groups, selected independently from carboxamide, carboxylic ester, phosphonate ester, phosphate ester, double or triple bonds, carbamate, urea, thiourea, thiocarbamate, oxime, cyano, carboxyl, carbonyl, etc.

Each R4 substitution on Ar may be the same or different and is selected independently from hydrogen, substituted or non-substituted linear, branched or cyclical alkyl or heteroalkyl, aryl, substituted aryl, substituted or non-substituted heteroaryl, substituted or non-substituted linear, branched, or cyclical alkoxy, substituted or non-substituted linear, branched, or cyclical heteroalkyloxy, aryloxy, heteroaryloxy, cyano, halogen, etc.

R4 is selected preferably from small substituents such as hydrogen, methyl, ethyl, ethoxy, methoxy, and other C1 to C6 linear, cyclical or branched alkyls and heteroalkyls.

n is zero or a positive integer.

R7 and R8 are selected independently from hydrogen, substituted or nom-substituted linear, branched or cyclical alkyl or heteroalkyl, aryls, substituted aryls, substituted or non-substituted heteroaryls, cyano, halogen, etc.

R5 is selected from substituted or non-substituted linear, branched or cyclical alkyl or heteroalkyl, aryls, substituted aryls, substituted or non-substituted heteroaryls, etc.

R6 is selected from hydrogen, substituted or non-substituted linear, branched or cyclical alkyl or heteroalkyl, aryls, substituted aryls, substituted or non-substituted heteroaryls, etc.

R1 is a polymer.

Non-limiting examples for suitable polymers are polyalkyloxy-based polymers like polypropylene glycol) or poly(ethylene glycol), dextran, chitosan, hyaluronic acid and derivatives, alginate, xylan, mannan, carrageenan, agarose, cellulose, starch, hydroxyethyl starch (HES) and other carbohydrate-based polymers, poly(vinyl alcohols), poly(oxazolines), poly(anhydrides), poly(ortho esters), poly(carbonates), poly(urethanes), poly(acrylic acids), poly (acrylamides) such as poly(hydroxypropylmethacrylamide) (HMPA), poly(acrylates), poly(methacrylates) like poly(hydroxyethylmethacrylate), poly(organophosphazenes), poly (siloxanes), poly(vinylpyrrolidone), poly(cyanoacrylates), poly(esters) such as poly(lactic acid) or poly(glycolic acids), poly(iminocarbonates), poly(amino acids) such as poly (glutamic acid), collagen, gelatin, copolymers, grafted copolymers, cross-linked polymers, hydrogels, and block copolymers from the above listed polymers.

Hydrogels may be defined as three-dimensional, hydrophilic or amphiphilic polymeric networks imbibing large quantities of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water which allows them to swell in aqueous media. (see.: N. A. Peppas, P. Bures, W, Leobandung, H. Ichikawa, Hydrogels in pharmaceutical formulations, Eur. J. Pharm. Biopharm. 2000, 50, 27-46). The chains of the network are connected in such a fashion that pores exist and that a substantial fraction of these pores are of dimensions of between 1 and 1000 nm. By selecting certain polymerization conditions, the hydrogel may be obtained in the form of an amorphous gel or as beaded resin. Such soft beads may have a diameter of between 1 and 1000 micrometer.

Hydrogels may be synthesized from the polymers and copolymers listed above and physically cross-linked or chemically cross-linked by radical, anionic or cationic polymerization, by chemical reactions like condensation or addition reactions as described in W. E, Hennink and C. F. van Nostrum, Adv. Drug. Del, Rev. 2002, 54, 13-36.

Further examples include branched and hyperbranched polymers. Examples for such polymers include dendrimers and other dense star polymers. (R. Esfand, Tomalia, Drug Discov Today, 2001, 6(8), 427-436; P. M. Heegaard, U. Boas, Chem. Soc. Rev. 2004 (33(1), 43-63; S. M. Grayson, J. M. Frechet, Chem. Rev. 2001, 101 (12), 3819-3868).

R1 can also be a biopolymer like a protein. Non-limiting examples of such polymers include albumin, antibodies, fibrin, casein, and other plasma proteins.

Each R1 polymer can carry one or more biologically active substances linked to the polymer by conjugation with a second prodrug linker as described herein or any other linker known to the person skilled in the art. The polymers may have further substituents and may be functionalized for attachment to the spacer moiety X. Non-limiting examples of such functional groups comprise carboxylic acid and activated derivatives, amino, maleimide, thiol, sulfonic acid and derivatives, carbonate and derivatives, carbamate and derivatives, hydroxyl aldehyde, ketone, hydrazine, isocyanate, isothiocyanate, phosphoric acid and derivatives, phosphoric acid and derivatives, haloacetyl, alkyl halides, acryloyl, arylating agents like aryl fluorides, hydroxylamine, disulfides like pyridyl disulfide, vinyl sulfone, vinyl ketone, diazoalkanes, diazoacetyl compounds, epoxide, oxirane, and aziridine.

Preferred functional groups for the R1 polymer include but are not limited to thiol, maleimide, amino, carboxylic acid and derivatives, carbonate and derivatives, carbamate and derivatives, aldehyde, and haloacetyl.

Especially preferred functional groups include thiol, maleimide, amino, carboxylic acid and derivatives, carbamate and derivatives, and carbonate and derivatives thereof.

Non-limiting examples for suitable bonds or groups formed between X and R1 include disulfide, S-succinimido, amide, amino, carboxylic ester, sulfonamide, carbamate, carbonate, ether, oxime, hydrazone, urea, thiourea, phosphate, phosphonate, etc.

Preferred bonds or groups formed between X and R1 comprise S-succinimido, amide, carbamate, and urea.

Preferably, the R1 polymers are well hydrated, degradable or excretable, nontoxic and non-immunogenic in mammals. Preferred R1 polymers include polyalkoxy-based polymers like polyethylene glycol and polyethylene glycol reagents as those described in Nektar Inc. 2003 catalog "Nektar Molecule Engineering—Polyethylene Glycol and Derivatives for Advanced PEGylation" and branched., hyperbranched, cross-linked polymers and hydrogels, and proteins like albumin.

W is selected from substituted or non-substituted linear, branched or cyclical alkyl, aryls, substituted aryls, substituted or non-substituted linear, branched or cyclical heteroalkyl, substituted or nonsubstituted heteroaryls, etc.

W is selected preferably from non-toxic substituted or non-substituted linear, branched or cyclical alkyls or heteroalkyls.

Preferred variations of

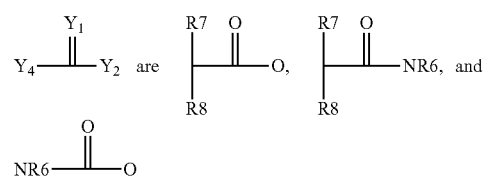

Especially preferred variations of

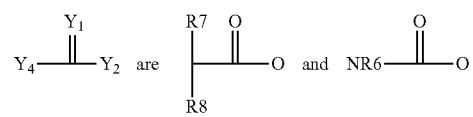

forming polymeric prodrugs of the following formulas:

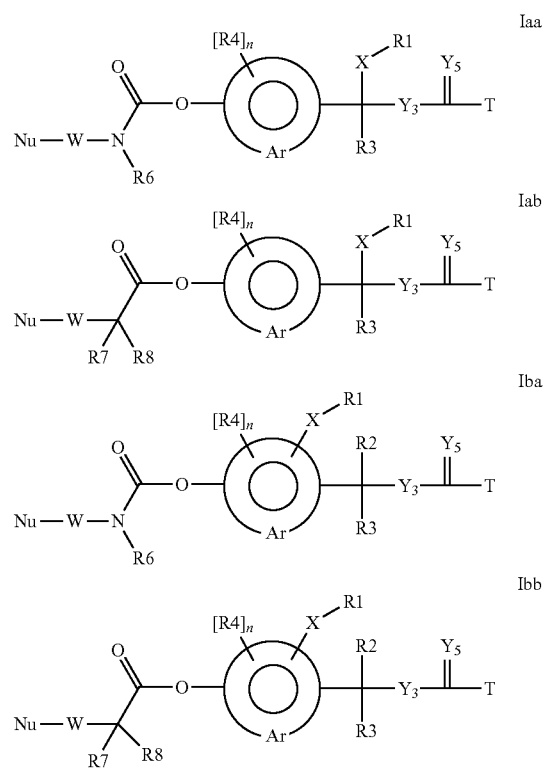

In formula Iaa and Iba R6 may also be Nu-W.
At least one Nu is present in Nu-W.

Nu is a nucleophile that can perform a nucleophilic attack at the carbonyl carbon of

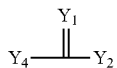

and thus catalyse the cleavage of the masking group by intramolecular catalysis or cyclization (FIG. 8). FIG. 8 shows an example according to formula Ia or Ib wherein the cleavage of the masking group is by intramolecular cyclization. In cases where Nu only catalyses the cleavage of the masking group by intramolecular catalysis, no cyclical product of the masking group is formed.

Preferred nucleophiles include primary, secondary and tertiary amino groups, thiol, carboxylic acid, hydroxylamine, hydrazine, and nitrogen containing heteroaryl. Especially preferred nucleophiles include primary, secondary and tertiary amino groups. In order to effectively catalyse the cleavage of the masking group, the spacing between the nucleophile Nu and $Y_2$ is preferably between three and fifteen atoms. More preferably, the spacing between Nu and $Y_2$ is between four and ten atoms. The at least one nucleophile Nu may be attached anywhere to W (e.g. at the terminus or in the middle of W) or may be part of W.

Preferred variations for the masking group

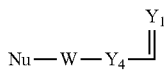

are selected independently from

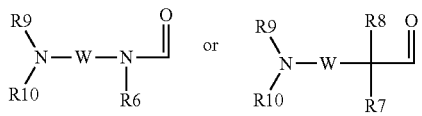

where

forms a primary, secondary or tertiary amine nucleophile Nu.

These preferred variations result in polymeric prodrugs according to the following formulas:

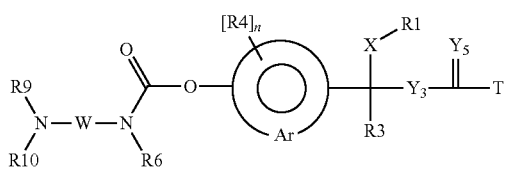

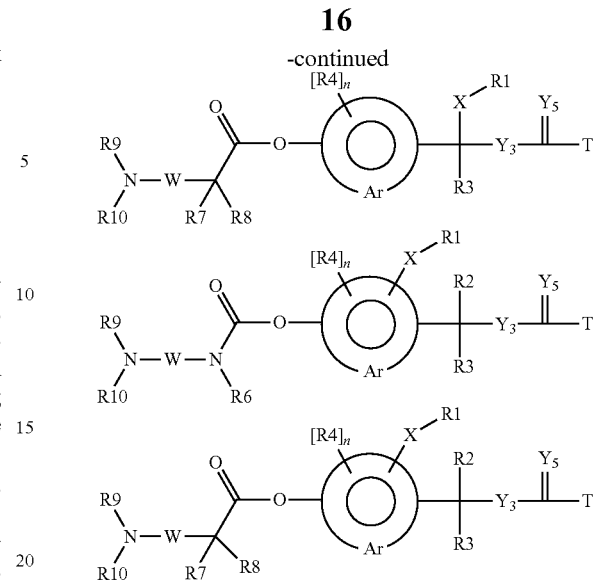

R9, R10 are selected independently from hydrogen, substituted or non-substituted alkyl or heteroalkyl, substituted or non-substituted aryl or heteroaryl.

Especially preferred variations for the masking group

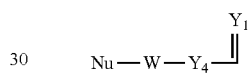

are selected from

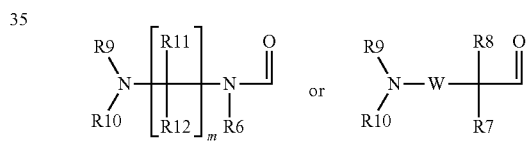

$m = 2 - 10$

Preferably, R9, R10, R11 and R12 are selected independently from hydrogen, substituted or non-substituted alkyl and R7 and/or R8 are not hydrogen.

R6 may also be

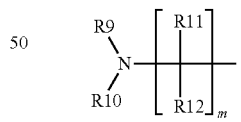

and is preferably not hydrogen.

Surprisingly it was found, that the masking group can modify irreversibly the amine containing biologically active moiety when the nucleophile Nu is absent in the masking group. As shown in the example section, during release of the bioactive moiety insulin from a polymeric prodrug with a pentanoyl masking group which is not part of the present invention (as it does not contain a nucleophile), approximately 30% of the insulin molecule was modified with the masking group by acyl transfer. The mechanism of an example of this modification where D contains an additional free amino group that serve as nucleophile for acyl transfer from the masking group is shown in FIG. 9.

Ar of formula Ia or Ib is a multi-substituted aromatic hydrocarbon or a multi-substituted aromatic heterocycle. To be aromatic, the number of pi electrons must satisfy the Rachel rule (4n+2) and the cycle has to be planar. A huge variety of compounds satisfy these criteria and thus are suitable as Ar in formula Ia or Ib. Non-limiting preferred aromatic moieties include:

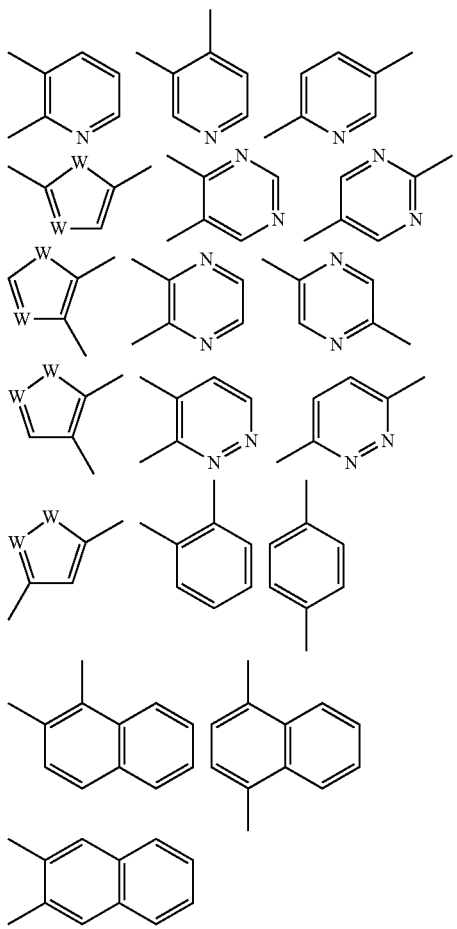

wherein W is O, N, or S, independent from each other.

$Y_2$ and

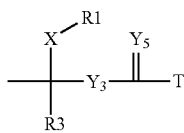

in formula Ia or $Y_2$ and

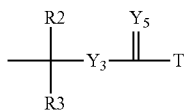

in formula Ib have to be arranged on the aromatic ring in such a fashion that a 1,4- or 1,6- or 1,(4+2p), with p=2, 3, 4 and higher, elimination can take place (see above). For example, in the case of a 6-membered ring, the substituents have to be arranged ortho or para.

Preferred moieties for Ar are mono- and dicyclic aromatic hydrocarbons or aromatic heterocycles.

Especially preferred moieties are monocycle five- or six-membered aromatic hydrocarbons or aromatic heterocycles.

General Synthesis Procedures of the Polymeric Prodrugs

Synthesis of representative examples of polymeric prodrugs according to the present invention is described in the Examples section.

Prodrugs of the present invention can be prepared in various different fashions. FIG. 10 shows general routes for the synthesis of the polymeric prodrugs of the present invention according to formula Ia.

In a first method, intermediate (III) is provided by acylating $Y_2$ of starting material (II) with the masking group

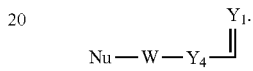

For this, X or Nu may have to be protected with a reversible protecting group $PG_1$. Suitable protecting groups are described in T W Greene, P. G. M. Wuts, Protective groups in organic synthesis, 1999, John Wiley & Sons, $3^{rd}$ ed. From intermediate (III) two alternative routes can be used to yield (Iaa). In a first route intermediate (III) is activated by an activating agent such as 4-nitrophenyl chloroformate or disuccinyl carbonate to yield (IV). The amine containing drug molecule is attached to (IV) to yield (V) by displacing the leaving group of the activated intermediate (IV). After deprotection of X such as by treating intermediate (V) with reagents like trifluoroacetic acid or DTT (where applicable) deprotected intermediate (V) is then reacted with polymer R1 to yield the polymeric prodrug (Iaa).

In a second route the polymer R1 is first attached to the intermediate (III) after deprotection of K (where applicable) to form intermediate (VI). After an activation step intermediate (VII) is fainted (VII) is reacted with the amine containing drug molecule to form the polymeric prodrug (Iac).

In a second method, intermediate (VIII) is provided by activating starting material (II) by an activating agent such as 4-nitrophenyl chloroformate. For this, $Y_2$ and/or X may have to be protected with a protecting group $PG_2$ and/or $PG_1$. Amine containing drug is reacted with intermediate (VIII) to form (IX). In a first route, $Y_2$ of (IX) is selectively deprotected and acylated to form intermediate (V) which is further processed to (Iaa) as described above. In a second route X is selectively deprotected and reacted with polymer R1 to form intermediate (X). $Y_2$ of (X) is then deprotected and acylated to form the polymeric prodrug (Iac).

In a third method starting material (II) is reacted with polymer R1 to form intermediate (XI). In one route, intermediate (XI) can be acylated to form intermediate (VI) which processed as described above to form polymeric prodrug (Iaa). In a second route, $Y_2$ is protected by the protecting group $PG_2$, activated and reacted with the amine containing drug molecule to faun (X). Intermediate (X) is then processed as described above to form the polymeric prodrug (Iac).

For all methods described, further functional groups such as $Y_3$ or nucleophiles present in Nu-W may have to be protected with suitable protecting groups.

Polymeric prodrugs according to formula Ib can be prepared by methods described above for prodrugs according to formula Ia using starting material IIb instead of II in FIG. 10.

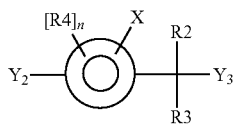

IIb

It is understood, that linker structures according to the outlined invention and carrying protecting groups or leaving groups as described and used in the synthesis of corresponding polymeric prodrugs are considered within the range of the invention.

Application of the Polymeric Prodrugs in Molecular Therapy

For polymeric cascade prodrugs it is desirable for the cleavage kinetics of the first temporary linkage to proceed under conditions present in the blood circulation of the human body (pH 7.4, 37° C.). Most importantly, cleavage of the first temporary linkage should be based on hydrolysis and exhibit none or only very limited dependence upon chemical or biochemical or physicochemical entities present in the human blood circulation such as enzymes, salts or binding proteins.

It was now surprisingly found that the rate of cleavage of the first temporary linkage connecting the masking group with the activating group as well as its dependence upon blood components can be controlled by neighbouring group effects mediated by nucleophilic functional groups (such as primary, secondary or tertiary amines) present in the masking group and positioned in a distance to the corresponding temporary bond. If the masking group is structured in this fashion, an intramolecular reaction with contribution of the nucleophile governs the kinetics of the linkage (FIG. 5 and FIG. 8).

Key advantage of the polymeric prodrugs of the present invention is their predominantly non-enzymatic cleavage: the half-life of the prodrug in suitably buffered human blood plasma of pH 7.4 (with aqueous buffer concentration <50%) is at least 50% of the half-life of the prodrug in enzyme-free buffer pH 7.4.

This feature allows for better predictability and control of release rates after administration to a living organism and reduces interpatient variability.

In contrast to the enzymatic dependency of masking group removal as described in abovementioned examples of Antzczak et al., Shabat et al. and Lee et al., a higher level of control over release rates can be achieved if the masking group has enzyme-independent, self-eliminating properties.

The masking groups according to the present invention contain at least one nucleophile Nu. Structural features of this masking group such as nucleophilicity of the amine group and ring-forming capacity may be systematically optimized in order to precisely adjust the rate of prodrug cleavage. Such intramolecular reactions resulting in unmasking and subsequent rearrangement are highly independent from enzymes due to the fact that intramolecular reactions are generally preferred over intermolecular reactions as shown diagrammatically in FIG. 8.

In another embodiment of the invention, independency of prodrug cleavage from enzyme levels is achieved by providing a prodrug containing a sterically demanding carrier croup as is shown in FIG. 7.

Such encapsulation or sterical protection by the sterically demanding carrier group may be conferred by a branched, hyperbranched, crosslinked or self-assembled structure of the carrier polymer. Such polymers tend to form a densely packed molecular volume, as exemplified for instance in dendrimers, dense star polymers or bead-shaped nano- and microparticles or amorphous gels. If the linkage of the polymer carrier to the drug is located in the interior of the polymer carrier, the linked drug will be efficiently encapsulated and protected from enzymatic attack. In this case, sterical hindrance by the polymer prevents enzymes from accessing and cleaving the temporary linkages.

In yet another embodiment, enzyme-independent prodrug cleavage is achieved by combining an intramolecular self-eliminating masking group with an encapsulating hyperbranched or crosslinked or self-assembled carrier.

A further advantage of the present invention is the release of an unmodified biologically active moiety, In cases where the biologically active moiety contains further reactive functional groups like amino groups of lysine residues in proteins, an unwanted side reaction between the masking group and the biologically active moiety can occur. The reactive functional-groups of the biologically active moiety may react with the masking group, forming a stable covalent bond and resulting in the release of a modified biologically active moiety. This potential side reaction is shown schematically in FIG. 9. The occurrence of such side reactions is shown in the examples section using polymeric prodrugs which are not part of the present invention with simple masking groups like a pentanoyl residue without a nucleophile Nu present in the masking group and as described by Antczak et al. or Lee et al. The side reaction in this linker system is suppressed using polymeric prodrugs according to the present invention with intramolecularly activated masking groups that contain nucleophiles Nu (see example section).

Enzyme-independent release control enables depot formulations without the need for encapsulation. Until now, many biocompatible materials like hydrogels with large pore sizes could not be used for depot formulations due to their lack of encapsulation properties. From such well-hydrated and mechanically soft biocompatible materials, biologically active moiety would be released too fast for most therapeutic applications. In combination with the prodrug linkers described in this invention, the carrier material may be optimized for its biocompatibility properties as the release is solely governed by the linker cleavage kinetics and does not require chemical or enzymatic degradation of the polymer carrier itself.

Release rates are governed by a substantially non-enzymatic chemical reaction which is in turn dependent on the molecular structure of the linker. Systematic or random modifications of the chemical structure, for instance by changing substituents in one or more positions, for instance a masking group in a cascade prodrug, allows for the generation of prodrug linkers with differing release rates. It is therefore possible to create a variety of prodrug linkers and select those fast or slow cleaving prodrug linkers according to the demands posed by a given medicinal or therapeutic application.

Another advantageous feature which is part of this invention is the attachment of the polymer carrier through a stable covalent bond to an activating moiety involved in a double or cascade prodrug release mechanism. As part of this invention, the activating moiety remains attached to the polymer carrier after drug release and therefore cannot diffuse into the environment. Permanent linkage of the polymer carrier to the activating group greatly reduces the any side-reactivity of the activating moiety and the probability of unwanted toxic effects. In other polymeric cascade prodrugs known in the art, the activating moiety is released in addition to the drug. Due to the molecular rearrangement mechanisms used in cascade prodrugs, the activating moiety is released in a highly reactive form and may cause direct damage to surrounding biomolecules, or potentially toxic derivatives of the activating moiety may be formed in vivo.

EXAMPLES

Materials

Figure 1:
FIG. 1 shows a carrier-linked prodrug.
Figure 2:
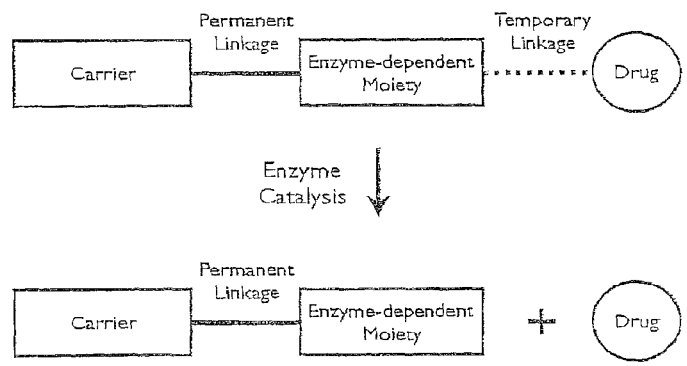
FIG. 2 shows an enzyme-dependent carrier-linked prodrug.
Figure 3:
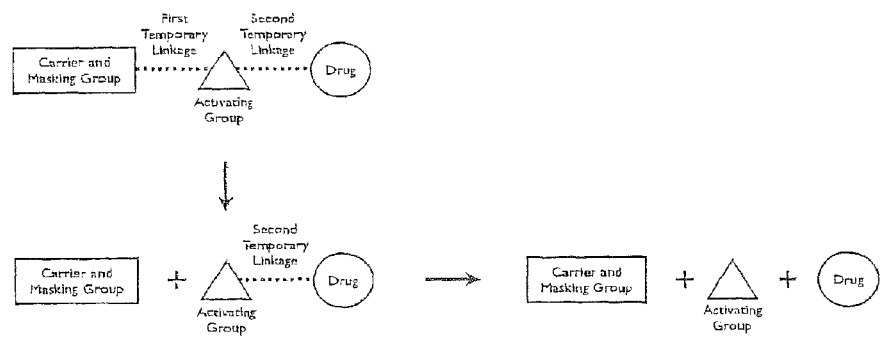
FIG. 3 shows a cascade prodrug where the masking group is part of the carrier.
Figure 4:
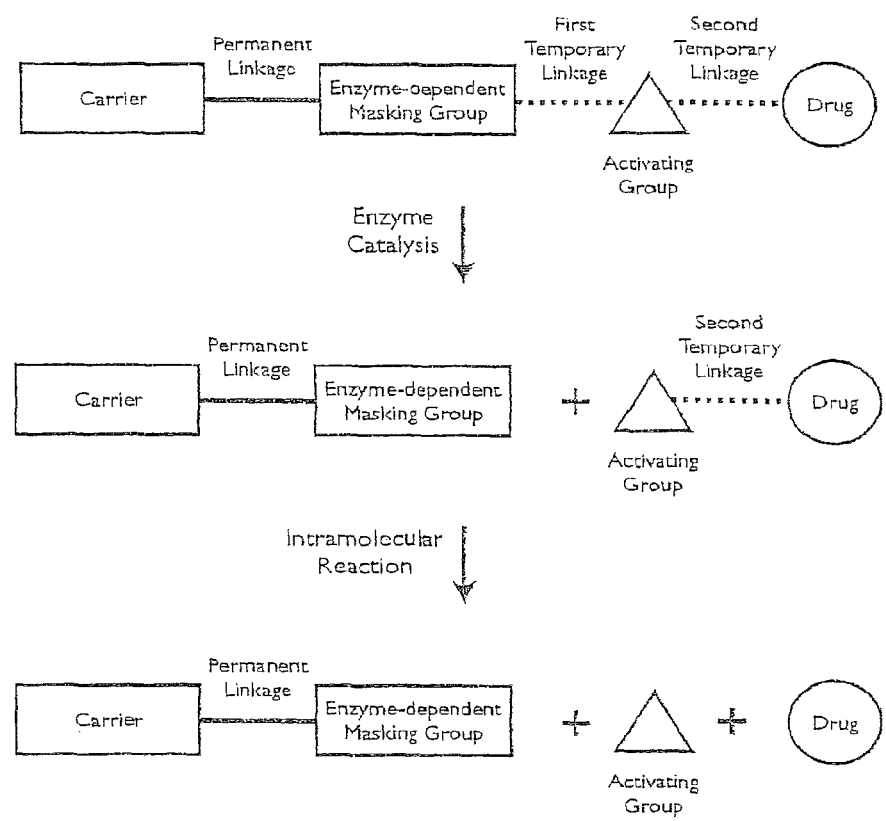
FIG. 4 shows an enzyme-dependent cascade prodrug where the masking group is part of the carrier.
Figure 5:
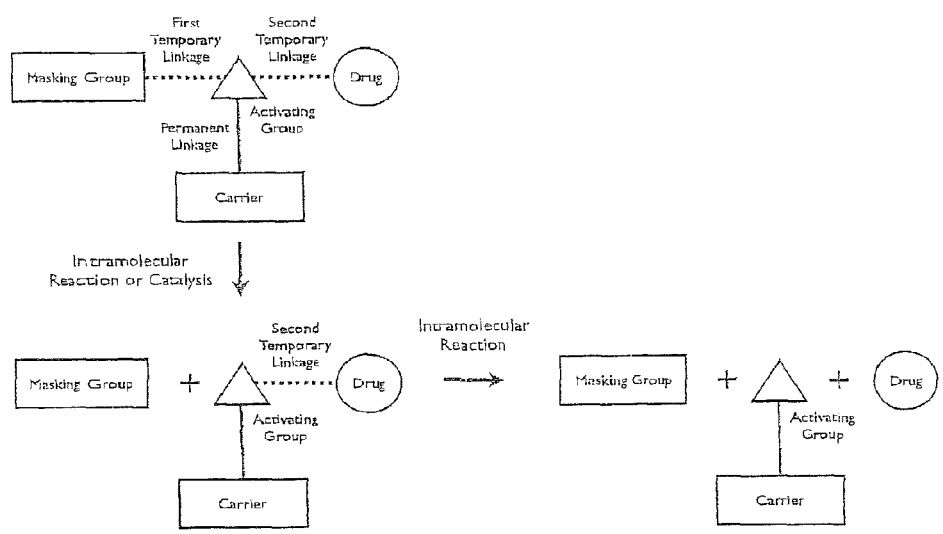
FIG. 5 shows a self-cleaving cascade prodrug where the masking group is separate from the carrier.
Figure 6:
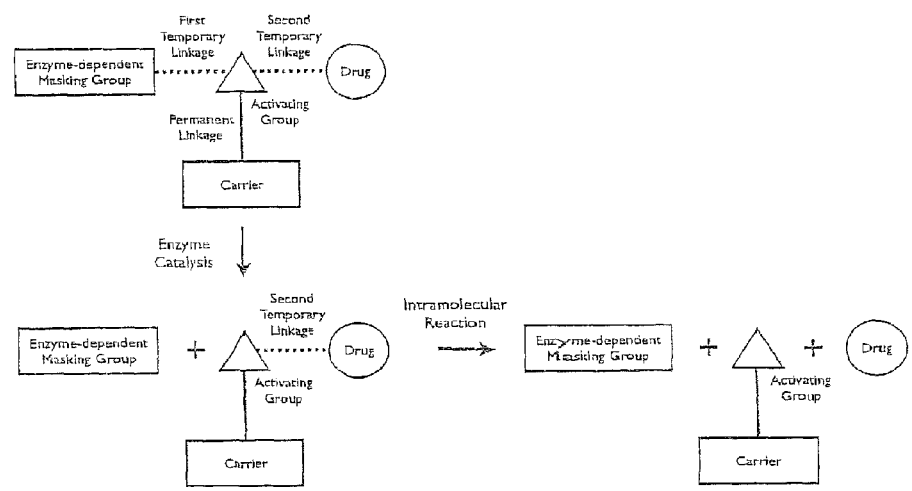
FIG. 6 shows an enzyme-dependent cascade prodrug where the masking group is separate from the carrier.
Figure 7:
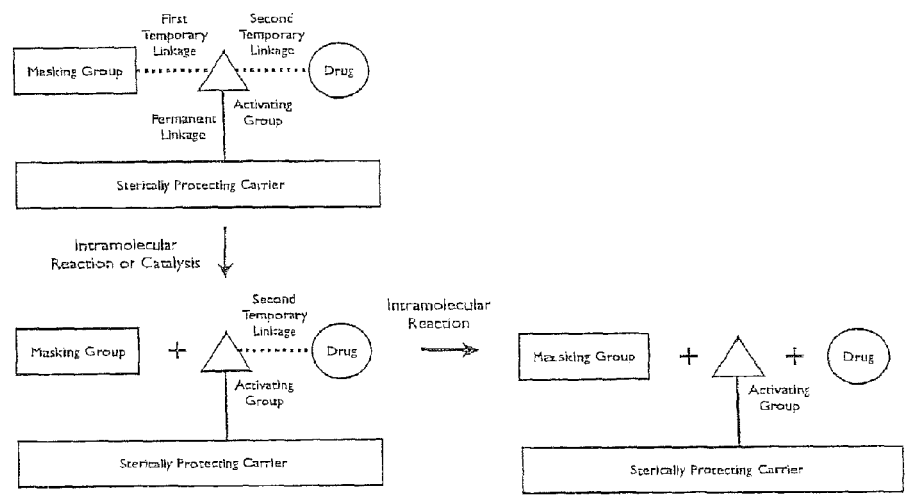
FIG. 7 shows a cascade prodrug where the carrier is sterically protecting the masking group.
Figure 8:
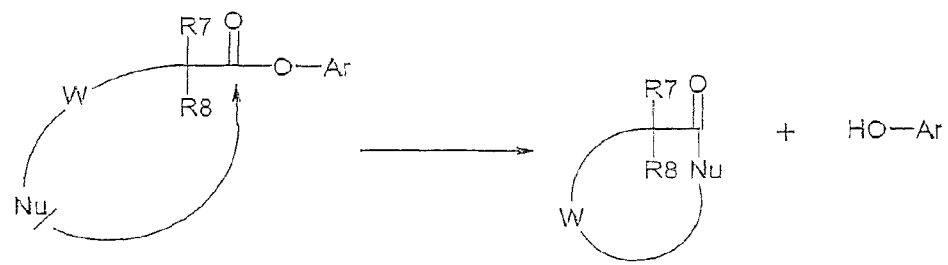
FIG. 8 shows cleavage of the masking group by intramolecular cyclisation.
Figure 9:
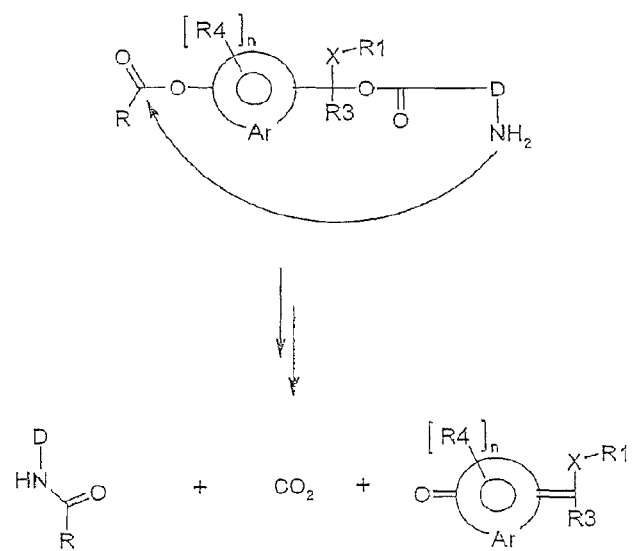
FIG. 9 shows a possible side reaction of polymeric prodrug activation.
Figure 10:
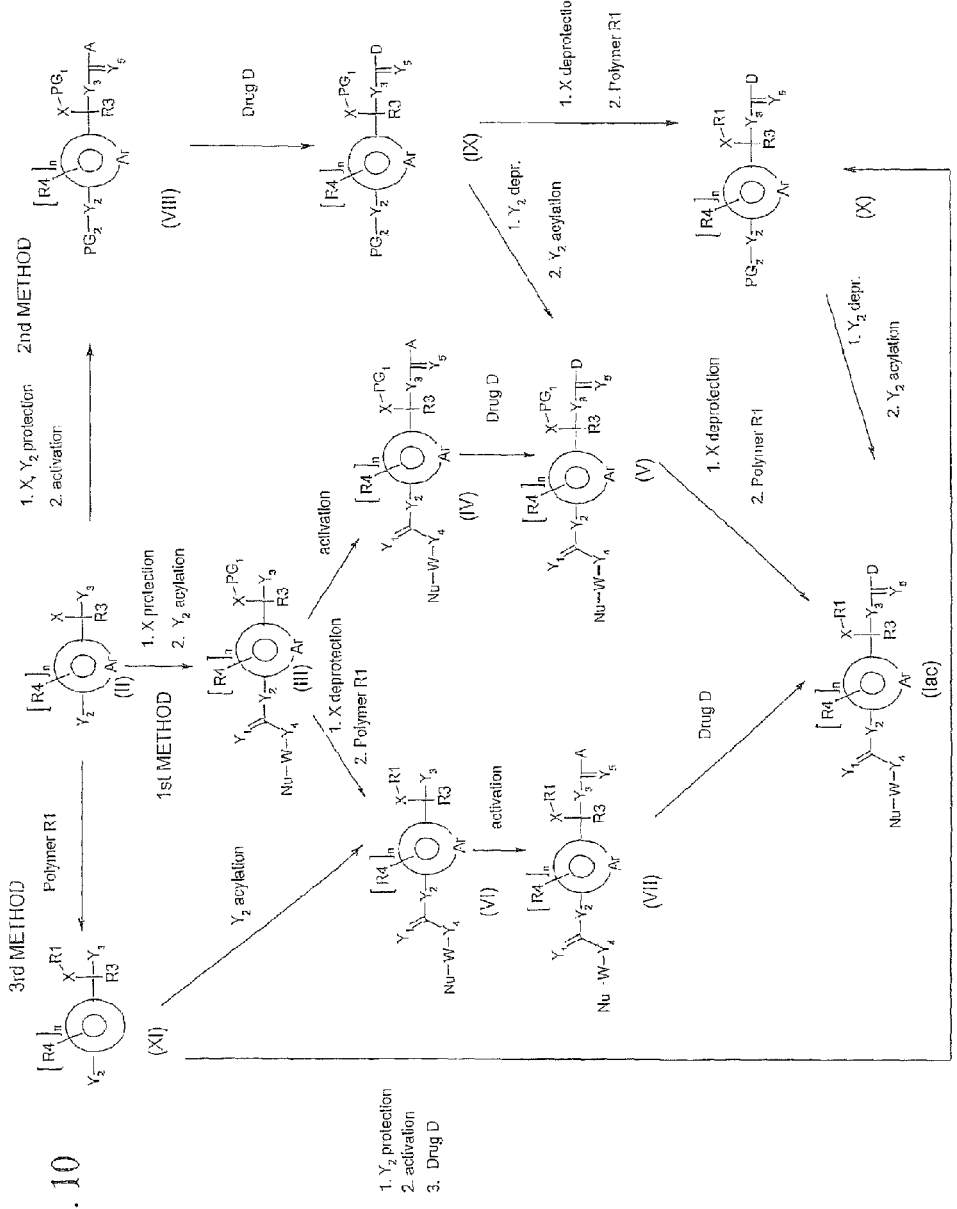
FIG. 10 shows general synthesis methods.

Fmoc-amino acids, resins and PyBOP were purchased from Novabiochem and are named according to the catalogue. Fmoc-Ado-OH was obtained from Neosystem. All additional chemicals were purchased from Sigma Aldrich. Recombinant human insulin was from ICN Biomedicals (USA). Maleimide-PEG5k was obtained from Nektar (USA). 5-(and -6)-carboxyfluorescein succinimidyl ester (mixed isomers) was obtained from Molecular Probes.

Solid Phase Synthesis Reaction Medium

Solid phase synthesis was performed on NovaSyn TG Sieber amide resin with a loading of 0.17 mmol/g or 2-chlorotrityl chloride resin with a loading of 1.4 mmol/g. Syringes equipped with polypropylene frits were used as reaction vessels.

Standard Coupling Cycle for Fmoc-protected Amino Acids

For fmoc protecting-group removal, the resin was repeatedly (three times, 4 min each) agitated with 2/2/96 (v/v/v) piperidine/DBU/DMF and repeatedly (six times) washed with DMF.

Coupling of fmoc-protected amino acids to free amino groups on resin was achieved by agitating the resin with 3 equivalents (eq) of fmoc-amino acid, 3 eq PyBOP and 6 eq DIEA in relation to free amino groups in DMF for 60 min. Finally, the resin was repeatedly (five times) washed with DMF.

Standard Cleavage Protocol for TentaGel Sieber Amide Resin

Upon completed synthesis, the resin was washed with DCM, dried in vacuo and treated repeatedly (five times) with 97/2/1 (v/v) DCM/TES/TFA. After evaporation, compounds were purified by preparative RP-HPLC (Waters 600).

Standard Cleavage Protocol for 2-chlorotrityl Chloride Resin

Upon completed synthesis, the resin was washed with DCM, dried in vacuo and treated two times for 30 minutes with 65/35 (v/v) HFIP/DCM. After combining the eluates the volatile components were evaporated.

Analysis

Mass spectrometry (MS) was performed on a Waters ZQ 4000 ESI instrument and spectra were, if necessary, interpreted by Waters software MaxEnt.

Size exclusion chromatography was performed using an Amersham Bioscience AEKTAbasic system equipped with a Superdex 200 column (Amersham Bioscience). NMR spectra were recorded on a Broker AC300.

Overview—Synthesis of Polymeric Prodrugs According to Formula Ia with Ester-Linked Masking Groups

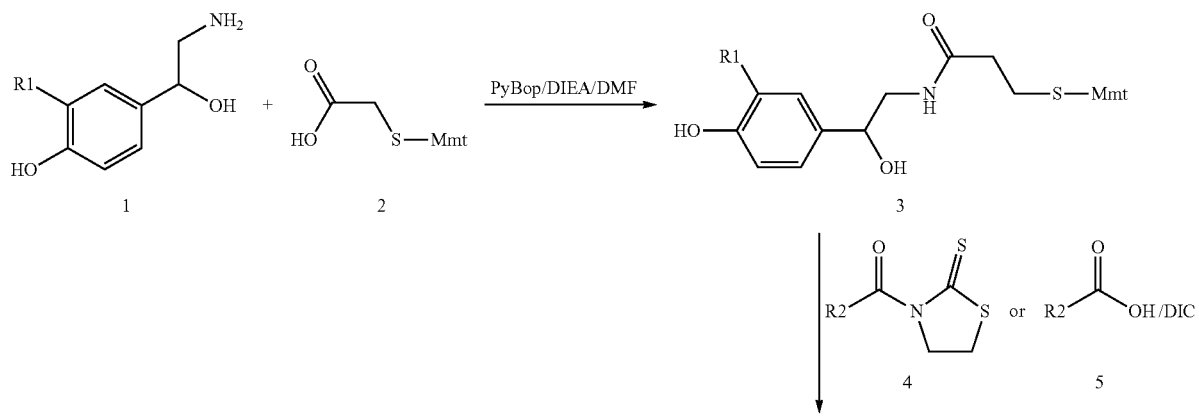

-continued
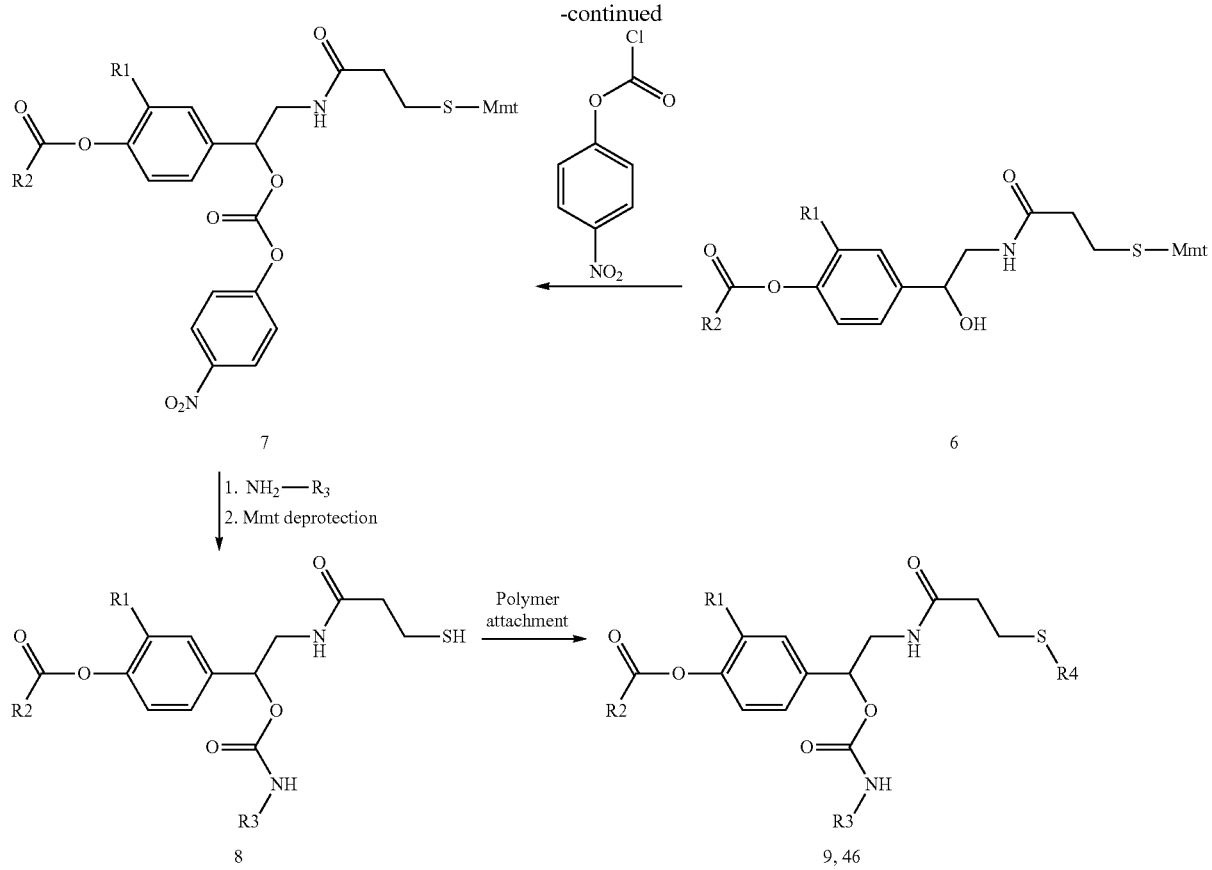
Synthesis of Polymeric Prodrugs According to Formula Ia with Carbamate-linked Masking Groups
a)
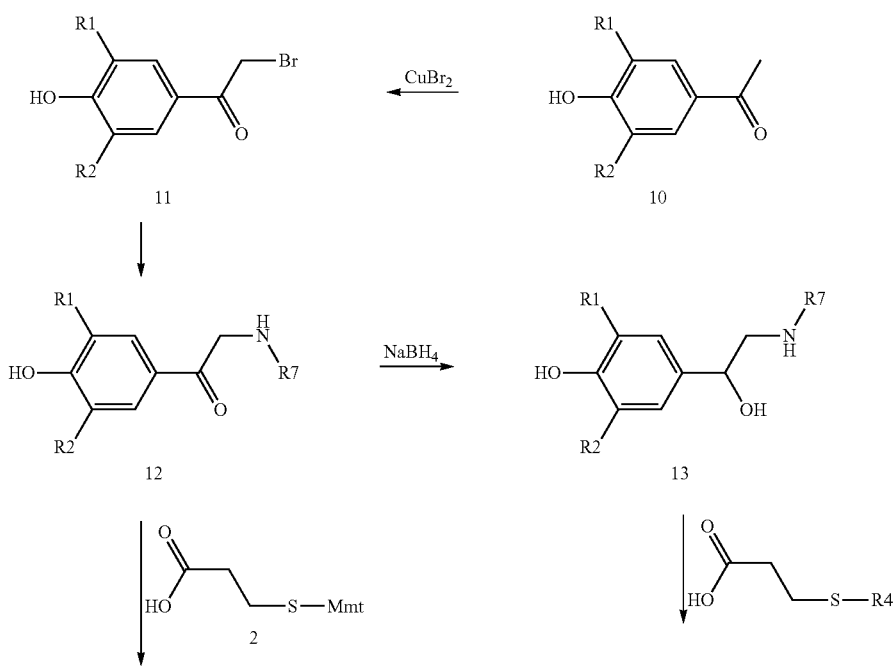

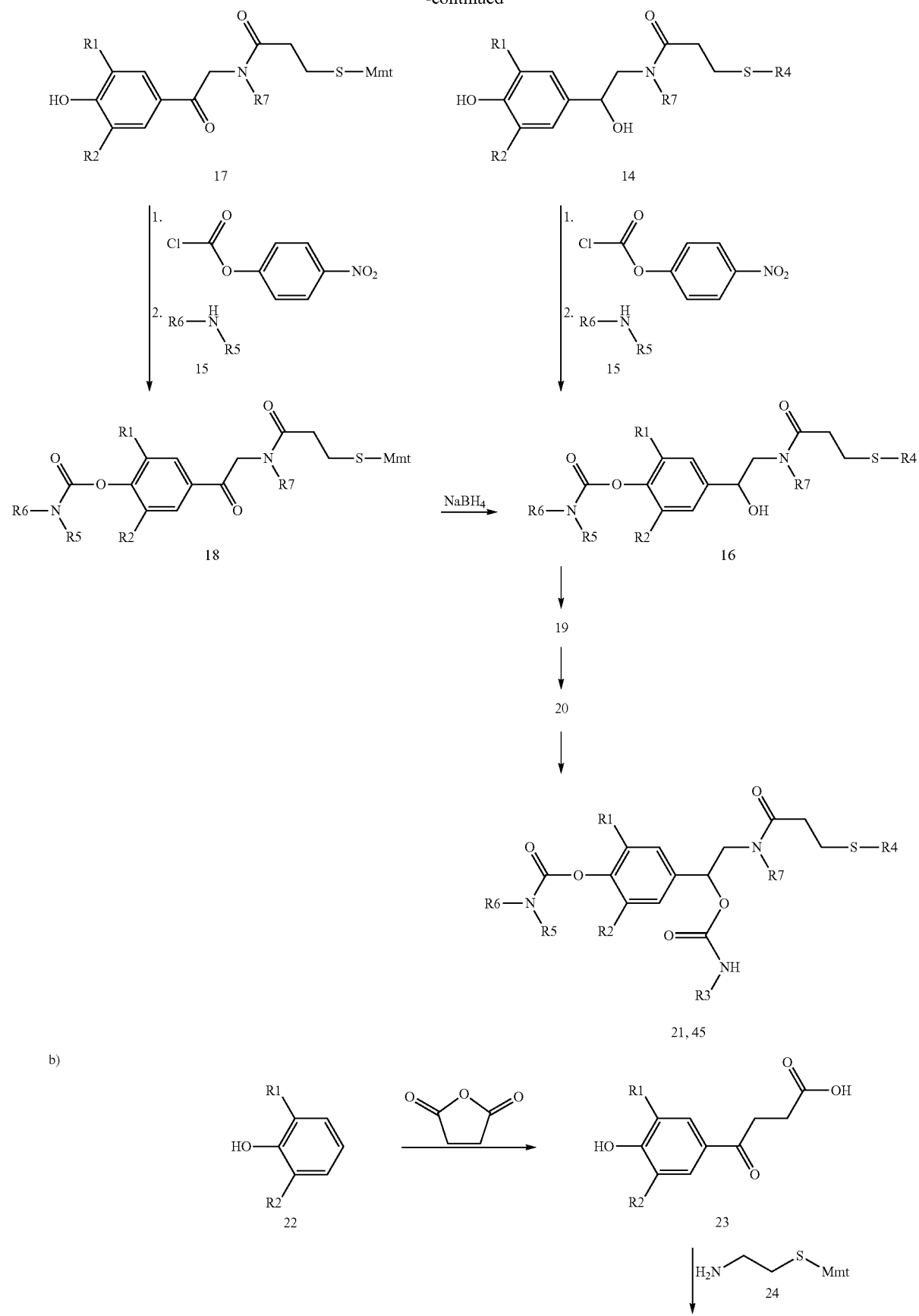

27  28
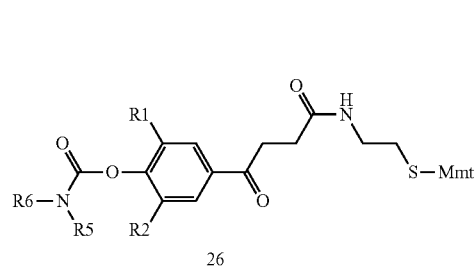
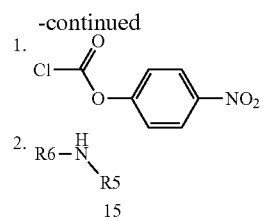
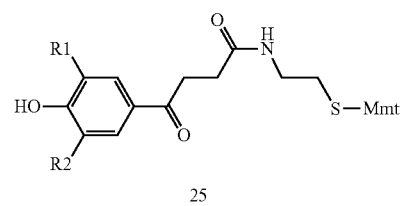
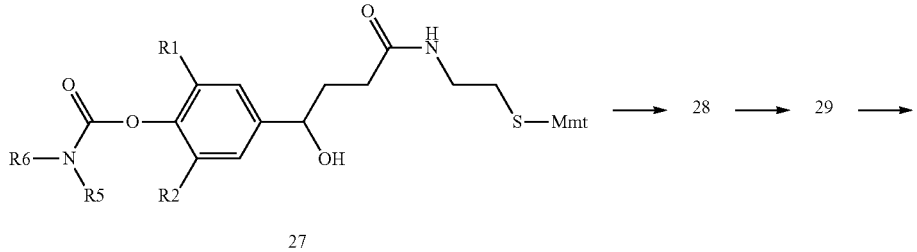
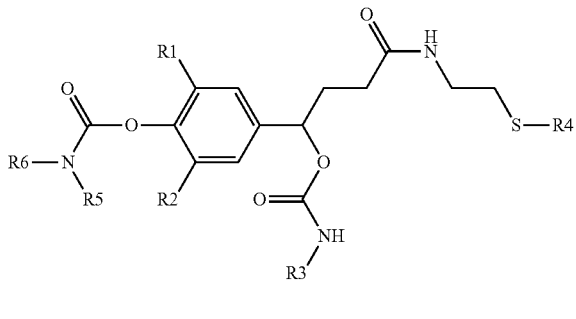
c)
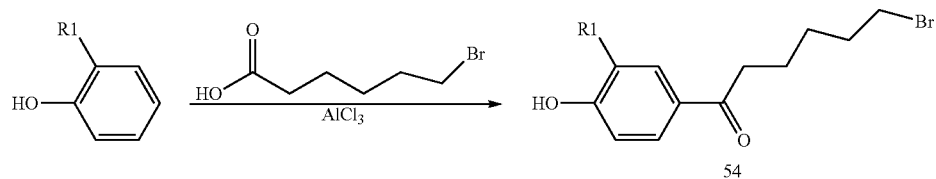
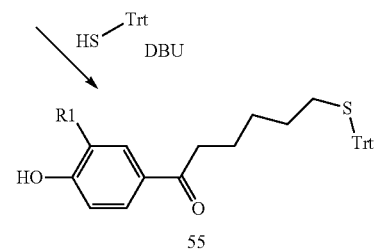
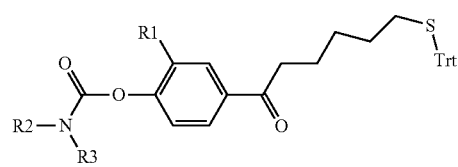

29 30
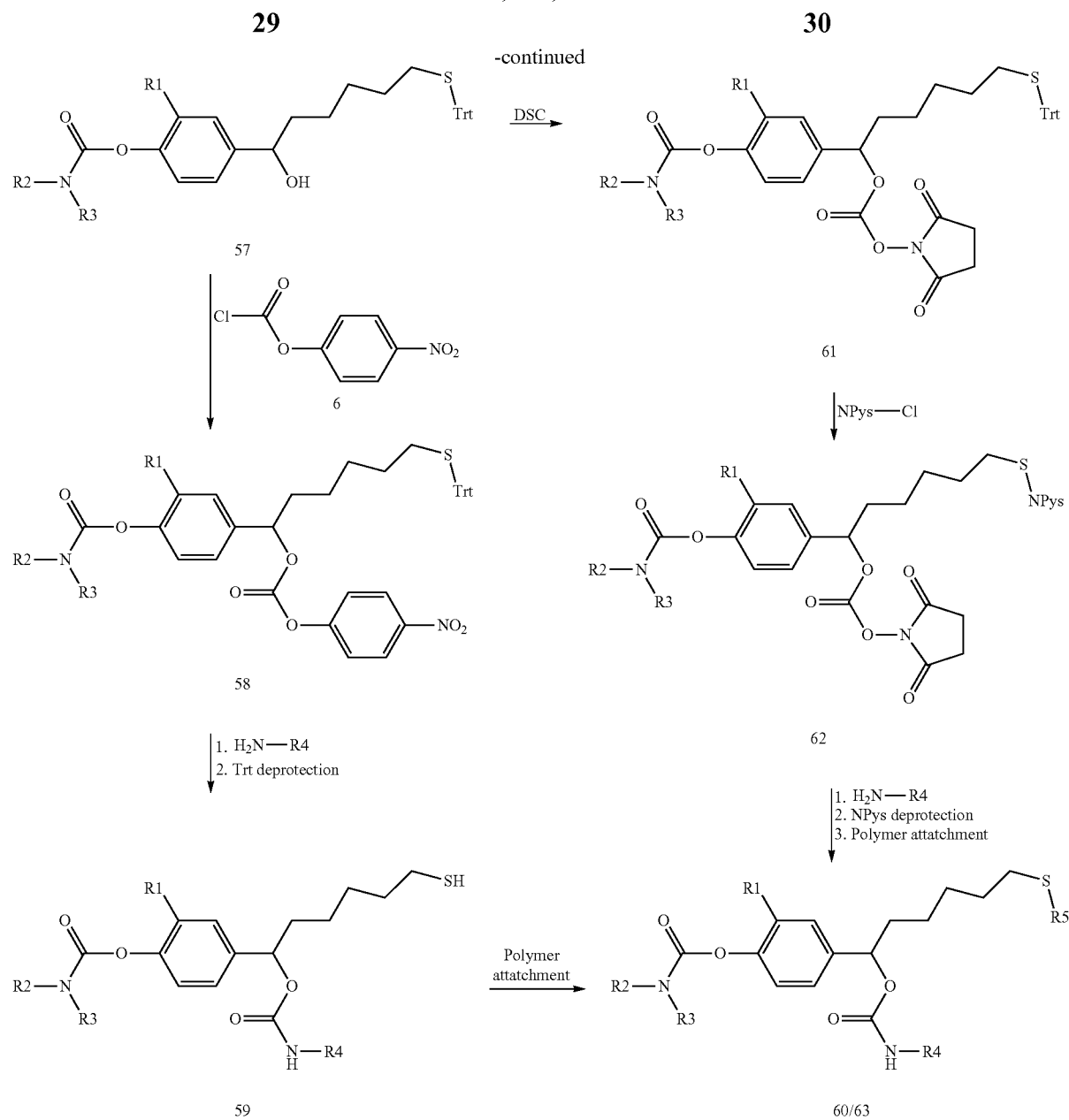
Synthesis of Polymeric Prodrugs According to Formula Ib with a Carbamate-linked Masking Group
a)
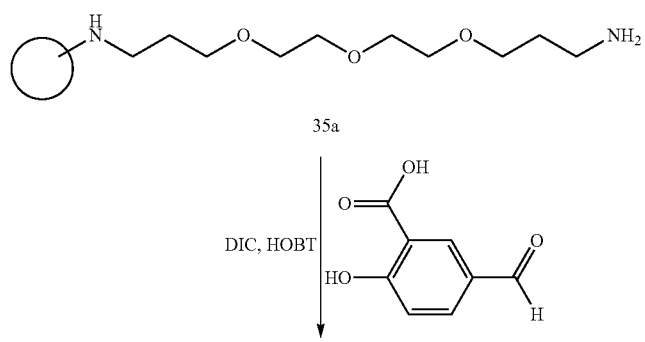

-continued
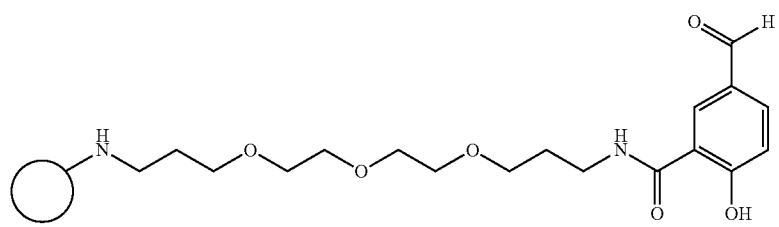
36a
1. BH₃, THF or LiAlH₄
2. AcOH, DIC, HOBt
3. HFIP
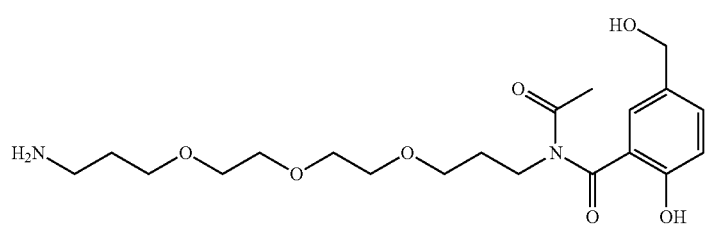
37a
2. PyBOP, DIEA
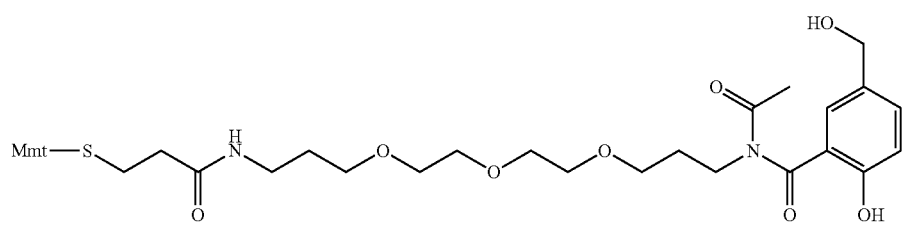
38
1. <image of 4-nitrophenyl chloroformate>
2. 15b -continued
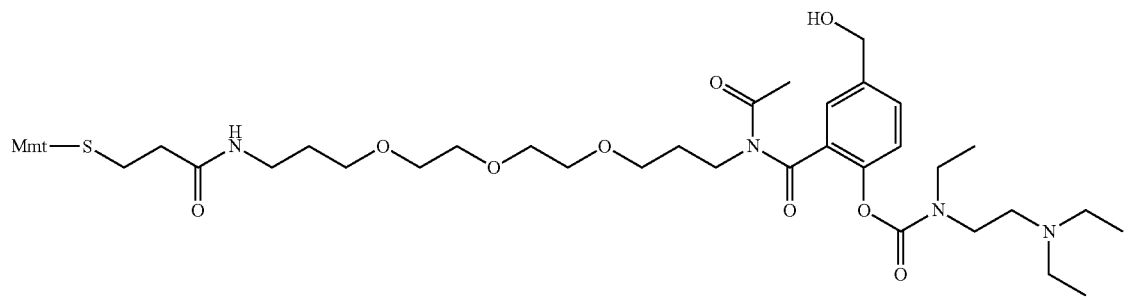
40a
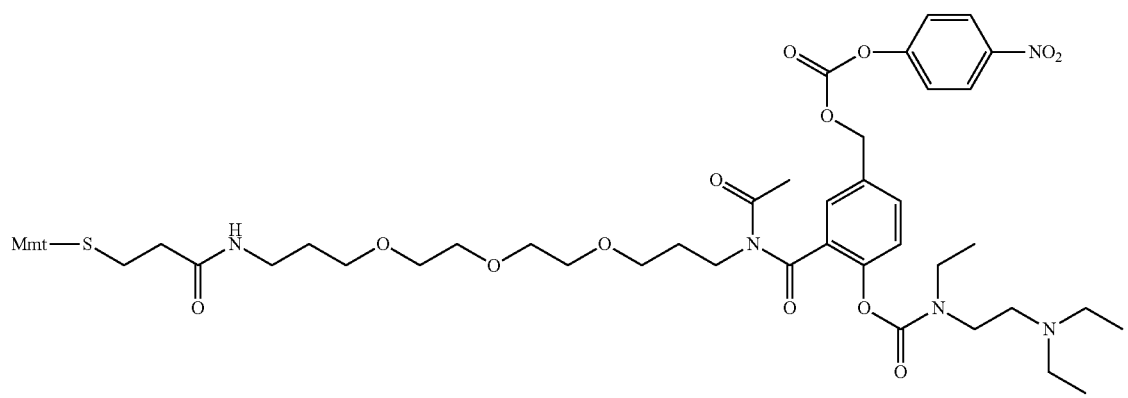
41a
b)
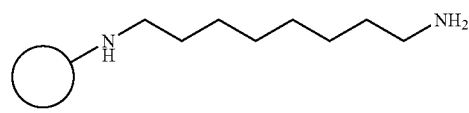
35b
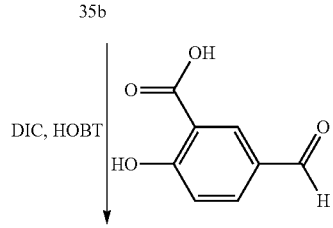

-continued
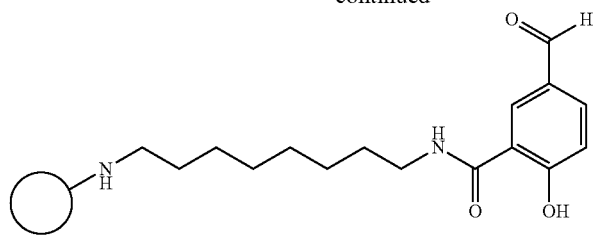
36b
1. BH₃, THF
2. AcOH, DIC, HOBt
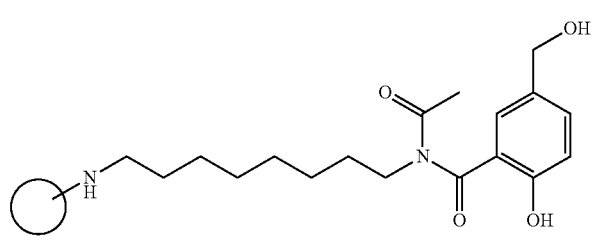
37a
1. 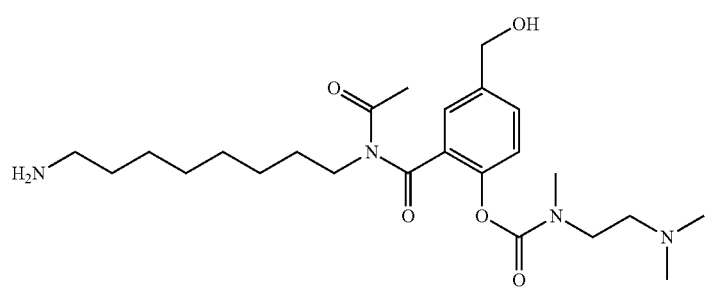
2. N,N,N'-trimethylethylendiamine
3. HFIP
39
2. PyBOP, DIEA
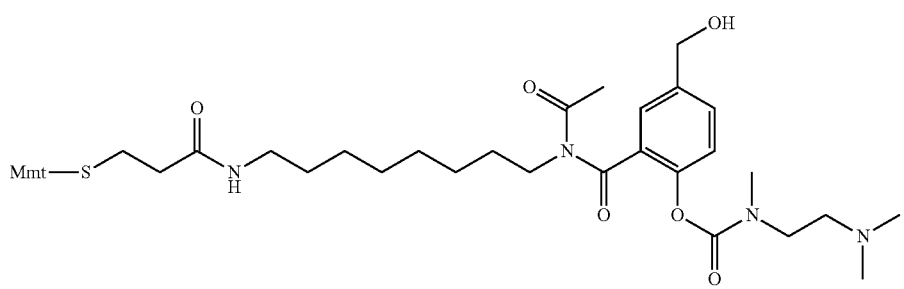
40b 41b

↓

42

↓

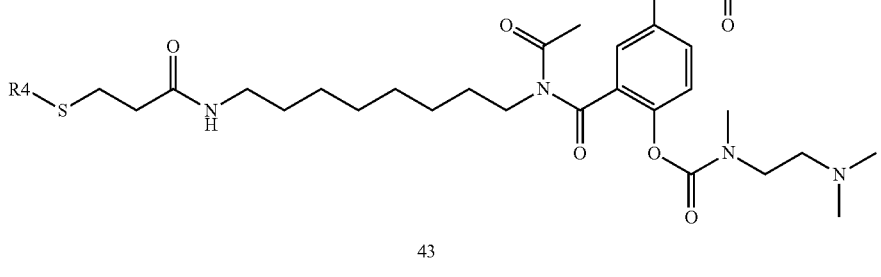

43

Synthesis of Compound 2

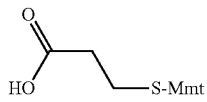
2

Mmt-chloride (1 eq) and mercaptopropionic acid (1.1 eq) were dissolved in TFA and incubated for 30 min. The solvent was removed under reduced pressure. The product was dissolved in pyridine, diluted in water, acidified by acetic acid and extracted with ether. The ether phase was separated and dried over $Na_2SO_4$. Solvent was removed under reduced pressure and product 2 was purified by RP-HPLC.

Synthesis of Compounds 3a and 3b

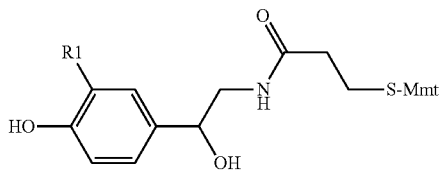

3a R1=H
3b R1=OMe

Octopamine hydrochloride (1a) (2 eq), DIEA (4 eq), and PyBOP (1 eq) were dissolved in DMF, 2 (1 eq) was added and the mixture was reacted for 50 min at room temperature. After addition of acetic acid (7 eq) product 3a was purified by RP-HPLC.

3b was synthesized from normetanephrine hydrochloride (1b) as described above.

3a: MS $[M+Na]^+$=536 (MW+Na calculated=536.2 g/mol)

3b: MS $[M+Na]^+$=566 (MW+Na calculated=566.2 g/mol)

Synthesis of mercaptothiazolide 4

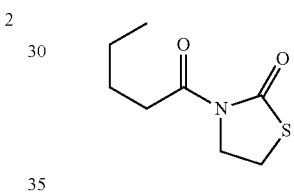
4

2-Mercaptothiazoline and triethylamine (1.5 eq) were dissolved in dry THF and pentanoyl chloride (1 eq) was added. The mixture was stirred for 1 h at 50° C. under inert gas atmosphere and was allowed to cool to room temperature, 0.5 N aqueous HCl was added and the separated organic phases were dried over $Na_2SO_4$. After concentration in vacuo the residue was purified by silica gel column chromatography using heptane/ethyl acetate (1/1) as mobile phase. Mercaptothiazolide 4 was collected as a viscous yellow oil.

4 $R_f$(heptane/ethyl acetate 1:1)=0.7

Synthesis of Compounds 5a and 5b

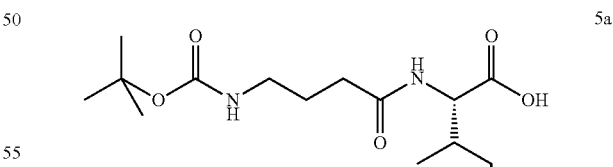
5a

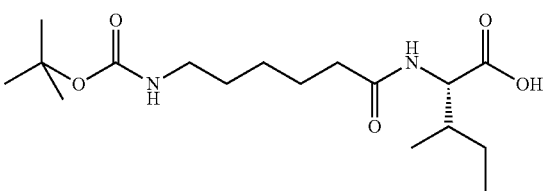
5b

General Synthesis Protocol:

1 g 2-chlorotrityl chloride resin (loading 1.6 mmol/g) was incubated for 1 h with 850 mg (2.4 mmol) Fmoc-Ile-OH and 840 µl (4.8 mmol) DIEA in 5 ml 1/1 DCM/DMF. After fmoc removal and washing of the resin with DMF, boc-aminobutyric acid was coupled to 0.5 g resin according to the standard coupling method. Compound 5a was cleaved from the resin with 97/1/2 (v/v) DCM/TFA/TES for 45 min. After neutralisation with pyridine, solvents were removed under reduced pressure and 5a was purified by RP-HPLC.

5b was synthesized from boc-aminohexanoic acid as described above.

5a MS [M+Na]$^+$=339.2 (MW+Na calculated=339.4 g/mol)

5b MS [M+Na]$^+$=367.4 (MW+Na, calculated=367.5 g/mol)

Synthesis of compound 6a

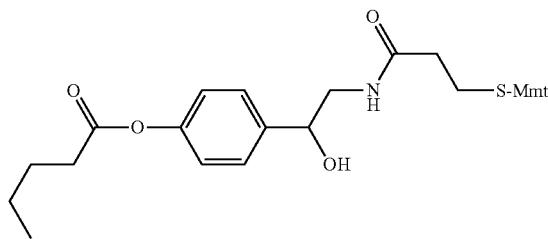

Mercaptothiazolide 4 (1 eq), phenol 3a (4 eq) and DMAP (4 eq) were refluxed in DCM for 2 h under nitrogen atmosphere. After neutralization with acetic acid, the solvent was removed in vacuo and product 6a was purified by RP-HPLC.

6a MS [M+Na]$^+$=620 (MW+Na calculated=620.3 g/mol)

Synthesis of Compounds 6b to 6e

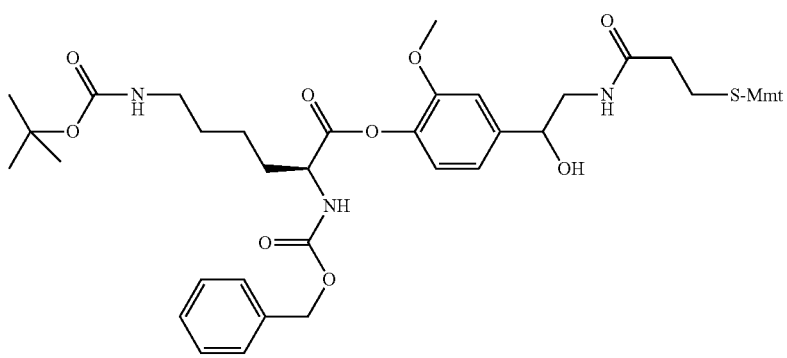

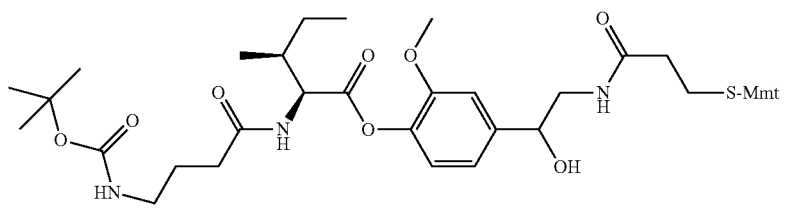

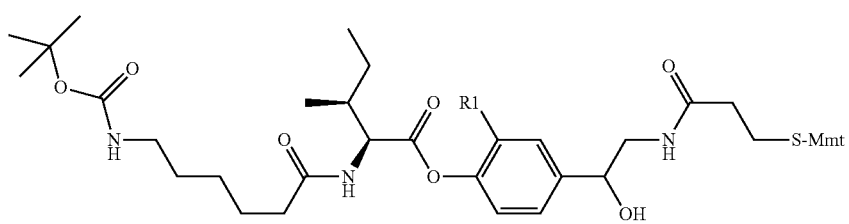

6d R1 = OMe
6e R1 = H

General Synthesis Protocol:

Carboxylic acid 5a (1 eq), phenol 3b (1 eq), DIC (1 eq), and DMAP (2 eq) in DMF were reacted for 1 h at room temperature. After addition of acetic acid (4 eq) the resulting carboxylic ester 6c was purified by RP-HPLC.

6d was synthesized as described above using 5b and 3b as starting materials.

6b was synthesized as described above using Z-Lys(Boc)-OH and 3b.

6e was synthesized as described above using 5b and 3a.

6b MS [M+Na]$^+$=928 (MW+Na calculated=928.6 g/mol)
6c MS [M+Na]$^+$=864 (MW+Na calculated=864.5 g/mol)
6d MS [M+Na]$^+$=892 (MW+Na calculated=892.6 g/mol)
6e MS [M+Na]$^+$=862 (MW+Na calculated=862.6 g/mol)

Synthesis of Compounds 7a to 7e

General Synthesis Protocol:

Alcohol 6a (1 eq), 4-nitrophenyl chloroformate (10 eq), and DIEA (10 eq) were stirred in dry dioxane for 3 h at room temperature under nitrogen atmosphere. After addition of acetic acid (25 eq) the mixtures were diluted with 7/3 (v/v) acetonitrile/H$_2$O and the carbonate 7a was purified by RP-HPLC.

7b, 7e, 7d, or 7e were synthesized from 6b, 6c, 6d, or 6e, respectively, as described above.

7a MS [M+Na]$^+$=785 (MW+Na calculated=785.5 g/mol)
7b MS [M+Na]$^+$=1093 (MW+Na calculated=1093.7 g/mol)
7c MS [M+Na]$^+$=1029 (MW+Na calculated=1029.6 g/mol)

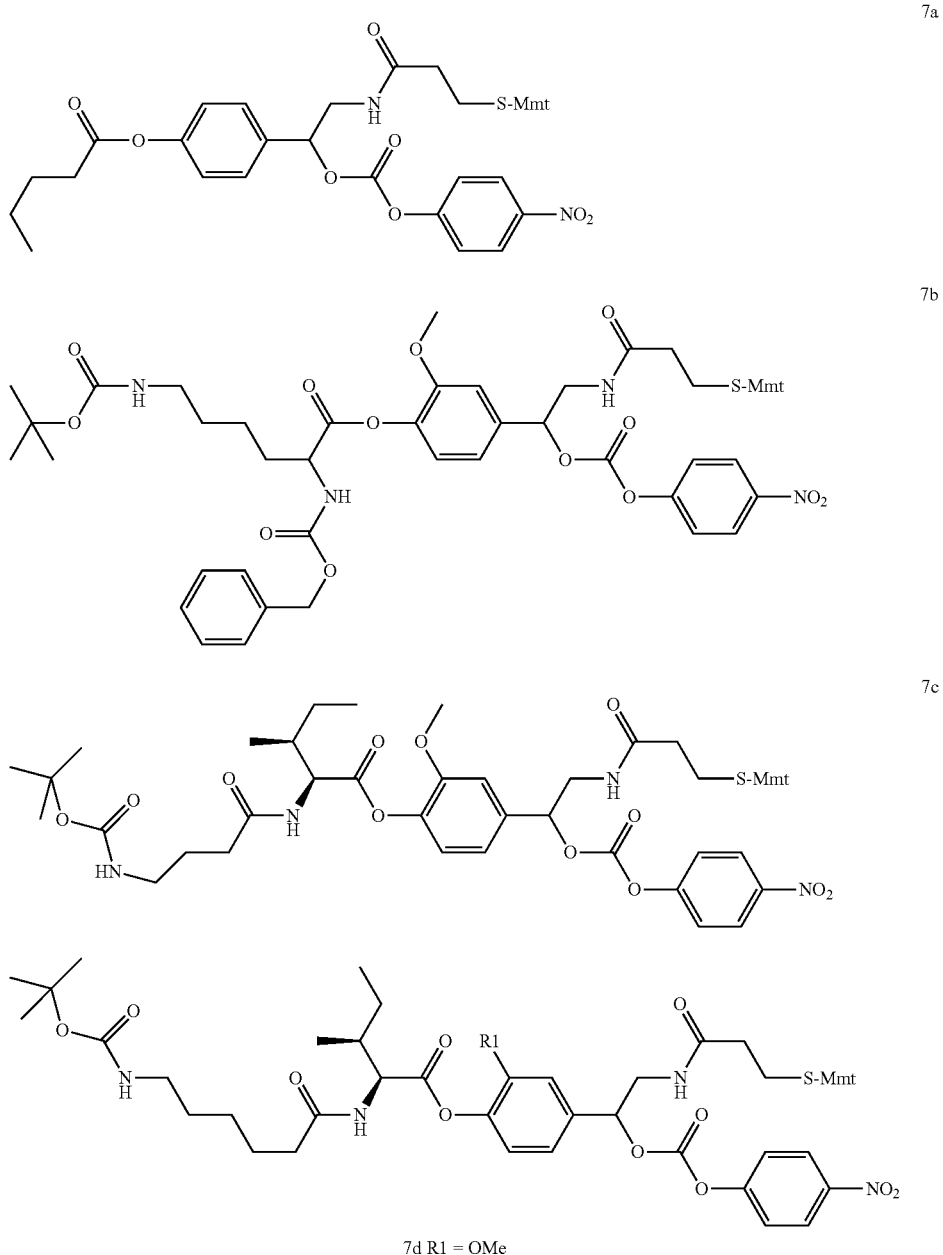

7d R1 = OMe
7e R1 = H

7d MS [M+Na]⁺=1057 (MW+Na calculated=1057.6 g/mol)

7e MS [M+Na]⁺=1027 (MW+Na calculated=1027.6 g/mol)

Synthesis of Compounds 8a to 8c (N^{αA1}-linker-insulin)

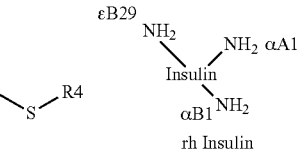

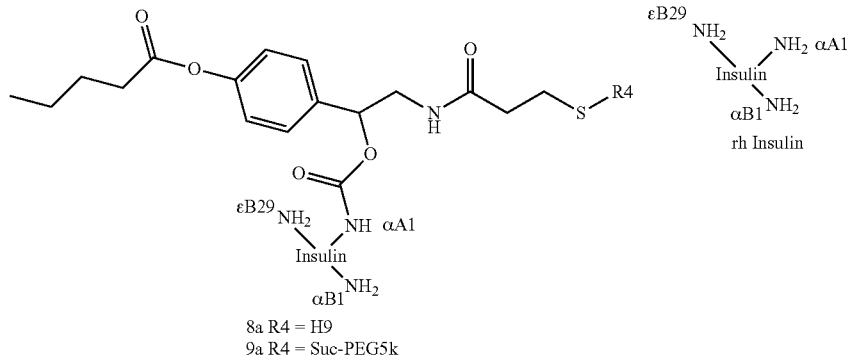

8a R4 = H
9a R4 = Suc-PEG5k

After lyophilization, the Mmt-protected intermediate was mixed with 95:5 (v/v) TFA/triethylsilane and stirred for 5 min. Volatiles were removed under nitrogen flow and 8a was purified by RP-HPLC and lyophilized, Regioselectivity of insulin modification was verified by DTT reduction and MS analysis.

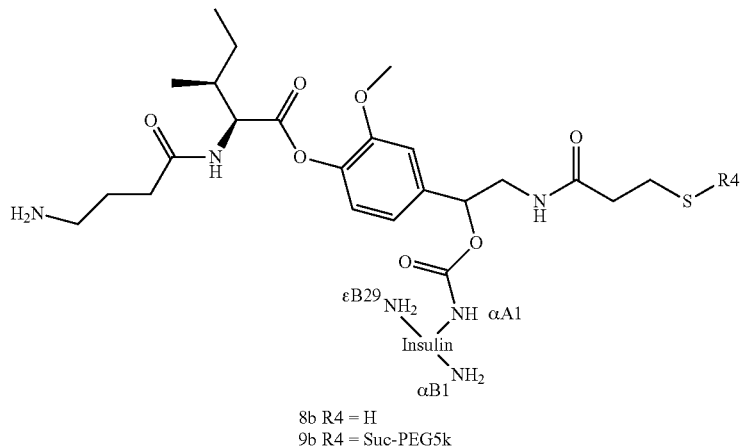

8b R4 = H
9b R4 = Suc-PEG5k

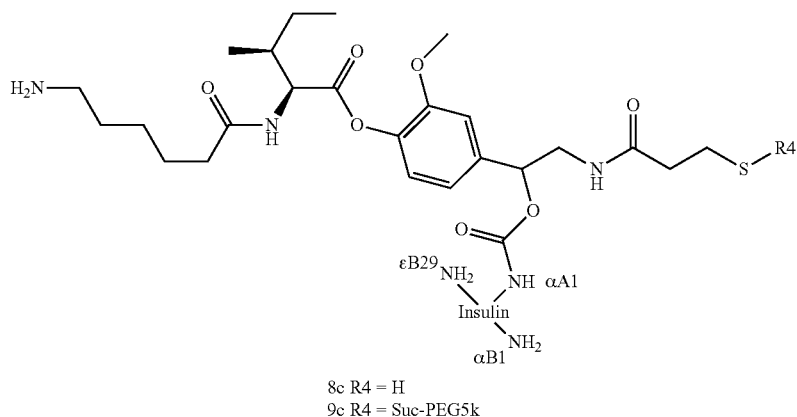

8c R4 = H
9c R4 = Suc-PEG5k

General Synthesis Protocol:

Rh-Insulin in 1/1 (v/v) DMSO/DMF was mixed with a solution of 0.9 eq carbonate 7a in DMSO. The resulting solution was adjusted to basic pH with DIEA and stirred for 1.5 h at RT. RP-HPLC purification gave Mmt-protected intermediate.

8b or 8c were synthesized from 7c, or 7d, respectively, as described above.

8a MS [M+2H]²⁺=3078.9; [M+3H]³⁺=2053.2 [M+4H]⁴⁺=1540.6 (MW calculated=6158 g/mol)

8b MS [M+2H]²⁺=3152.9; [M+3H]³⁺=2100.6 [M+4H]⁴⁺=1575.8 (MW calculated=6302 g/mol)

8c MS: [M+3H]³⁺=2110.7; [M+4H]⁴⁺=1583.7; [M+5H]⁵⁺=1266.6 (MW calculated=6330 g/mol)

Synthesis of Compounds 8d to 8g ($N^{\epsilon B29}$-Fluorescein-$N^{\alpha A1}$-linker-insulin)

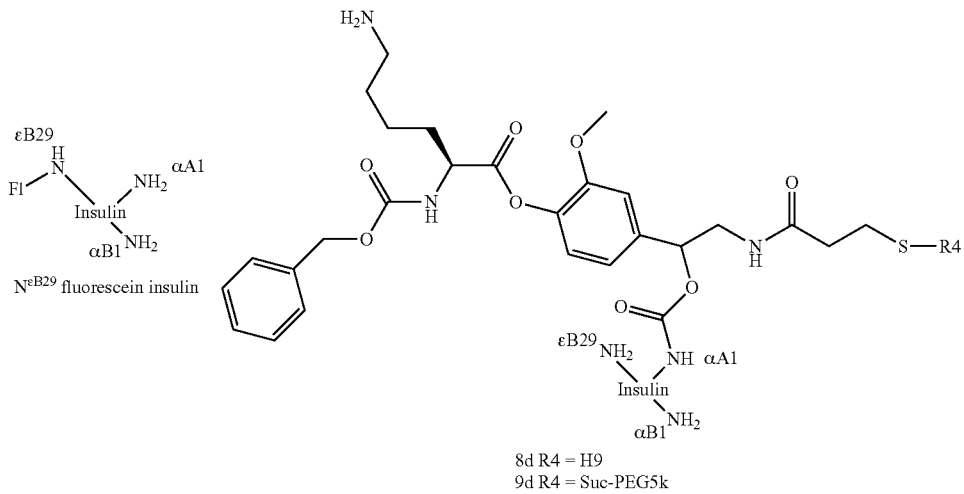

8d R4 = H
9d R4 = Suc-PEG5k

8e R4 = H
9e R4 = Suc-PEG5k

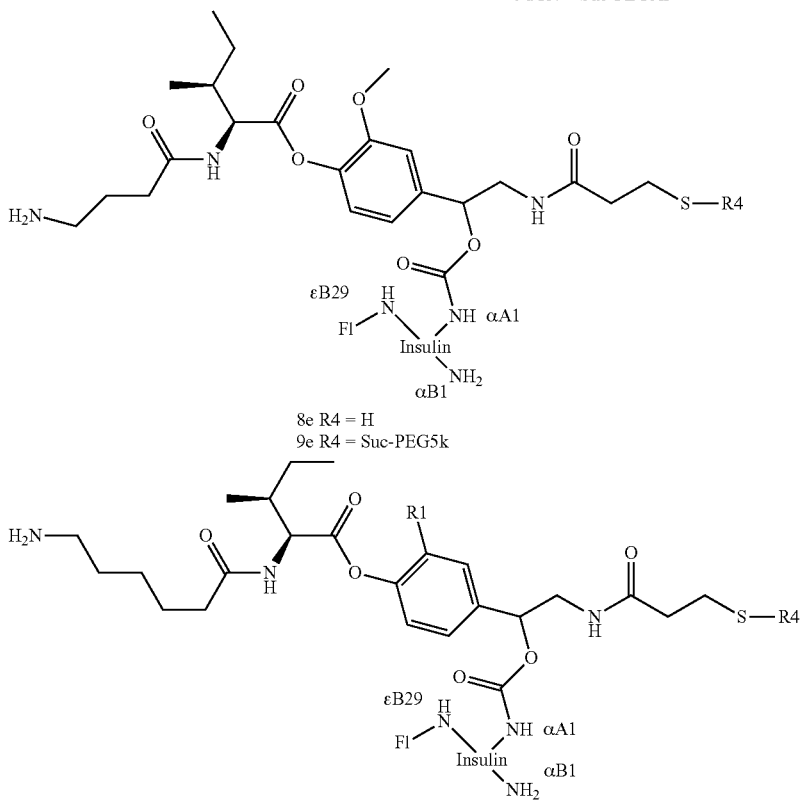

8f R4 = OMe, R4 = H
8g R1 = H, R4 = H
9f R1 = OMe, R4 = Syc-PEG5k
9g R1 = H, R4 = Suc-PEG5k

Suc = succinimidyl

Synthesis of $N^{\epsilon B29}$-fluorescein Insulin:

80 mg (13.8 µmol) rh-insulin were dissolved in 4 ml 1/1 (v/v) DMF/DMSO and 40 µl DIEA were added. 8 mg (17 µmol) 5-(and -6)-carboxyfluorescein succinimidyl ester were added and the solution was stirred for 30 min at room temperature. 4 ml 5/5/1 (v/v/v) acetonitrile/water/acetic acid were added, product $N^{\epsilon B29}$-fluorescein insulin was purified by RP-HPLC and lyophilized. The conjugation site was verified by reduction of $N^{\epsilon B29}$-fluorescein insulin with 1,4-dithiothreitol, protease digestion and MS analysis.

MS: $[M+2H]^{2+}=3084.0$; $[M+3H]^{3+}=2054.6$ (MW calculated=6166 g/mol)

$N^{\epsilon B29}$-fluorescein insulin in 1/1 (v/v) DMF/DMSO was mixed with a solution of 0.9 eq carbonate 7b in DMSO. The resulting solution was adjusted to basic pH with DIEA and stirred for 3 h at RT. RP-HPLC purification gave Mmt-protected intermediate.

After lyophilization, the intermediate was dissolved in 95/5 (v/v) TFA/triethylsilane and stirred for 5 min. Volatiles were removed under nitrogen flow and 8d was purified by RP-HPLC and lyophilized.

8e, 8f, or 8g were synthesized as described above using 7c, 7d, or 7e, respectively.

8d MS: $[M+2H]^{2+}=3364.1$; $[M+3H]^{3+}=2242.7$; $[M+4H]^{4+}=1681.5$ (MW calculated=6724 g/mol)

8e MS: $[M+3H]^{3+}=2219.2$ $[M+4H]^{4+}=1665.9$; $[M+5H]^{5+}=1332.8$ (MW calculated=6660 g/mol)

8f MS: $[M+3H]^{3+}=2229.7$ $[M+4H]^{4+}=1673.3$; $[M+5H]^{5+}=1337.7$ (MW calculated=6689 g/mol)

8g MS: $[M+3H]^{3+}=2218.7$ $[M+4H]^{4+}=1664.9$ (MW calculated=6659 g/mol)

Synthesis of Compounds 9a to 9g (mono-pegylated insulin compounds)

70 μl 500 μM 8a in 1/4 (v/v) acetonitrile/water were mixed with 7 μl 10 mM maleimide-PEG5k in 1/4 (v/v) acetonitrile/water and 10 μl 0.5 M sodium phosphate buffer pH 7.0 and incubated for 15 min Compound 9a was purified by SEC (column: Superdex 200, flow rate: 0.75 ml/min) using 10 mM HEPES buffer (pH 7.4), 150 mM NaCl, 3 mM EDTA, and 0.005% Tween as mobile phase. The collected eluate (approximately 1.5 ml) was directly used as such for release rate determination.

9b, 9c, 9d, 9e, 9f, or 9g were synthesized as described above from 8b, 8c, 8d, 8e, 8f, or 8g, respectively.

9a through 9g: SEC retention time: 19.5 min

Synthesis of Compounds 11a and 11b

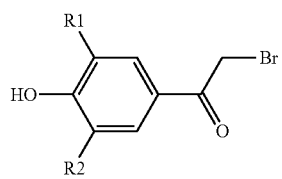

11a R1=R2=Me

11b R1=Me, R2=H 3,5-Dimethyl-4-hydroxy-acetophenone (5.0 mmol) (10a) and CuBr$_2$ (1.7 g, 7.5 mmol) were dissolved in 10 ml ethyl acetate and refluxed for 2 h. Solid byproducts were removed by filtration. The filtrate was evaporated and crude product 11a was purified by RP-HPLC.

11b was synthesized from 4-hydroxy-3-methyl-acetophenone (10b) (0.75 g, 5.0 mmol) as described above.

11a: Yield 754 mg (62%)

MS $[M+H]^+=243.1/245.1$ (MW+H calculated=244.1 g/mol)

11b: Yield 533 mg (47%)

MS $[M+H]^+=229.2/231.1$ (MW+H calculated=230.1 g/mol)

Synthesis of Compounds 12a and 12b

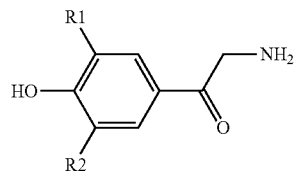

12a R1=R2=Me

12b R1=Me, R2=H 500 mg 11a (2.06 mmol) and 576 mg (4.11 mmol) hexamethylenetetramine were dissolved in 20 ml of trichloromethane and refluxed for 30 min. The solvent was removed in vacuo. 4 ml ethanol and 2 ml of concentrated HCl were added and the slurry was heated to 50° C. for 4 h. The mixture was concentrated in vacuo, diluted with acetonitrile/water and 12a was purified by RP-HPLC.

12b was synthesized from 472 mg (2.06 mmol) 11b as described above.

12a: Yield 547 mg (81%) as TFA-salt

MS $[M+Na]^+=202.2$ (MW+Na calculated=202.2 g/mol)

12b: Yield 455 mg (70%) as TFA-salt

MS $[M+Na]^+=188.2$ (MW+Na calculated=188.2 g/mol)

Synthesis of Compound 13

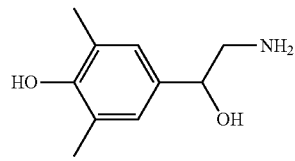

500 mg (1.71 mmol) 12a (TFA salt) were dissolved in 10 ml 1/1 (v/v) methanol/water, 129 mg (3.41 mmol) NaBH$_4$ were added and the mixture was stirred for 30 min at RT. 0.5 ml of acetic acid were added and 13 was purified by RP-HPLC.

13: Yield 313 mg (62%) as TFA-salt

MS $[M+Na]^+=204.2$ (MW+Na calculated=204.2 g/mol)

NMR (300 MHz, DMSO-d$_6$) δ [ppm]=8.25 (s, 1H, Phenol), 7.84 (bs, 3H, NH$_3^+$), 6.89 (s, 2H, CH$_{ar}$), 5.85 (d, 1H, Hydroxyl, J=3.7 Hz). 4.62 (m, 1H, CH$_{Benzyl}$), 2.93 (m, 1H, CH$_a$), 2.80 (m, 1H, CH$_b$), 2.17 (s, 6H, CH$_3$).

Synthesis of Compounds 14a to 14d

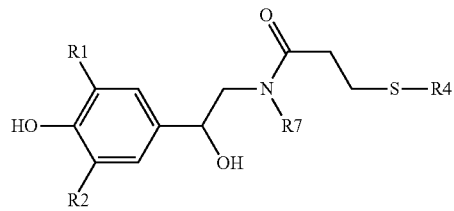

14a R1=R2=Me, R7=H, R4=Mmt
14b R1=R2=H, R7=Me, R4=Mmt
14c R1=OMe, R2=H, R7=Me, R4=Mmt
14d R1=H, R2=H, R7=Me, R4=Trt 13 (TFA salt 159 mg, 0.541 mmol) was coupled to compound 2 as described for compound 3a to yield 14a.

14b, or 14c were synthesized as described above using synephrine (335 mg, 2.00 mmol) or metanephrine (HCl salt, 281 mg, 1.20 mmol), respectively.

Synephrine (335 ma, 2.3 mmol) was coupled to 3-tritylsulfanyl-propionic acid as described above to yield 14d.

14a: Yield 254 mg (87%)
MS [M+Na]$^+$=564.7 (MW+Na calculated=564.3 g/mol)
14b: Yield 760 mg (72%)
MS [M+Na]$^+$=550.2 (MW+Na calculated=550.3 g/mol)
14c: Yield 530 mg (80%)
MS [M+Na]$^+$=580.4 (MW+Na calculated=580.4 g/mol)
14d: Yield 567 mg (49%)
MS [M+Na]$^+$=520.5 (MW+Na calculated=520.7 g/mol)

Synthesis of Compounds 15c, 15d and 15f

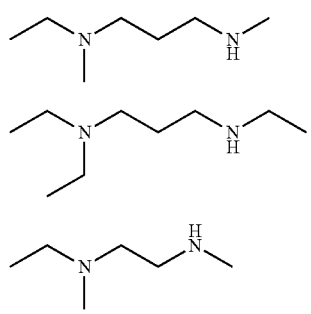

General Synthesis Protocol:

1 g 2-chlorotrityl chloride resin (loading 1.4 mmol/g) was incubated for 1 h with N,N'-dimethylpropane-1,3-diamine (for synthesis of 15c), or N,N'-diethyl-propane-1,3-diamine (for synthesis of 15d) or N,N'-dimethyl-ethane-1,2-diamine (4 eq) (for synthesis of 15f) in DCM. After washing of the resin with DMF, amines were acetylated with 1/1/2 (v/v/v) acetic anhydride/pyridine/DMF for 14 h. The resin was washed with THF and dried. LiAlH$_4$ (1 M in THF, 4 eq) was added dropwise to the suspended resin in THF. The resulting suspension was stirred for 3 h at 45° C. under nitrogen atmosphere. After cooling, aqueous Rochelle's salt solution was added and the resin was separated and dried. Compounds were cleaved from resin with 2/1 (v/v) HFIP/DCM (2×30 min) The volatile components were evaporated and the products 15c, 15d or 15f were used in the following steps without further purification.

15c MS, [M+H]$^+$=131.2 (MW=130.1 g/mol)
15d MS [M+H]$^+$=159.2 (MW=158.1 g/mol)
15f MS [M+H]$^+$=117.1 (MW=116 g/mol)

Synthesis of Compounds 16a to 16f and 16i

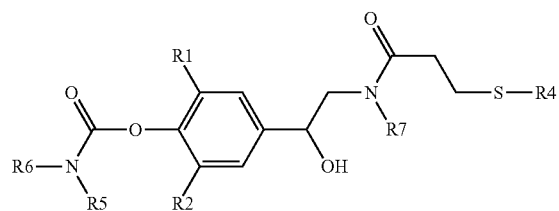

16a R1=R2=R5=Me, R6=2-(dimethylamino)ethyl, R7=H, R4=Mmt
16b R1=OMe, R2=H, R5=Et, R6=2-(diethylamino)ethyl, R7=H., R4=Mmt
16c R1=OMe, R2=H, R5=Me, R6=3-(N-ethyl-N-methylamino)propyl, R7=Me, R4=Mmt
16d R1=R2=H, R5=Me, R6=3-(N-ethyl-N-methylamino) propyl, R7=Me, R4=Mmt
16e R1=OMe, R2=H, R5=Et, R6=3-(diethylamino)propyl, R7=Me, R4=Mmt
16f R1=R2=H, R5=Et, R6=3-(diethylamino)propyl, R7=Me, R4=Mmt
16i R1=R2=H, R5=Et, R6=2-(diethylamino)ethyl, R7=Me, R4=Trt 14a (120 mg, 0.222 mmol) was dissolved in 1.5 ml of dry THF, p-Nitrophenyl-chloroformate (45 mg, 0.222 mmol) and DIEA (113 µl, 0.665 mmol) were added and the mixture was stirred for 30 min at RT. 15a (N,N,N'-trimethyl-ethylene-1,2-diamine) (72 µl, 0.554 mmol) was added and stilling was continued for 30 min. The solvent was removed in vacuo, 100 µl of AcOH were added and 16a was purified by RP-HPLC.

16b was synthesized as described above from 3b (80 mg, 0.15 mmol) and 15b (N,N,N'-triethyl-ethylene-1,2-diamine) (55 mg, 0.38 mmol).

16c or 16d were synthesized as describe above from 14c (56 mg, 0.1 mmol) or 14b (53 mg, 0.1 mmol), respectively, and diamine 15c.

16e or 16f were synthesized as described above from 14c (56 mg, 0.1 mmol) or 14b, respectively, (53 mg, 0.1 mmol) and diamine 15a.

16i was synthesized as described above from 14d (350 mg, 0.7 mmol) and 15b (N,N,N'-triethyl-ethylene-1,2-diamine) (180 µl, 1 mmol).

16a: Yield 120 mg (69%) as TFA salt
MS [M+Na]$^+$=692.4 (MW+Na calculated=692.9 g/mol)
16b: Yield 48 mg (40%) as TFA salt
MS [M+Na]$^+$=736.3 (MW+Na calculated=736.4 g/mol)
16c: Yield 8 mg (10%) as TFA salt
MS [M+Na]$^+$=736.4 (MW+Na calculated=736.4 g/mol)
16d: Yield 20 mg (25%) as TFA salt
MS [M+Na]$^+$=706.3 (MW+Na calculated=706.3 g/mol)
16e: Yield 2 mg (3%) as TFA salt
MS [M+Na]$^+$=764.6 (MW+Na calculated=764.4 g/mol)
16f: Yield 6 mg (8%) as TFA salt
MS [M+Na]$^+$=734.4 (MW+Na calculated=734.3 g/mol)
16i: Yield 152 mg (28%) as TFA salt
MS [M+Na]$^+$=690.5 (MW+Na calculated=690.9 g/mol)

Synthesis of Compound 17

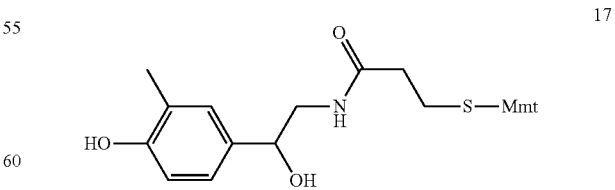

Amine 12b (TFA salt) was coupled to compound 2 as described for compound 3a.

17: Yield 608 mg (74%)
MS [M+Na]$^+$=548.3 (MW+Na calculated=548.7 g/mol)

Synthesis of Compounds 18a and 18b

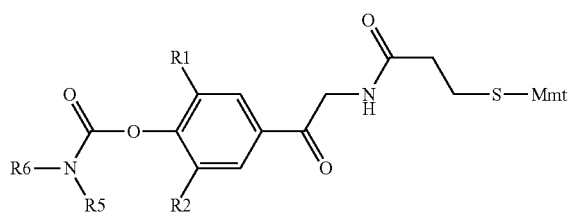

18a R1=R5=Me, R2=R6=3-(dimethylamino)propyl
18b R1=R5=Me, R2=H, R6=2-(N-ethyl-N-methylamino)ethyl 383 mg (0.729 mmol) of 17 were reacted with p-nitrophenyl-chloroformate and N,N,N'-trimethyl-propane-1,3-diamine (15e) or 15f, respectively, to yield 18a or 18b as described for compound 16a.

18a: Yield 287 mg (50%) as TFA salt
MS [M+Na]$^+$=690.7 (MW+Na calculated=690.9 g/mol)
18b: Yield 148 mg (26%) as TFA salt
MS [M+Na]$^+$=690.9 (MW+Na calculated=690.9 g/mol)

Synthesis of Compounds 16a and 16h

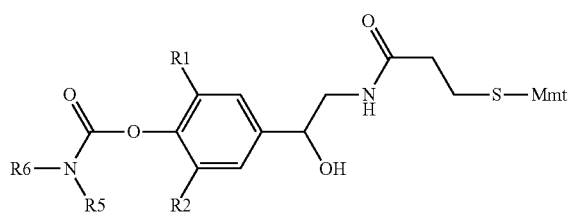

16g R1=R5=Me, R2=H, R6=3-(dimethylamino)propyl
16h R1=R5=Me, R2=H, R6=2-(N-ethyl-N-methylamino)ethyl 18a (287 mg, 0.367 mmol, TFA salt) was dissolved in 5 ml methanol, NaBH$_4$ (41 mg, 1.07 mmol) was added and the mixture was stirred for 30 min at RT, 0.5 ml of acetic acid were added and 16g was purified by RP-HPLC.

18b (8 mg, 0.010 mmol, TFA salt) was reacted as described above to yield 16h.

16g: Yield 201 mg (70%) as TFA-salt
MS [M+Na]$^+$=692.7 (MW+Na calculated=692.9 g/mol)
16h: Yield 6 mg (77%) as TFA-salt
MS [M+Na]$^+$=692.7 (MW+Na calculated=692.9 g/mol)

Synthesis of Compounds 19a to 19i

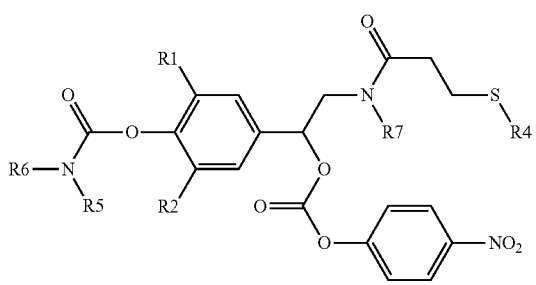

19a R1=R2=R5=Me, R6=2-(dimethylamino)ethyl, R7=H, R4=Mmt
19b R1=OMe, R2=H, R5=Et, R6=2-(diethylamino)ethyl, R7=H, R4=Mmt
19c R1=OMe, R2=H, R5=Me, R6=3-(N-ethyl-N-methylamino)propyl, R7=Me, R4=Mmt
19d R1=R2=H, R5=Me, R6=3-(N-ethyl-N-methylamino)propyl, R7=Me, R4=Mmt
19e R1=OMe, R2=H, R5=Et, R6=3-(diethylamino)propyl, R7=Me, R4=Mmt
19f R1=R2=H, R5=Et, R6=3-(diethylamino)propyl, R7=Me, R4=Mmt
19g R1=R5=Me, R2=H, R6=3-(dimethylamino)propyl, R7=H, R4=Mmt
19h R1=R5=Me, R2=H, R6=2-(N-ethyl-N-methylamino)ethyl, R7=H, R4=Mmt
19i R1=R2=H, R5=Et, R6=2-(diethylamino)ethyl, R7=Me, R4=Trt Carbonates 19a to 19i were synthesized from 16a to 16i, respectively, as described for compound 7a.

19a: Yield 98 mg (72%) as TFA-salt
MS [M+Na]$^+$=857.8 (MW+Na calculated=858.0 g/mol)
19b: Yield 6 mg (11%) as TFA-salt
MS [M+Na]$^+$=901.8 (MW+Na calculated=901.5 g/mol)
19c: Yield 1 mg (15%) as TFA-salt
MS [M+Na]$^+$=901.4 (MW+Na calculated=901.5 g/mol)
19d: Yield 8 mg (29%) as TFA-salt
MS [M+Na]$^+$=871.4 (MW+Na calculated=871.4 g/mol)
19e: Yield 0.3 mg (18%) as TFA-salt
MS [M+Na]$^+$=929.4 (MW+Na calculated=929.5 g/mol)
19f: Yield 4 mg (45%) as TFA-salt
MS [M+Na]$^+$=899.7 (MW+Na calculated=899.6 g/mol)
19g: Yield 6 mg (6%) as TFA-salt
MS [M+Na]$^+$=857.8 (MW+Na calculated=858.0 g/mol)
19h: Yield 0.8 mg (11%) as TFA-salt
MS [M+Na]$^+$=857.7 (MW+Na calculated=858.0 g/mol)
19i: Yield 77 mg (49%) as TFA-salt
MS [M+Na]$^+$=856.2 (MW+Na calculated=856.0 g/mol)

Synthesis of Compounds 20a to 20f

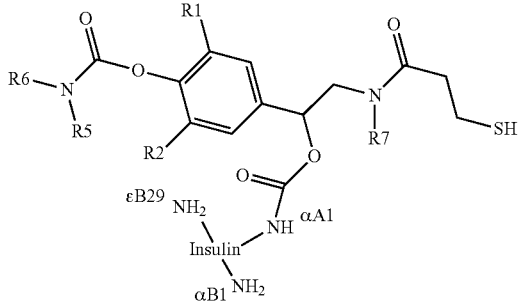

20a R1=R2=R5=Me, R6=2-(dimethylamino)ethyl, R7=H
20b R1=OMe, R2=H, R5=Et, R6=2-(diethylamino)ethyl, R7=H
20c R1=OMe, R2=H, R5=Me, R6=3-(N-ethyl-N-methylamino)propyl, R7=Me
20d R1=R2=H, R5=Me, R6=3-(N-ethyl-N-methylamino)propyl, R7=Me
20e R1=R5=Me, R2=H, R6=3-(dimethylamino)propyl, R7=H
20f R1=R5=Me, R2=H, R6=2-(N-ethyl-N-methylamino)ethyl, R7=H Insulin derivatives 20a, 20b, 20c, 20d, 20e, or 20f were synthesized from 19a, 19b, 19c, 19d, 19g, or 19h respectively, as described for compound 8a.

20a MS [M+3H]$^{3+}$=2077.3 [M+4H]$^{4+}$=1559.2 (MW calculated=6231.3 g/mol)

20b MS $[M+3H]^{3+}$=2093.0 $[M+4H]^{4+}$=1569.6 (MW calculated=6274 g/mol)

20c MS $[M+3H]^{3+}$=2090.8 $[M+4H]^{4+}$=1568.7 (MW calculated=6274 g/mol)

20d MS $[M+3H]^{3+}$=2081.3 $[M+4H]^{4+}$=1561.8 (MW calculated=6244 g/mol)

20e MS $[M+3H]^{3+}$=2077.1 $[M+4H]^{4+}$=1558.2 (MW calculated=6231.3 g/mol)

20f MS $[M+3H]^{3+}$=2076.7 $[M+4H]^{4+}$=1559.3 (MW calculated=6231.3 g/mol)

Synthesis of Compounds 21a to 21f (mono-pegylated insulin derivatives)

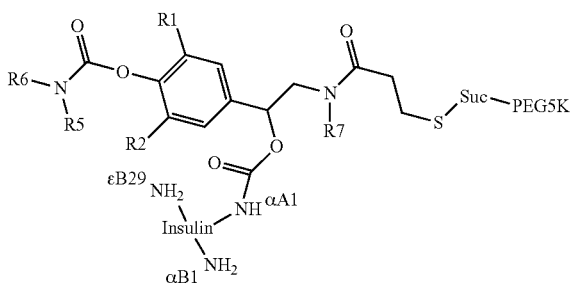

21a R1=R2=R5=Me, R6=2-(dimethylamino)ethyl, R7=H

21b R1=OMe, R2=H, R5=Et, R6=2-(diethylamino)ethyl, R7=H

21c R1=OMe, R2=H, R5=Me, R6=3-(N-ethyl-N-methylamino)propyl, R7=Me

21d R1=R2=H, R5=Me, R6=3-(N-ethyl-N-methylamino)propyl, R7=Me

21e R1=R5=Me, R2=H, R6=3-(dimethylamino)propyl, R7=H

21f R1=R5=Me, R2=H, R6=2-(N-ethyl-N-methylamino)ethyl, R7=H

Insulin derivatives 21a, 21b, 21c, 21d, 21e, or 21f were synthesized from compound 20a, 20b, 20c, 20d, 20e, or 20f, respectively, as described for compound 9a.

21a through 21f: SEC retention time: 19.5 min

Synthesis of Compounds 23a and 23b

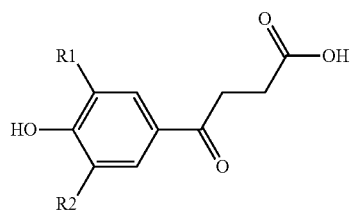

23a R1=Me, R2=H
23b R1=R2=Me o-Cresol (22a) (1 eq), succinic anhydride (1 eq), and $AlCl_3$ (3 eq) in nitrobenzene were heated to 100° C. for 1 h. The reaction mixture was poured on HCl/ice and extracted with ether. The organic layer was extracted with 1 N NaOH and the aqueous layer was acidified with concentrated HCl. The aqueous layer was extracted with ether and the ether was evaporated. 23a was purified by RP-HPLC. 23b was synthesized from 2,6-dimethylphenol (22b) as described above.

23a: Yield 552 mg (31%)

MS $[M+Na]^+$=231.0 (MW+Na calculated=231.2 g/mol)

NMR (300 MHz, DMSO-$d_6$) δ[ppm]=12.05 (bs, 1H, $CO_2H$), 10.23 (s, 1H, phenol OH), 7.74 (s, 1H, $CH_{ar}$), 7.7 (d, 1H, $CH_{ar}$, $^3J_{H,H}$=8.4 Hz), 6.86 (d, 1H, $CH_{ar}$, $^3J_{H,H}$=8.4 Hz), 3.13 (t, 2H, $C(O)CH_2$, $^3J_{H,H}$=6.4 Hz), 2.53 (t, 2H, $CH_2 CO_2$, $^3J_{H,H}$=6.4 Hz), 2.16 (s, 3H, $CH_3$)

23b: Yield 166 mg (15%)

MS $[M+Na]^+$=245.4 (MW+Na calculated=245.2 g/mol)

Synthesis of Compound 24

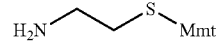

1.85 g (16.02 mmol) cysteamine hydrochloride were dissolved in 15 ml of TFA and 2.47 g (8.01 mmol) MmtCl were added. After stirring the mixture at RT for 20 min the solvent was evaporated in vacuo. The residue was dissolved in diethyl ether and extracted with saturated aqueous $NaHCO_3$, 1N $H_2SO_4$ and brine. The solvent was evaporated and 24 was purified by RP-HPLC.

24: Yield 1.11 g (30%) as TFA salt

TLC (AcOEt/$Et_3N$ 99/1), $R_f$=0.24

Synthesis of Compounds 25a and 25b

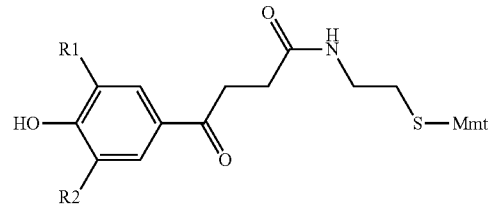

25a R1=Me, R2=H

25b R1=R2=Me 23a (1 eq), HOBt (1.1 eq) and DIC (1 eq) were dissolved in DMF and stirred at RT for 30 min. 24 (TFA salt, 1 eq) and DIEA (3 eq) were added and the solution was stirred for 60 min. Acetic acid was added and 25a was purified by RP-HPLC. 25b was synthesized from 23b as described above.

25a: Yield 552 mg (25%)

MS $[M+Na]^+$=562.7 (MW+Na calculated=562.7 g/mol)

25b: Yield 15 mg (40%)

MS $[M+Na]^+$=576.6 (MW+Na calculated=576.6 g/mol)

Synthesis of Compounds 26a and 26b

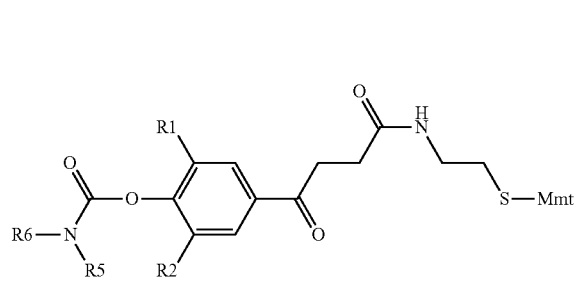

26a R1=Me, R2=H, R5=R6=3-(dimethylamino)propyl
26b R1=R2=R5=Me, R6=2-(dimethylamino)ethyl 267 mg (0.495 mmol) 25a was reacted with p-nitrophenyl-chloroformate and N-(3-dimethylamino-propyl)-N',N' dimethyl-propane-1,3-diamine (15 g) to yield 26a as described for compound 16a.

26b was synthesized as described above using 15 mg 25b and N,N,N'-trimethyl-ethane-1,2-diamine (15a).

26a: Yield 282 mg (58%) as double TFA salt
MS [M+Na]$^+$=775.2 (MW+Na calculated=776.0 g/mol)
26b: Yield 17 mg (70%) as TFA salt
MS [M+Na]$^+$=704.5 (MW+Na calculated=704.6 g/mol)

Synthesis of Compounds 27a and 27b

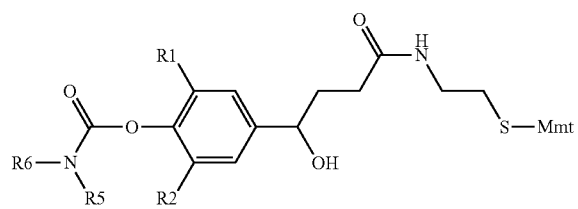

27a R1=Me, R2=H, R5=R6=3-(dimethylamino)propyl
27b R1=R2=R5=Me, R6=2-(dimethylamino)ethyl 26a (272 mg, 0.277 mmol, double TFA salt) was dissolved in 5 ml methanol, NaBH$_4$ (42 mg, 1.09 mmol) was added and the mixture was stirred for 30 min at RT 0.5 ml of acetic acid were added and 27a was purified by RP-HPLC.

Alcohol 27b was synthesized likewise from 26b (17 mg, 25 µmol, TFA salt).

27a: Yield 142 mg (52%) as double TFA salt
MS [M+Na]$^+$=777.9 (MW+Na calculated=778.0 g/mol)
27b: Yield 6 mg (40%) as TFA salt
MS [M+Na]$^+$=706.5 (MW+Na calculated=706.6 g/mol)

Synthesis of Compounds 28a and 28b

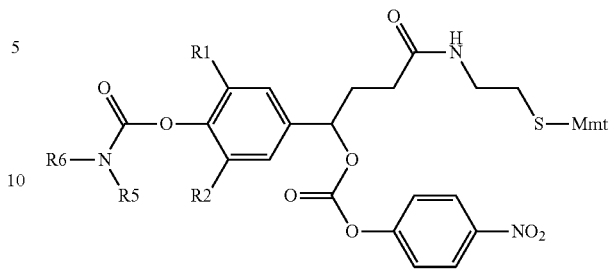

28a R1=Me, R2=H, R5=R6=3-(dimethylamino)propyl
28b R1=R2=R5=Me, R6=2-(dimethylamino)ethyl Carbonates 28a or 28b were synthesized from 27a or 27b, respectively, as described for compound 7a.

28a: Yield 1 mg (29%)
MS [M+Na]$^+$=942.9 (MW+Na calculated=943.2 g/mol)
28b: Yield 1.5 mg (19%)
MS [M+Na]$^+$=871.6 (MW+Na calculated=871.7 g/mol)

Synthesis of Compounds 29a and 29b

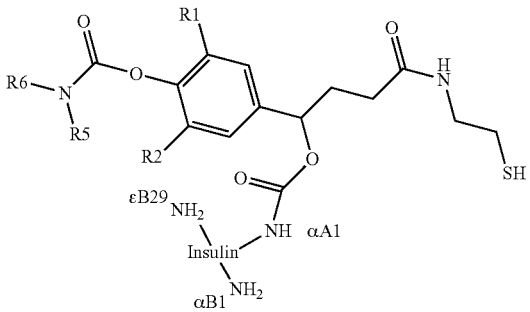

29a R1=Me, R2=H, R5=R6=3-(dimethylamino)propyl
29b R1=R2=R5=Me, R6=2-(dimethylamino)ethyl Insulin derivatives 29a or 29b were synthesized from 28a or 28b, respectively, as described for compound 8a.

29a MS [M+3H]$^{3+}$=2105.8 [M+4H]$^{4+}$=1580.2 (MW calculated=6316.4 g/mol)
29b MS [M+3H]$^{3+}$=2081.8 [M+4H]$^{4+}$=1562.4 (MW calculated=6244 g/mol)

Synthesis of mono-pegylated insulin derivatives 30a and 30b

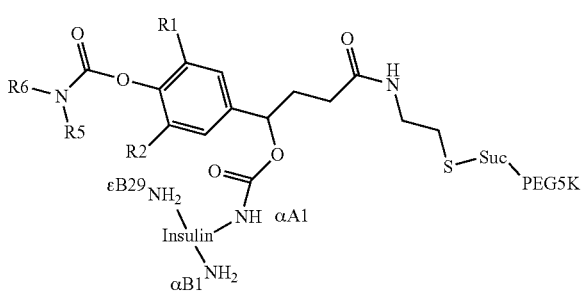

30a R1=Me, R2=H, R5=R6=3-(dimethylamino)propyl
30b R1=R2=R5=Me, R6=2-(dimethylamino)ethyl Insulin derivatives 30a or 30b were synthesized from 29a or 29b, respectively, as described for compound 9a.
30a and 30b: SEC retention time: 19.5 min
Synthesis of a Polymeric Prodrug According to Formula Ia with an Ester-linked Masking Group and a Dendritic Carrier (9h)
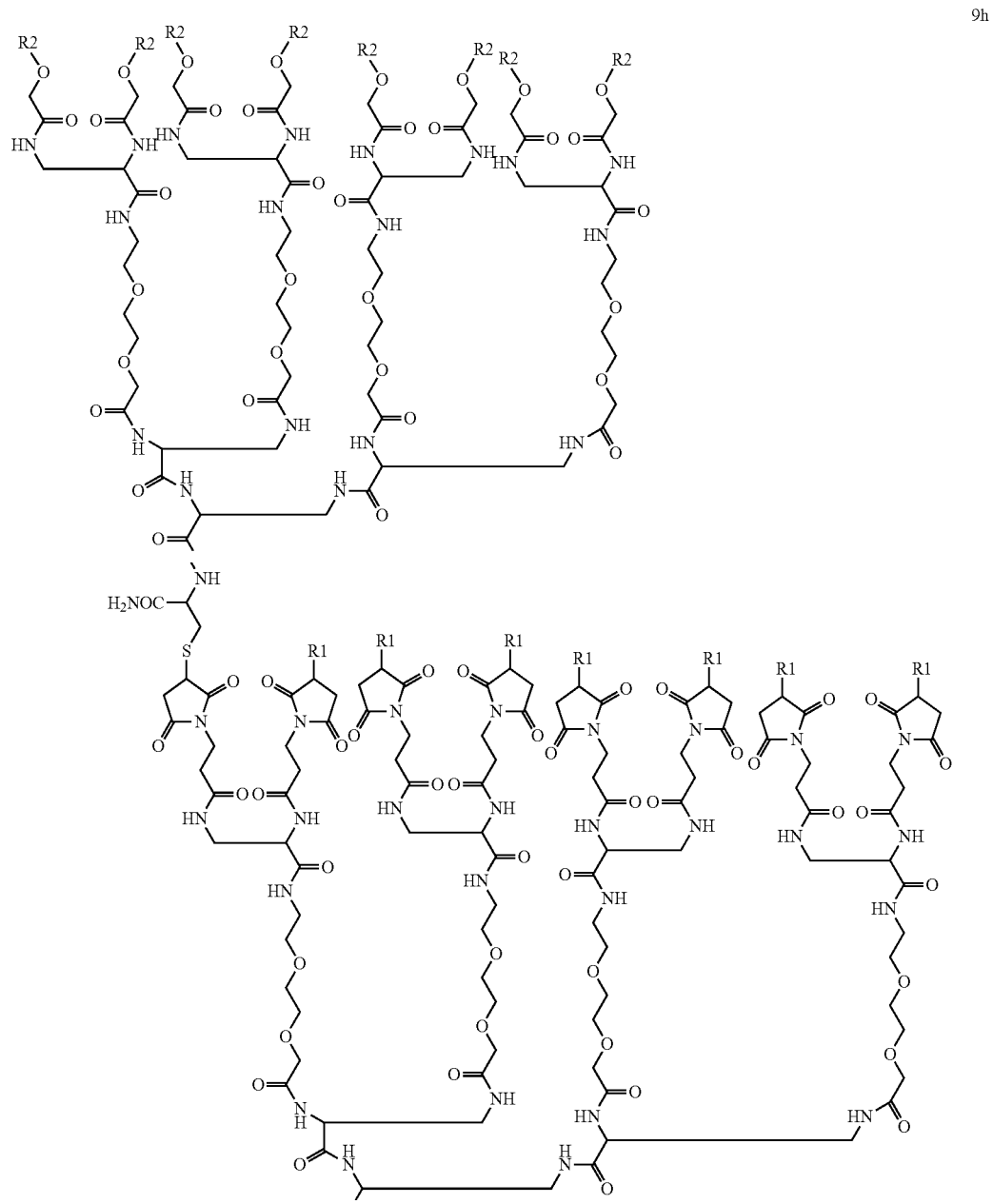
9h

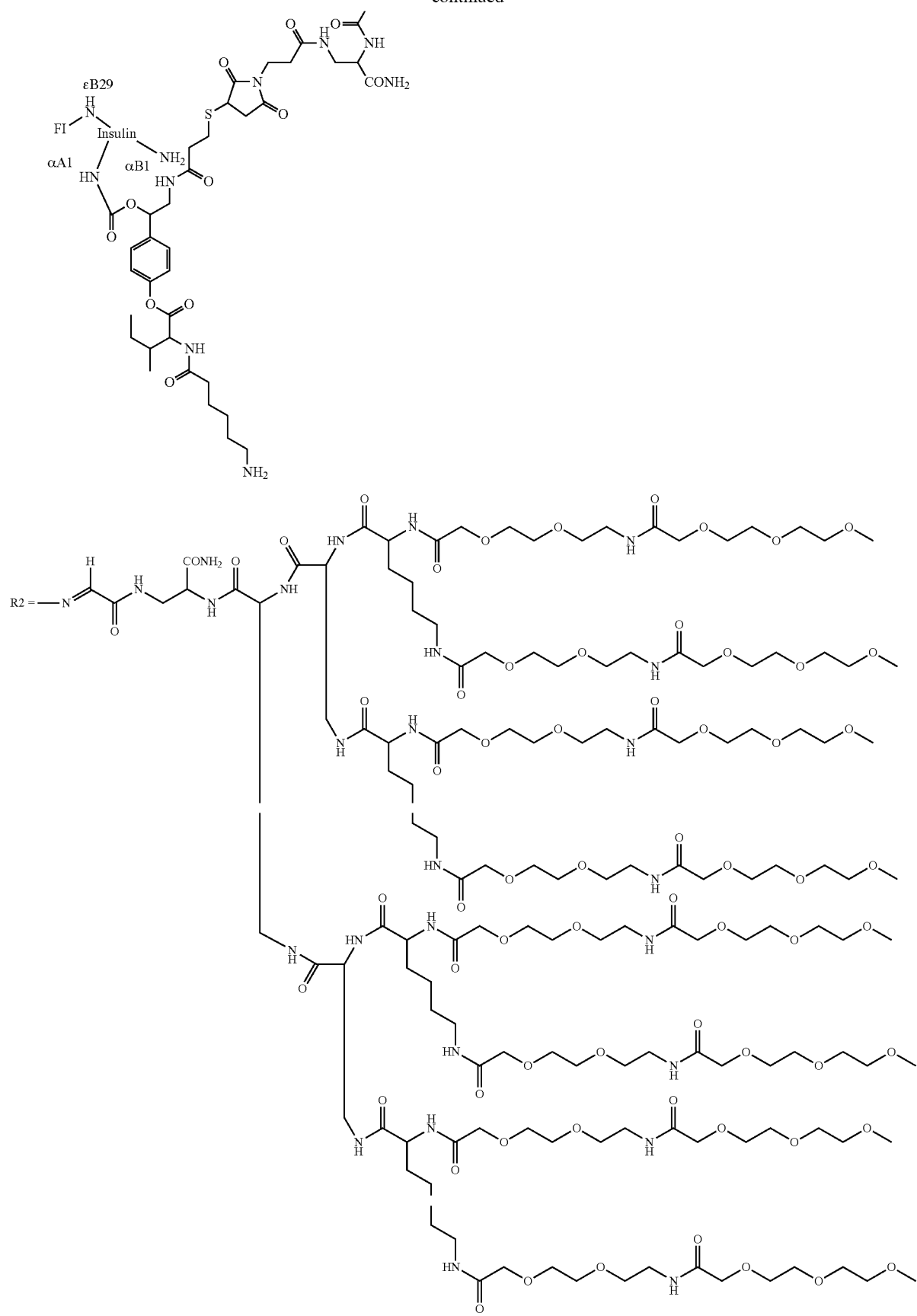

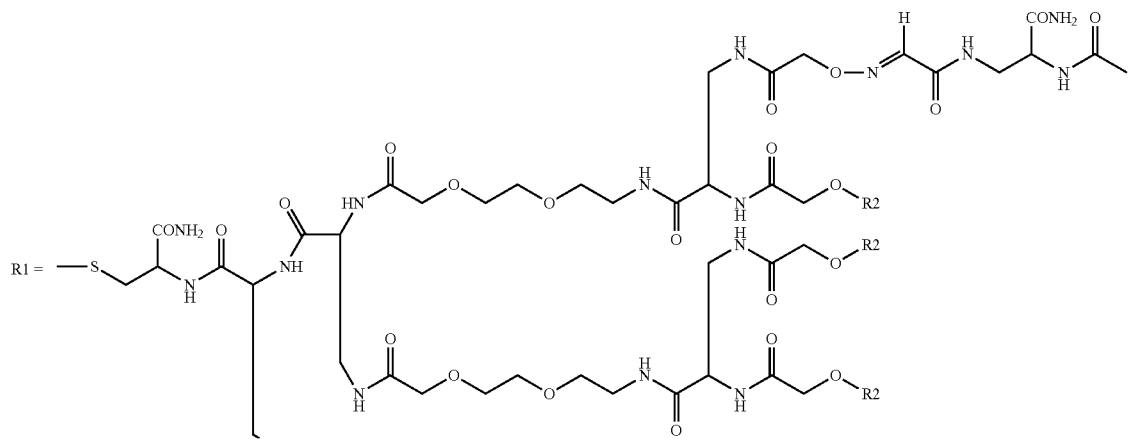
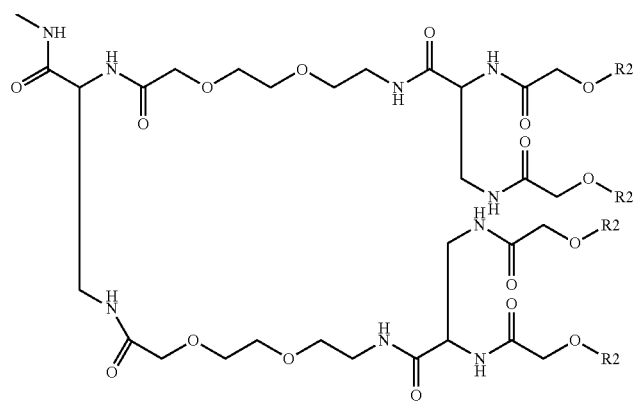
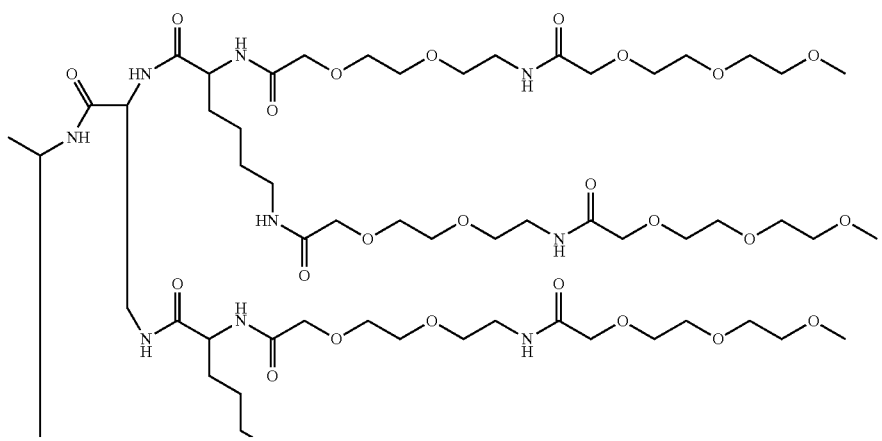

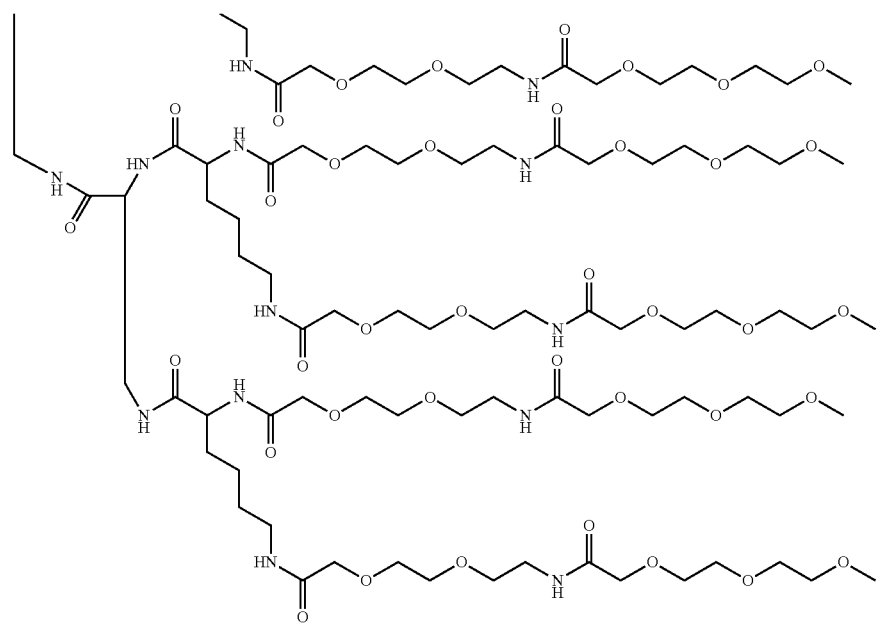
30
Synthesis of Compound 31
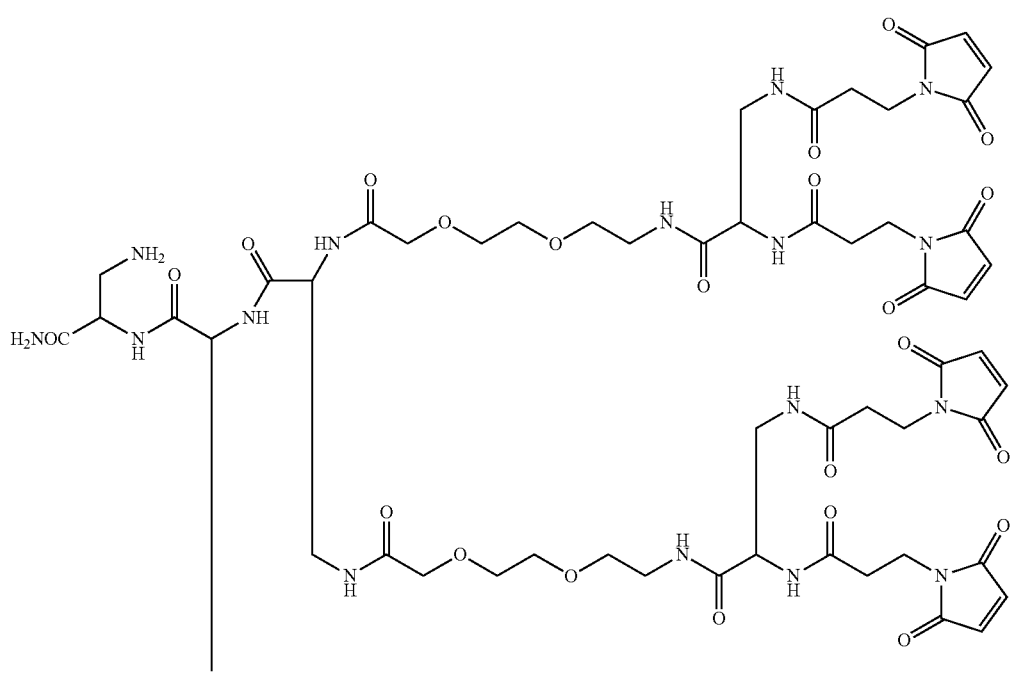
31

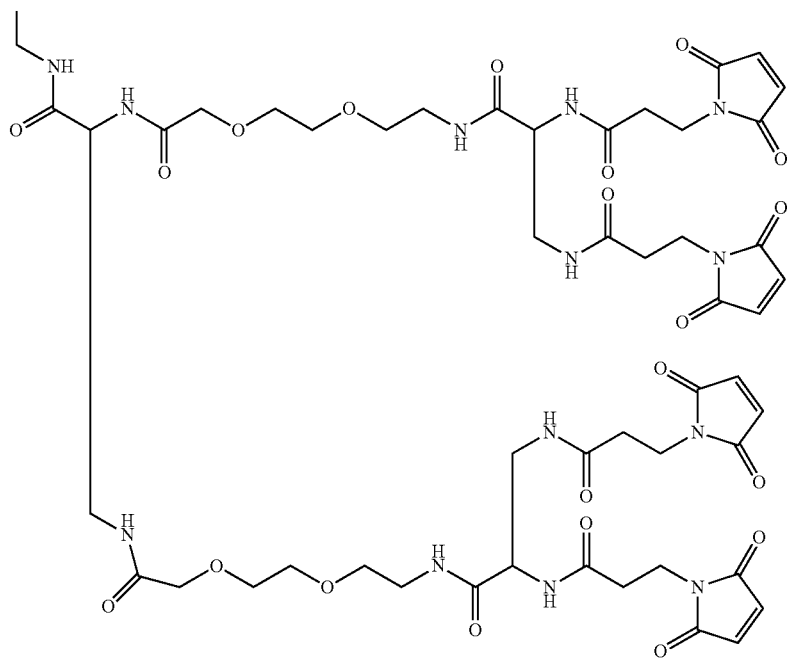

30

31 was obtained according to the standard solid-phase synthesis protocol. The amino acids Fmoc-Dpr(Boc)-OH, Fmoc-Dpr(Fmoc)-OH, Fmoc-Dpr(Fmoc)-OH, Fmoc-Ado-OH, and Fmoc-Dpr(Fmoc)-OH were coupled to NovaSyn TG Sieber amide resin. After final fmoc removal the resin was agitated with 5 eq maleimidopropionic acid and 5 eq DIC in relation to amino groups in DMF for 30 min. 31 was cleaved from resin with TFA/TES/water 95/3/2 (v/v/v). After evaporation of solvent, product 31 was purified by RP-HPLC.

MS: [M+H]$^+$=2494.6 (MW calculated=2495.4 g/mol)

Synthesis of Compound 32

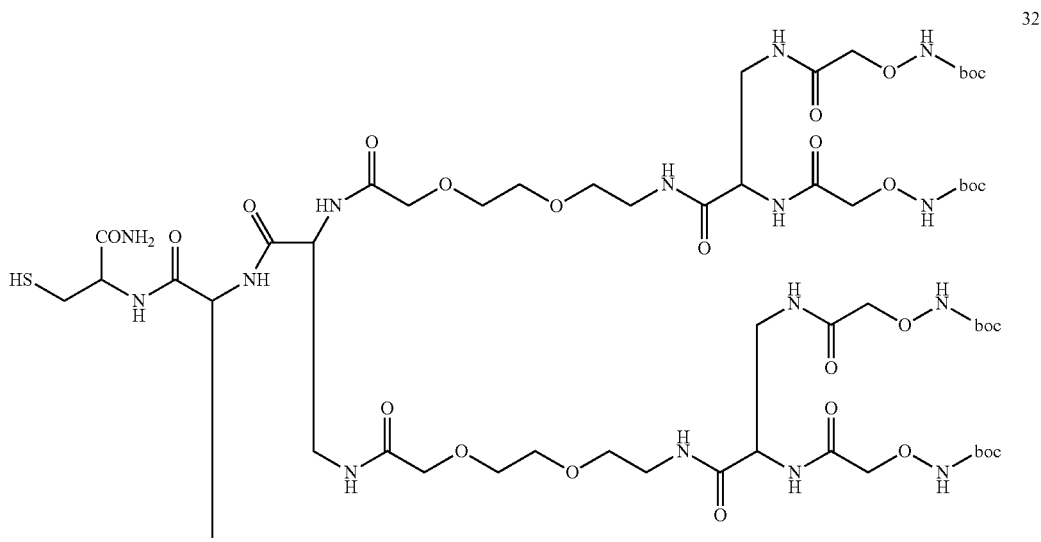

32

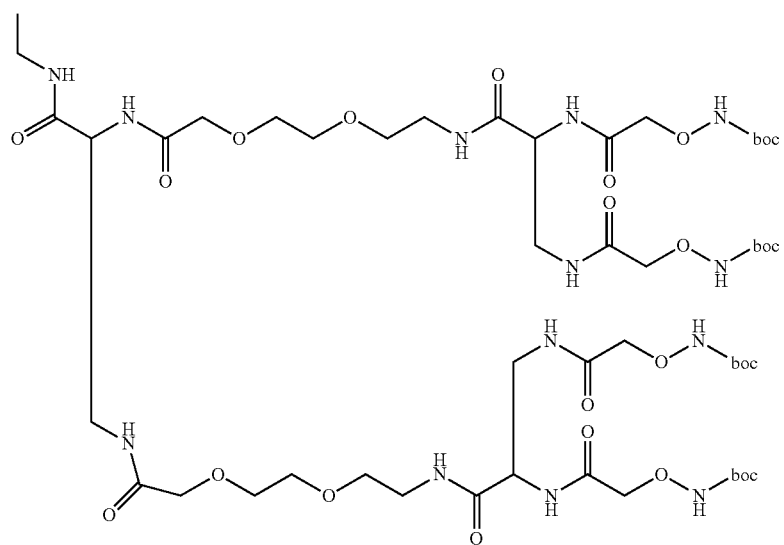

Compound 32 was obtained according to the standard solid-phase synthesis protocol. The amino acids Fmoc-Cys(Mmt)-OH, Fmoc-Dpr(Fmoc)-OH, Fmoc-Dpr(Fmoc)-OH, Fmoc-Ado-OH, and Fmoc-Dpr(Fmoc)-OH were coupled to NovaSynTG Sieber amide resin.

After final fmoc removal the resin was agitated with 3 eq Boc-aminoxyacetic acid, 3 eq DIC, and 3 eq HOBt in relation to amino groups in DMF for 30 min. 32 was cleaved from resin with DCM/TFA/TES 97/1/2 (v/v/v). After addition of 0.8 eq pyridine in relation to the solvent was evaporated and product 32 was purified by RP-HPLC.

MS: $[M+H]^+$=2688.2 g/mol (MW calculated=2688.8 g/mol)

Synthesis of Compound 33

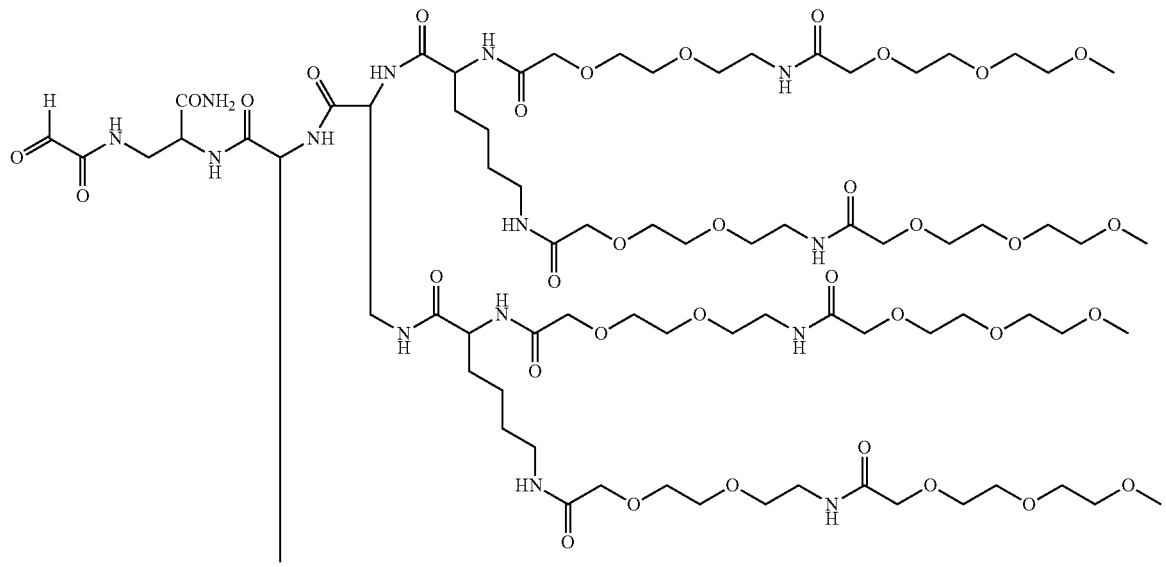

33

-continued

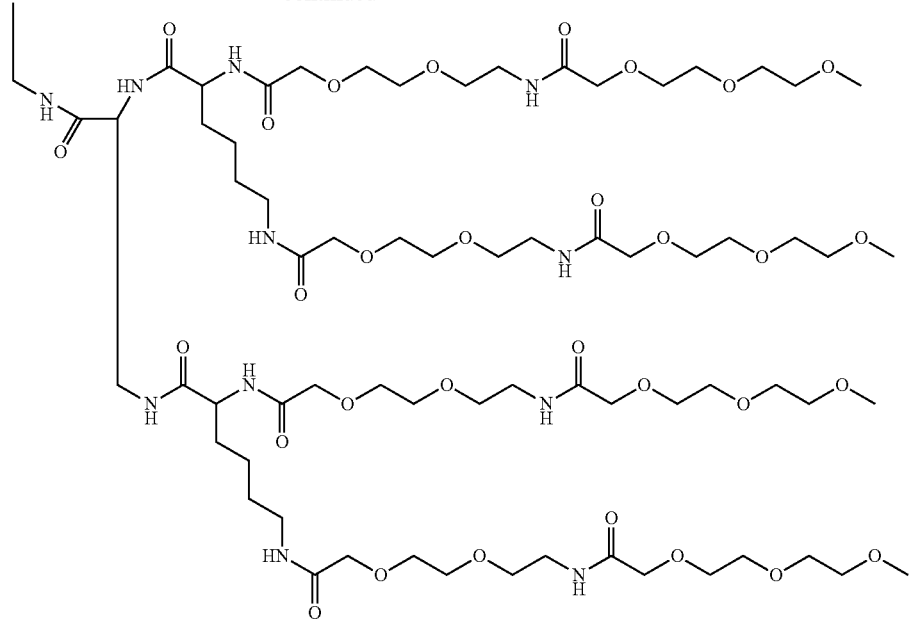

Compound 33 was obtained according to the standard solid-phase synthesis protocol. The amino acids Fmoc-Dpr(ivDde)-OH, Fmoc-Dpr(Fmoc)-OH, Fmoc-Dpr(Fmoc)-Fmoc-Lys(Fmoc)-OH, and Fmoc-Ado-OH were coupled to NovaSyn TG Sieber amide resin.

After final fmoc removal the resin was agitated with 3 eq 3,6,9-trioxadecanoic acid, 3 eq PyBOP, and 6 eq DIEA in relation to amino groups in DMF for 60 min.

To cleave the ivDde protecting group, the resin was treated three times with 2% hydrazine in DMF. Alter washing, 3 eq Fmoc-Ser-OH was coupled with 3 eq DIC and 3 eq HOBt for 30 min. After final fmoc removal resin was washed and the product was cleaved from resin with DCM/TFA/TES 88/10/2 (v/v/v). Solvent was evaporated and the residue was oxidized with 10 eq sodium periodate in 3/2 (v/v) 0.1 M sodium phosphate pH 7/acetonitrile for 15 min to yield 33. Product 33 was purified by RP-HPLC and lyophilized.

MS: $[M+H]^+$=3372.1 g/mol (3372.8 g/mol)

Synthesis of Compound 34

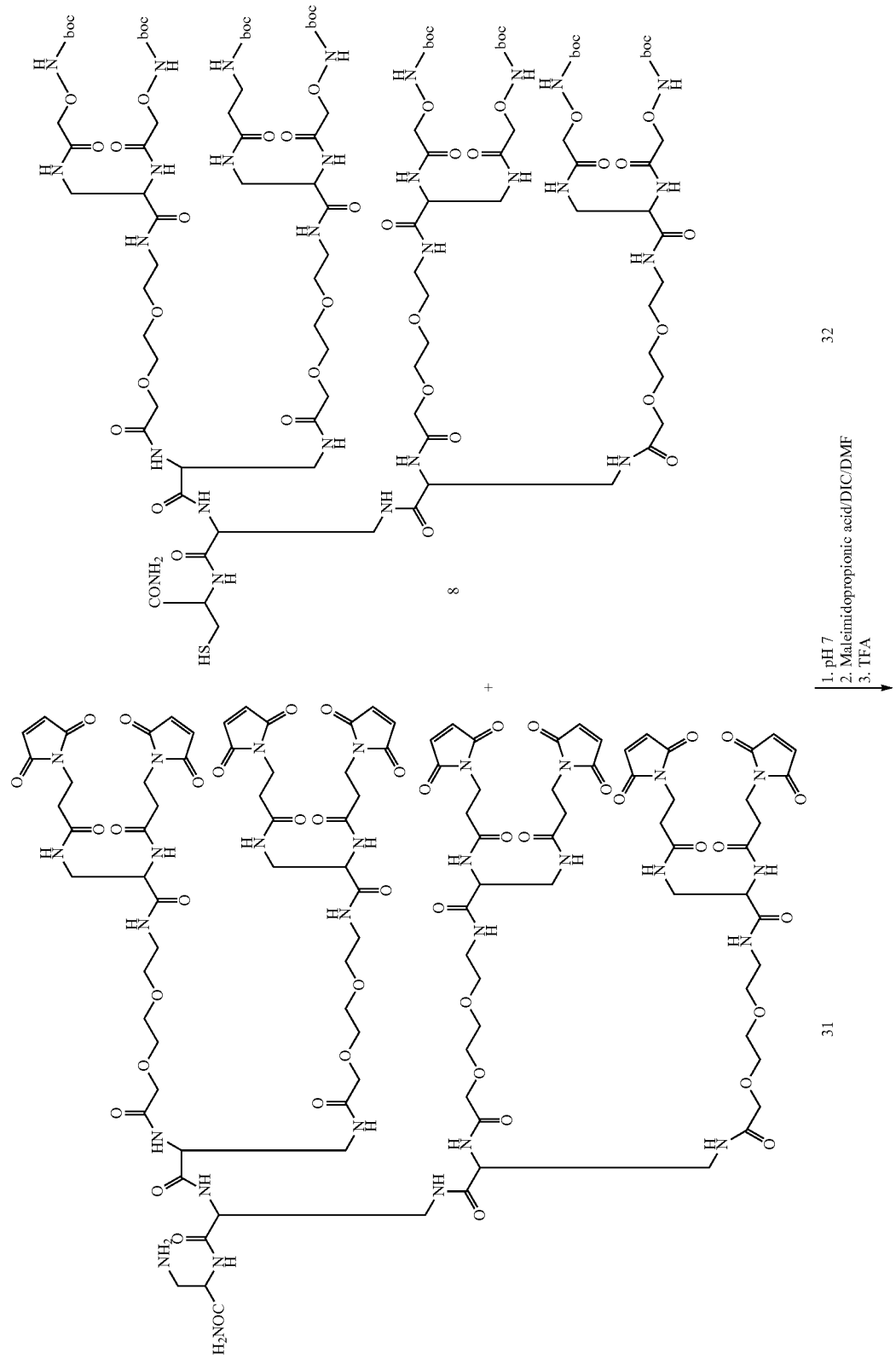

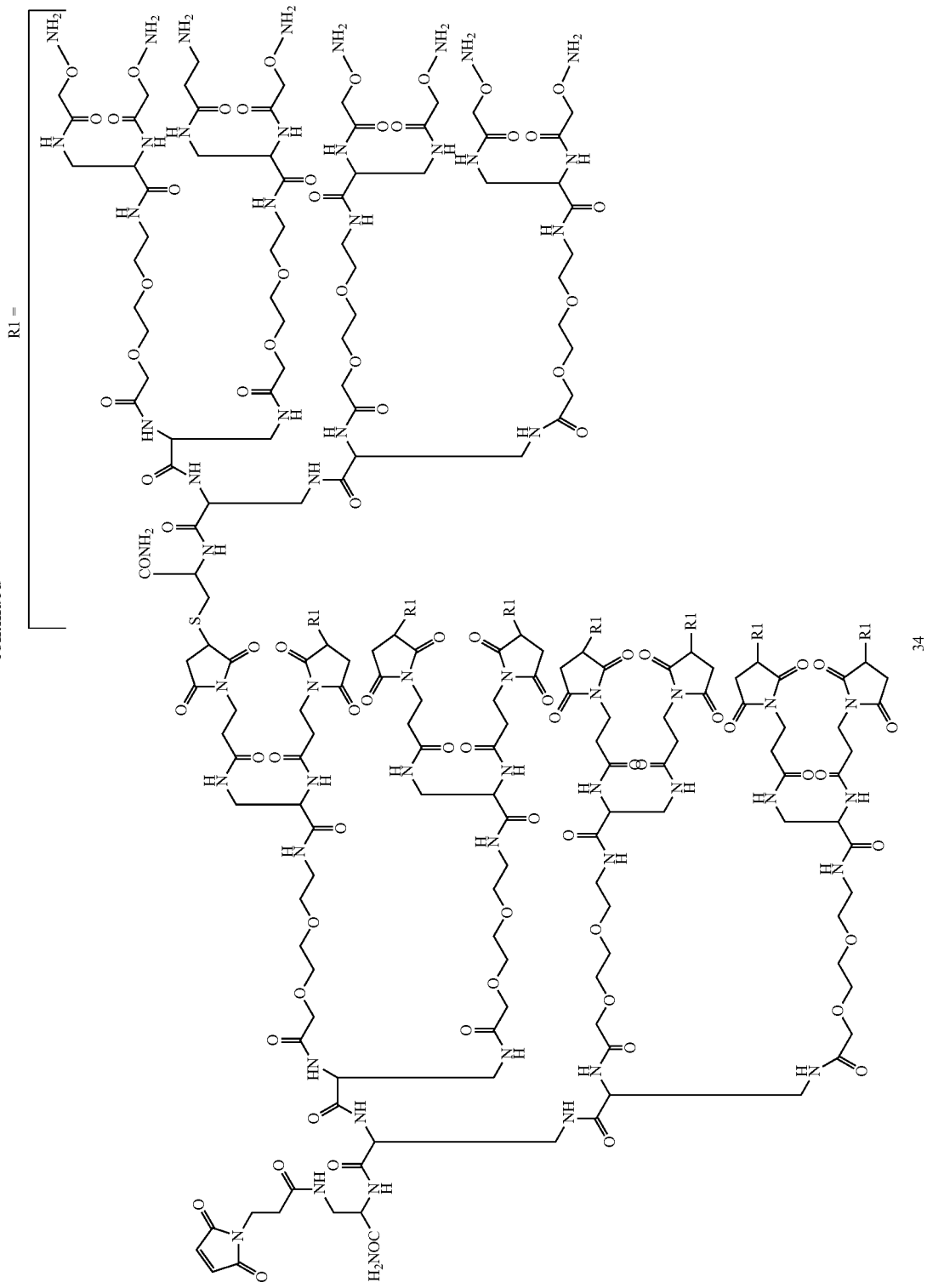

6 mg (2.4 µmol) of compound 31 were dissolved in 1 ml 2/1 (v/v) acetonitrile/0.1 M sodium phosphate buffer pH 7 and 65 mg (24.2 µmol) of compound 32 were added. The solution was stirred at room temperature for 2 h and then the product purified by RP-HPLC and lyophilized (yield: 45 mg (78%)).

The lyophilized product (45 mg) was dissolved in 0.5 ml DMF and 10 µl DIEA were added. 5 mg (30 µmol) 3-maleimidopropionic acid and 4.7 µl (30 µmol) DIC in 150 µl to DMF were added and the reaction mixture was stirred at roam temperature for 20 min, the product purified by RP-HPLC and lyophilized.

The lyophilized product was incubated for 10 min in 95/5 (v/v) TFA/water and then the solvent was removed in a stream of nitrogen. Product 34 was purified by RP-HPLC and lyophilized (overall yield for all three steps: 20 mg (47%)).

MS: 17700-18200 (broad peak) (MW calculated=17749 g/mol)

Synthesis of Compound 9h 1.5 mg (225 nmol) 8g and 5 mg (280 nmol) 34 were mixed, dissolved in 300 µl 2/1 (v/v) 0.1 M sodium phosphate buffer pH 7/acetonitrile and incubated for 15 min at room temperature. The product was purified by RP-HPLC and lyophilized. (yield 4 mg, 160 nmol, 70%)

The lyophilized product was dissolved in 200 µl 0.1 M sodium citrate buffer pH 1.5 and 69 mg (20.5 µmol) 33 in 200 µl 2/1 (v/v) acetonitrile/sodium citrate buffer pH 1.5 were added. The mixture was stirred at room temperature for 24 h and product 9h was purified by size exclusion chromatography (column: Superdex 200, buffer: 10 mM HEPES pH 7.4, 0.005% Tween-20, 3 mM EDTA, flow rate: 0.75 ml/main)

SEC elution time: 15 min

Synthesis of Compound 37a

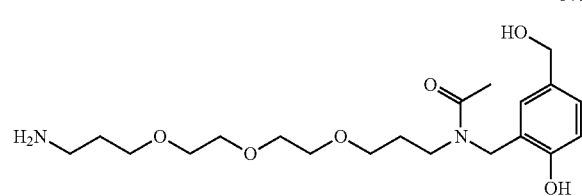

250 mg (0.35 mmol) 2-chlorotrityl chloride resin (loading 1.4 mmol/g) was incubated for 1.5 h with 308 mg (4 eq., 1.4 mmol) 4,7,10-trioxatridecane-1,13-diamine in 4 ml DCM to yield 35a. The resin was washed with DCM and dried. 107 mg (0.7 mmol) HOBt, 110 µl (0.7 mmol) DIC, and 150 mg (0.9 mmol) 5-formyl salicylic acid in 3 ml DMF were added and the resulting suspension was stirred for 1 h at RT to yield 36a. After washing with DCM and THF, the resin was suspended in 6 ml THF and 3 ml (3 mmol) BH₃ THF (1 M in THF, 8.5 eq.) were added dropwise. The reaction mixture was stirred for 18 h at 45° C. under nitrogen atmosphere. After cooling 4 ml THF, 0.8 ml DIEA and 1.6 ml MeOH were added successively. 210 mg (0.84 mmol) I₂ (as a concentrated THF solution) were added and the suspension was stirred for 1 h. The resin was repeatedly washed (three times each) with THF, DMF, MeOH, and DCM. The dried resin was reacted with 107 mg (0.7 mmol) HOBt, 110 µl (0.7 mmol) DIC, and 55 µL (0.9 mmol) AcOH in 3 ml DMF for 1 h. After washing of the resin with DMF and DCM compound 37a was cleaved from resin with 2/1 (v/v) HFIP/DCM (two times for 30 min). The volatile components were evaporated and the product 37a was used in the following step without further purification.

37a: Yield 29 mg (20%) as TFA salt

MS [M+Na]⁺=421.4 (MW+Na calculated=421.5 g/mol)

Synthesis of Compound 38

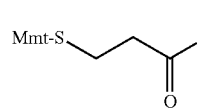

24 mg (0.06 mmol) 37a, 31 mg (0.06 mmol) PyBOP, 32 µl (0.18 mmol) DIEA, and 23 mg (0.06 mmol) 2 in 0.5 ml DMF were reacted for 50 min at room temperature. After addition of 50 µl acetic acid product 38 was purified by RP-HPLC.

38: Yield 7 mg (15%)

MS [M+Na]⁺=781.3 (MW+Na calculated=781.6 g/mol)

Synthesis of Compound 39

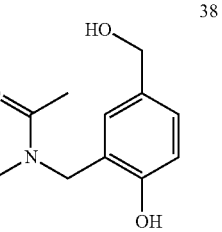

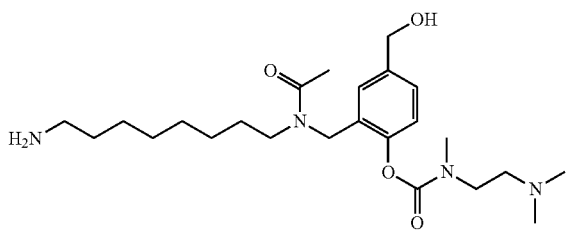

300 mg (0.42 mmol) 2-chlorotrityl chloride resin (loading 1.4 mmol/g) was incubated for 1.5 h with 245 mg (4 eq., 1.7 mmol) 1,8-diaminooctane in 4 ml DCM to yield 35b. The resin was washed with DCM and dried. 107 mg (0.7 mmol) HOBT, 110 µl (0.7 mmol) DIC, and 150 mg (0.9 mmol) 5-formyl salicylic acid in 3 ml DMF were added and the resulting suspension was stirred for 1 h at RT to yield 36b. After washing with DCM and THF, the resin was suspended in 6 ml THF and 3 ml (3 mmol) BH₃ THF (1 M in THF) were added dropwise. The reaction mixture was stirred for 18 h at 45° C. under nitrogen atmosphere. After cooling 4 ml THF, 0.8 ml DIEA and 1.6 ml MeOH were added successively. 210 mg (0.84 mmol) I₂ (as a concentrated THF solution) were added and the suspension was stirred for 1 h. The resin was repeatedly washed (three times each) with THF, DMF, MeOH, and DCM. The dried resin was reacted with 107 mg (0.7 mmol) HOBT, 110 µl (0.7 mmol) DIC, and 55 µL (0.9 mmol) AcOH in 3 ml DMF for 1 h. After washing of the resin with DMF and DCM compound 37b, 78 mg (0.39 mmol) p-nitrophenylchloroformate, and 210 µl (1.2 mmol) DIEA in 1/1 (v/v) THF/DCM were reacted for 30 min at RT. The separated resin was suspended in 1/1 (v/v) THF/DCM and 210 µl (1.2 mmol) N,N,N'-trimethylethylendiamine were added. The resulting suspension was stirred for 25 min at RT. The resin was separated and washed with DCM. Product 39 was cleaved from resin with 2/1 (v/v) HFIP/DCM (two times for 30 min). The volatile components were evaporated and the product 39 was purified by HPLC.

39: Yield 16 mg (8%) as TFA salt

MS [M+Na]⁺=473.5 (MW+Na calculated=473.3 g/mol)

Synthesis of Compound 40a

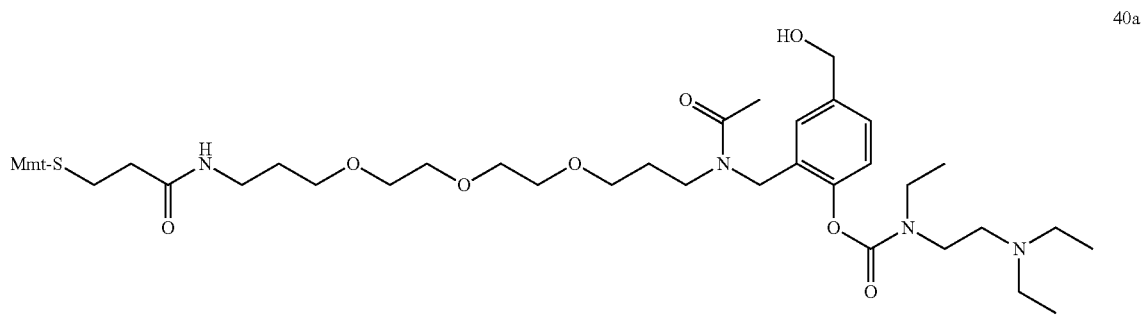

38 (7 mg, 9 μmol) was dissolved in 200 μl of dry THF, p-Nitrophenylchloroformate (2.0 mg, 10 μmol) and DIEA (4.4 μl, 25 μmol) were added and the mixture was stirred for 30 min at RT. N,N,N'-Triethylethylenediamine (15b) (18 μl, 0.1 mmol) was added and stirring was continued for 30 min. The solvent was removed in vacuo, 10 μl of AcOH were added and 40a was purified by RP-HPLC.

40a: Yield 1 mg (11%) as TFA salt

MS [M+Na]$^+$=951.1 (MW+Na calculated=951.8 g/mol)

Synthesis of Compound 40b

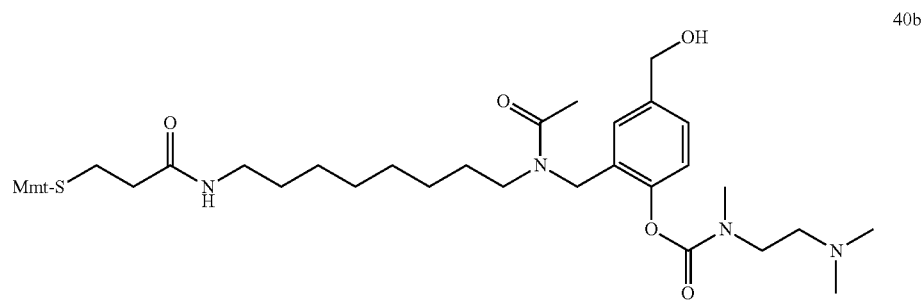

15 mg (33 μmol) 39, 18 mg (33 μmol) PyBOP, 23 μl (0.13 mmol) DIEA, and 13 mg (35 μmol) 2 in 0.5 ml DMF were reacted for 45 min at room temperature. After addition of 50 μl acetic acid product 40 was purified by RP-HPLC.

40b: Yield 10 mg (37%) as TFA salt

MS [M+H]$^+$=811.5 (MW+Na calculated=810.5 g/mol)

Synthesis of Compound 41a and 41b

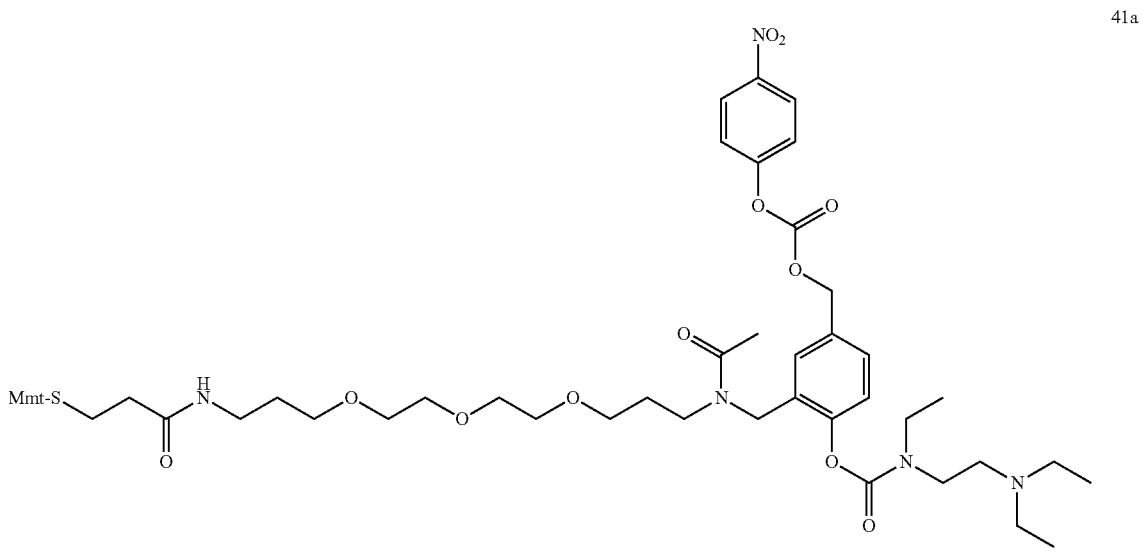

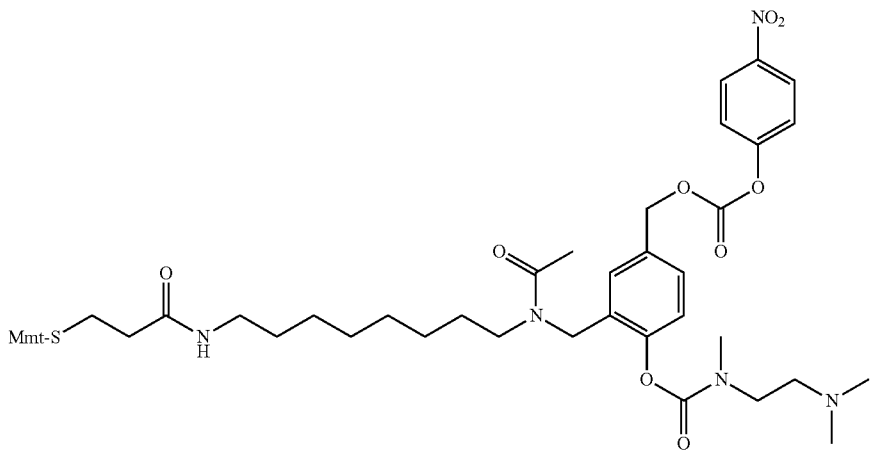
Carbonate 41a or 41b was synthesized from 40a or 40b as described for compound 7a
41a: Yield 0.4 mg as TFA salt
MS [M+Na]$^+$=1116.8 (MW+Na calculated=1116.9 g/mol)
41b: Yield 2 mg (16%) as TFA salt
MS [M+H]$^+$=976.8 (MW calculated=975.8 g/mol)
Synthesis of Compound 42
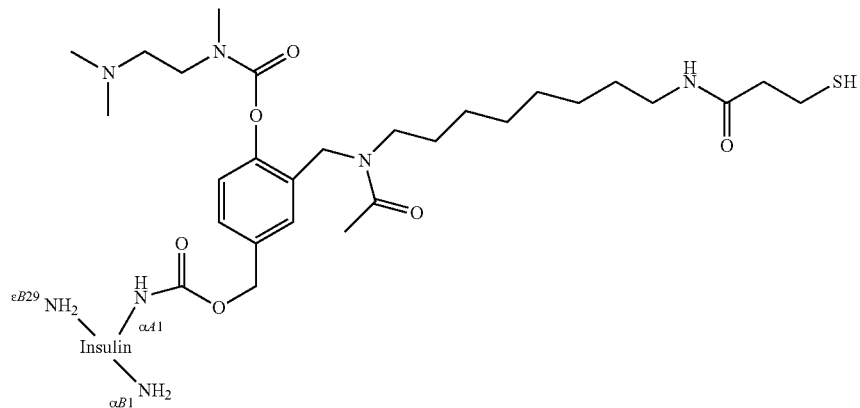
Insulin derivative 42 was synthesized from 41b as described for compound 8a.
42 MS [M+3H]$^{3+}$=2124.5 [M+4H]$^{4+}$=1594.6 (MW calculated=6371 g/mol)
Synthesis of Compound 43
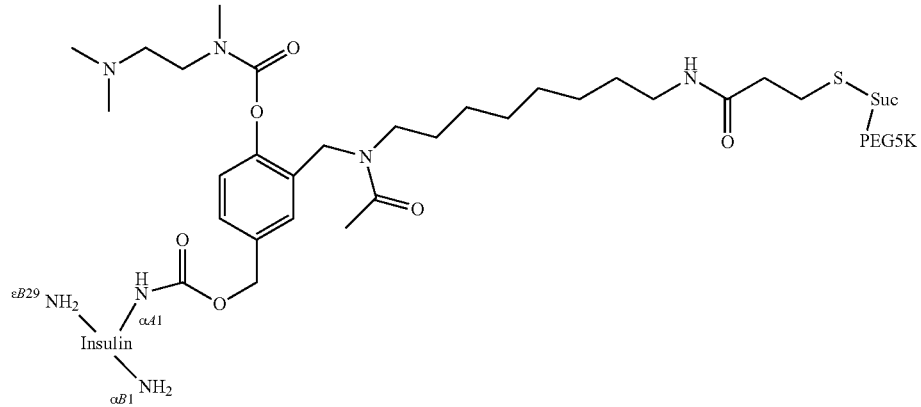

Insulin derivative 43 was synthesized from 42 as described for compound 9a.
43: SEC retention time: 18.0 min
Synthesis of Rh-insulin Loaded PEGA Hydrogel 45

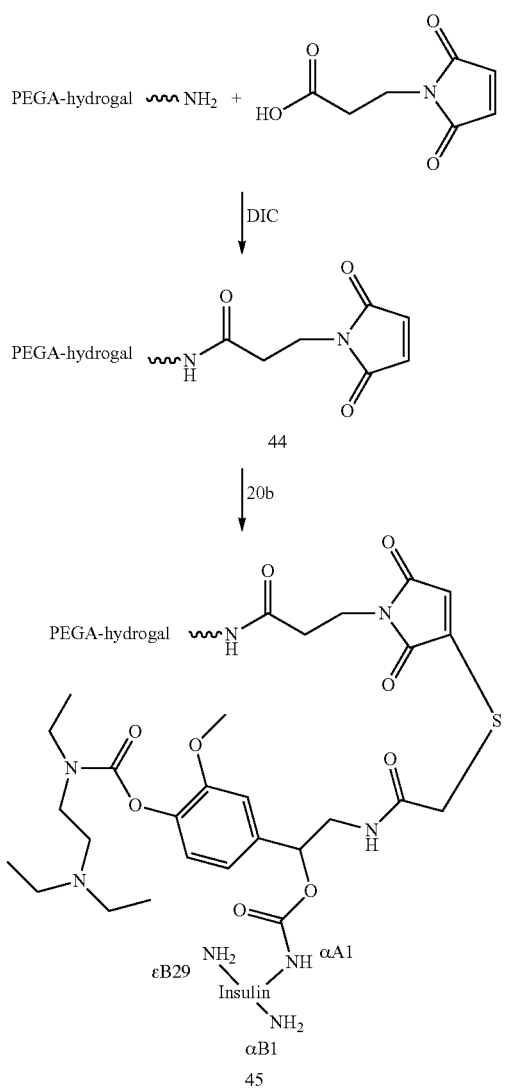

Maleimide Derivatization of Polyacrylamide Based Hydrogel (PEGA):

NH$_2$-PEGA hydrogel beads with 0.4 mmol/g loading and 150-300 μm bead size were purchased from Novabiochem.

2.5 g methanol-wet NH$_2$-PEGA-hydrogel (0.4 mmol/g NH$_2$-loading) was weighed into a syringe equipped with a polypropylene frit. Maleimide loading was adjusted by acylation employing a mixture of activated maleimidopropionic acid and acetic acid as described in the following. The hydrogel was washed 5 times with DMF and reacted with 13.5 mg (0.08 mmol) 3-maleimidopropionic acid, 115.2 μl (1.92 mmol) acetic acid and 313 μl (2 mmol) DIC in 4 ml DMF for 30 min. The maleimide derivatized hydrogel 44 was washed 10 times with DMF and DCM and finally with acetonitrile.

30 mg of maleimide derivatized resin 44 (loading 16 μmol/g) was reacted with 3 mg of compound 20b (480 nmol, 1.06 eq) in 600 μl 20/80 (v/v) acetonitrile/50 mM phosphate buffer (pH 7.4) for 10 min to give rh-insulin loaded hydrogel 45. The hydrogel 45 was washed 5 times with 50/50 (v/v) acetonitrile/water and three times with acetonitrile and dried under vacuum.

Synthesis of Rh-insulin Carbohydrate-based Hydrogel 46

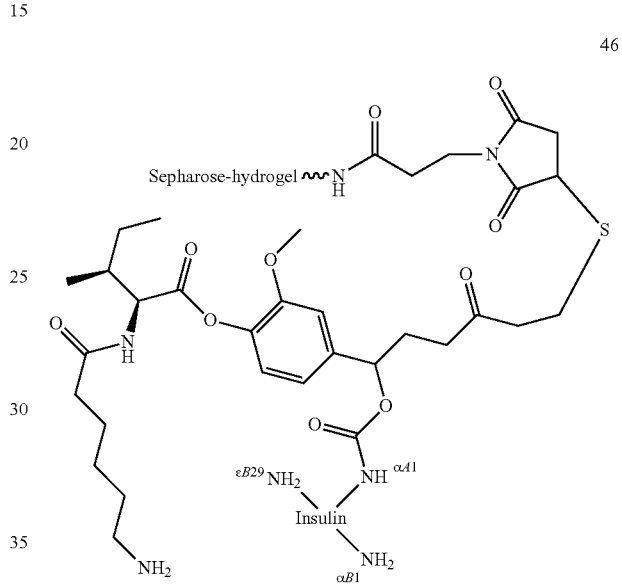

NHS-activated "Sepharose 4 Fast Flow" hydrogel beads (chemically crosslinked agarose, crosslinker epichlorhydrin) were purchased from Amersham.

1.5 g ethanol-wet Sepharose hydrogel (150 mg dry hydrogel) was weighed into a syringe equipped with a polypropylene frit and reacted with 1 M 4,7,10-trioxatridecane-1,13-diamine in DMF for 30 min. After 5 washing steps with DMF, hydrogel was reacted with 8.5 mg (0.05 mmol) 3-maleimidopropionic acid, 57 μl (0.95 mmol) acetic acid, 151 mg (1 mmol) HOBt and 158 μl (1 mmol) DIC in 4 ml DMF for 30 min to give maleimide derivatized hydrogel. The hydrogel was washed 10 times with DMF and finally with acetonitrile. 1.5 mg 8c was dissolved in 25/75 (v/v) acetonitrile/50 mM phosphate buffer pH 7.4 and reacted with 10.8 mg maleimide derivatized hydrogel for 10 min The rh-insulin loaded hydrogel 46 was washed five times with 50/50 (v/v) acetonitrile/water and three times with acetonitrile and dried under vacuum.

Synthesis Scheme of Fuorescein-Insulin-rHSA (50)

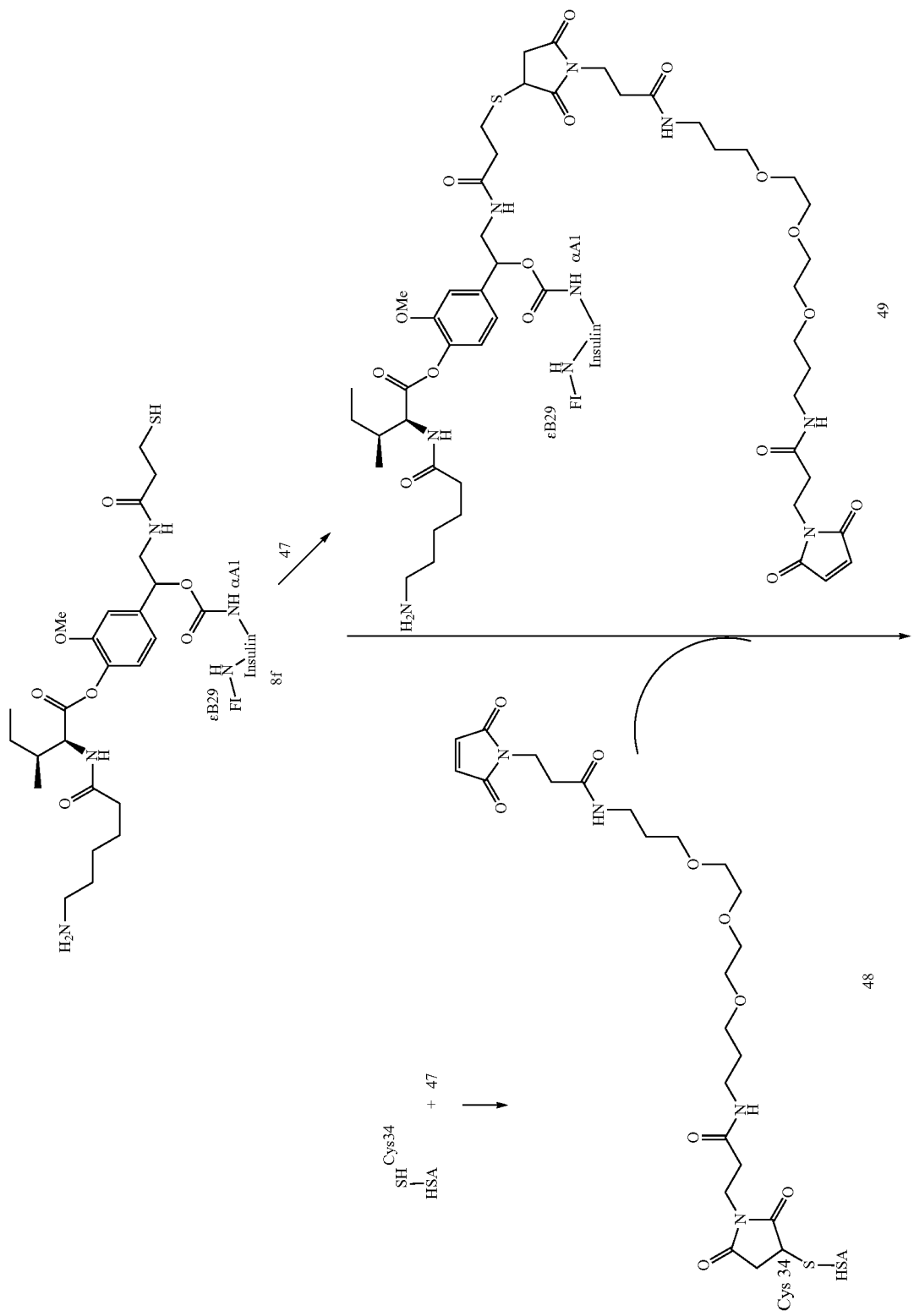

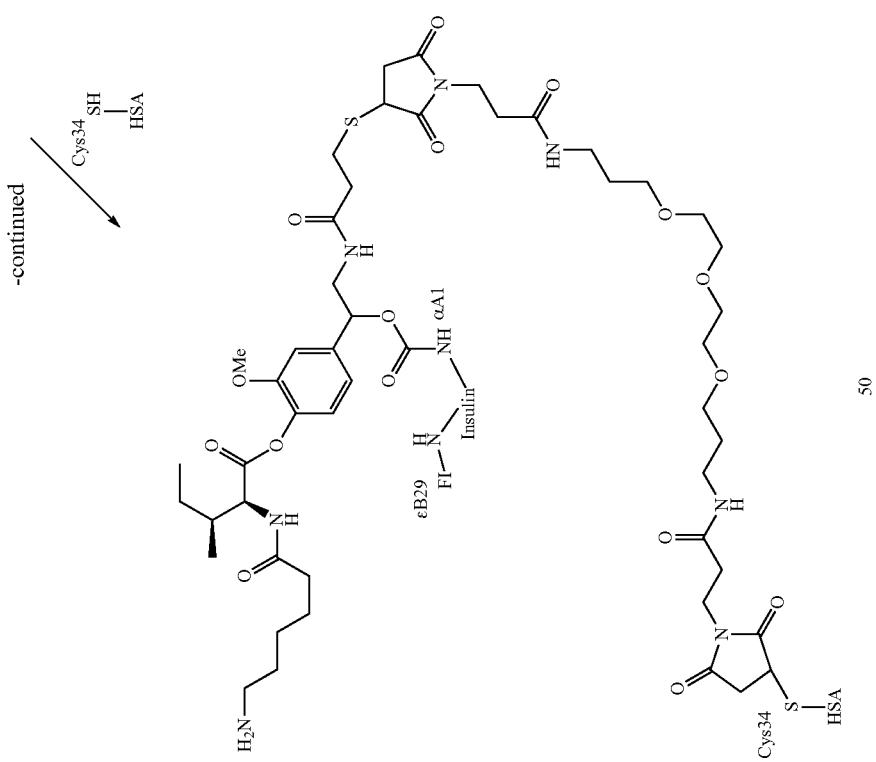

Synthesis of Bismaleimide 47

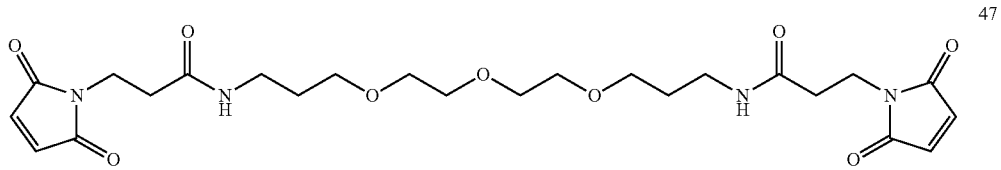 [SMILES: O=C(CCN1C(=O)C=CC1=O)NCCCOCCOCCOCCCNC(=O)CCN1C(=O)C=CC1=O]

3-Maleimido-propionic acid (92 mg, 0.54 mmol) in 200 µl DMF was reacted with DIC (78 µl, 0.50 mmol) at RT for 15 min 4,7,10-Trioxa-tridecan-1,13-diamine (43.5 µl, 0.20 mmol) was added and the mixture was stirred for 30 min at RT.

After addition of 800 µl 1/4 (v/v) acetic acid/water 47 was purified by RP-HPLC.

47: yield 23 mg (22%)

MS [M+Na]$^+$=545.5 (MW+Na calculated=545.6 g/mol)

Synthesis of rHSA-maleimide (48)

66.5 µl 3 mM rHSA solution in 145 mM NaCl, 32 mM sodium octanoate, 0.0015% Tween-80 was mixed with 66.5 µl 0.5 M phosphate buffer pH 7.0, 0.41 mg bismaleimide 47 (0.8 µmol) were added and the mixture was reacted for 15 min at RT. Compound 48 was purified by SEC (column: Superdex 200, flow rate: 0.75 ml/min) using 10 mM HEPES buffer pH 7.4, 150 mM NaCl, 3 mM EDTA, and 0.005% Tween as mobile phase. (Yield: 2.6 ml 77.5 µM 48)

SEC retention time: 17.1 min (280 nm)

ESI-MS=66988 (MW calculated=66984 g/mol)

Synthesis of Fluorescein-insulin-linker-maleimide (49)

40 µl of 2.4 mM bismaleimide 47 in 1/1 (v/v) acetonitrile/water (96 nmol) were mixed with 40 µl 0.5 M sodium borate buffer pH 5.8. 24 nmol 8f in 16.8 µl 1/1 (v/v) acetonitrile/water were added and the mixture was incubated for 10 min at RT 5 µl AcOH were added and 49 was purified by RP-HPLC.

ESI-MS=7211 (MW calculated=7211 g/mol)

Synthesis of Fluorescein-Insulin-Linker-rHSA 50
a) from 49 and rHSA
b) from 48 and 8f a)
30 µl of 80 µM 49 in 1/1 (v/v) acetonitrile/water (2.4 nmol) were mixed with 70 µl 0.25 M sodium phosphate buffer pH 6.4. 8 µl 3 mM rHSA in 145 mM NaCl 32 mM sodium octanoate, 0.0015% Tween-80, (24 nmol) was added and the mixture was incubated at RT for 20 min.

Compound 50 was purified by SEC (column: Superdex 200, flow rate: 0.75 ml/min) using 10 mM HEPES buffer pH 7.4, 150 mM NaCl, 3 mM EDTA, and 0.005% Tween as mobile phase.

SEC retention time: 17.3 min. (500 nm)

ESI-MS=73676 (MW calculated=73673 g/mol)

b)
SEC eluate of rHSA-maleimide 48 (241 µl, 77.5 µM, 18.7 nmol) was mixed with 20 µl 0.5 M sodium borate buffer pH 5.8. 14 µl 1.41 mM 8f (19.6 nmol) in 1/1 (v/v) acetonitrile/water were added and the mixture was incubated at RT for 10 min, 1.2 µl 48.5 mM 3-maleimido propionic acid (58 nmol) in 1/1 (v/v) acetonitrile/water were added and compound 50 was purified by SEC (column: Superdex 200, flow rate: 0.75 ml/min) using 10 mM HEPES buffer pH 7.4, 150 mM NaCl, 3 mM EDTA, and 0.005% Tween as mobile phase.

SEC retention time: 17.1 min (500 nm)

ESI-MS=73698 (MW calculated=73673 g/mol)

Synthesis Scheme of rHSA-linker-GLP-1 53a and 53b

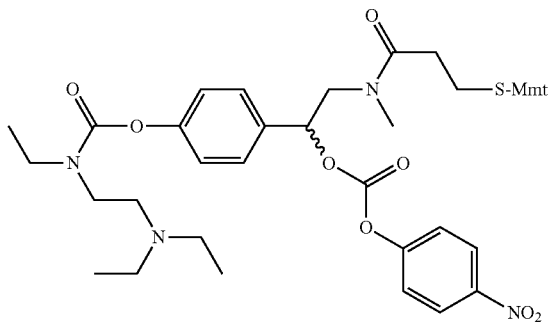

19i

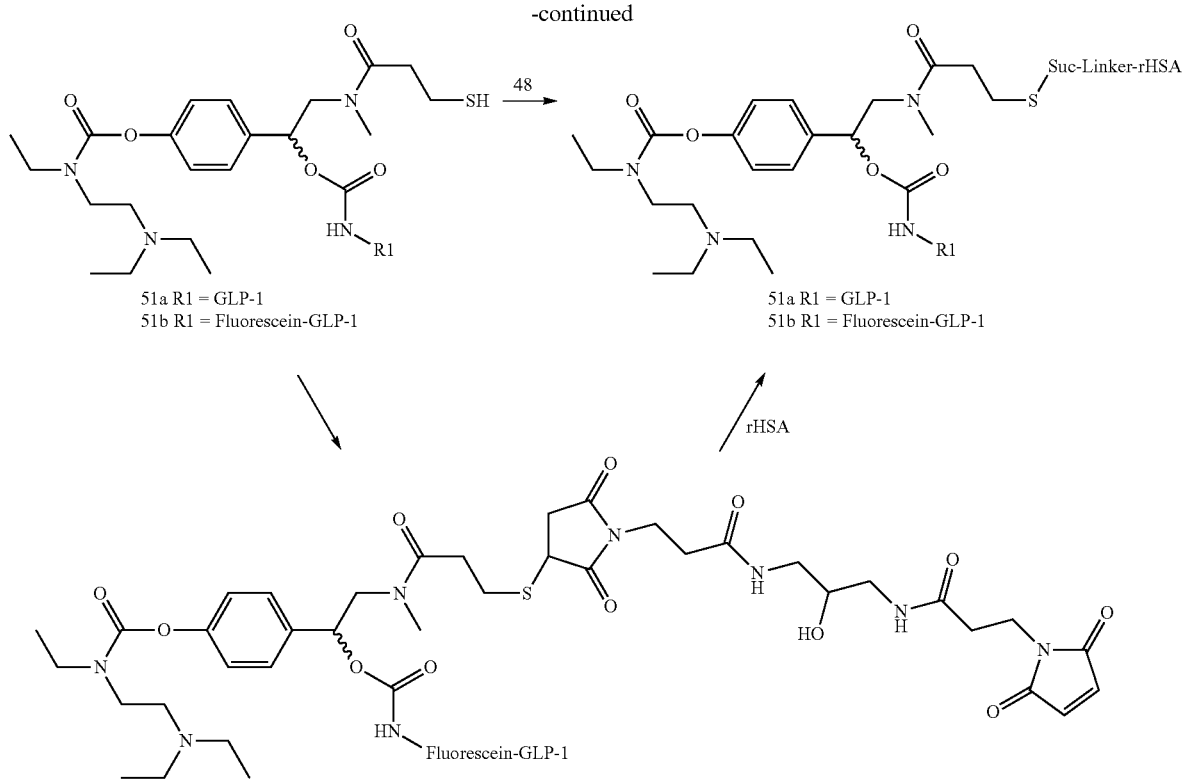

52

Synthesis of 51a

GLP (7-36) (sequence: HAEGTFTSDVS-SYLEGQAAKEFIAWLVKGR-amide) was synthesized on Rink-amide resin employing fmoc-strategy (Specialty Peptide Laboratories, Heidelberg, Gel litany). N-terminal fmoc-protecting group was removed and the resin was washed with DCM and dried. 118 mg resin (0.11 mmol/g, 13.2 µmol) was suspended in a solution of 50 mg 19i (53 µmol) in 750 µl dry DMSO and 22.4 µl DIEA. 2.1 µl pyridine was added and the mixture was shaken for 48 h at RT. After washing the resin 6 times each with DMF and DCM, cleavage of the peptide from resin and removal of protecting groups was achieved with 96/2/2 (v/v/v) TFA/triethylsilane/water. Volatiles were removed under nitrogen flow and 51a was purified by RP-HPLC and lyophilized.

51a: Yield 4.6 mg (9%)
MS: $[M+3H]^{3+}=1251.0$ (MW calculated=3750.3 g/mol)

Synthesis of 51b

Lys28 ivDde side chain protected GLP(7-36) (sequence: HAEGTFTSDVSSYLEGQAAKEFIAWLVK(ivDde)GR-amide) was synthesized on Rink-amide resin employing fmoc-strategy (Specialty Peptide Laboratories, Heidelberg, Germany). N-terminal fmoc-protecting group was removed and the resin was washed with DCM and dried. 50 mg resin (0.11 mmol/g, 5.5 µmol) was suspended in a solution of 25 mg 19i (26 µmol) in 400 µl dry DMSO and 11.2 µl DIEA. 1.1 µl pyridine was added and the mixture was shaken for 48 h at RT. After washing the resin six times with DMF the ivDde protecting group was cleaved by incubating the resin 3 times with 5% hydrazine in DMF for 20 min. Fmoc-8-amino, 3,6-dioxaoctanoic acid was coupled according to the standard coupling cycle. Fmoc protecting group was removed and carboxy-fluorescein was coupled by incubating the resin with 8 mg 5-(and -6)-carboxy fluorescein succinimidyl ester and 2 µl DIEA for 60 min. Resin was washed six times each with DMF and DCM. Cleavage of the peptide from resin and removal of protecting groups was achieved with 96/2/2 (v/v/v) TFA/triethylsilane/water. Volatiles were removed under nitrogen flow. 51b was used for the synthesis of 52 without farther purification.

MS: $[M+3H]^{4+}=1064.3$, $[M+2H]^{3+}=1418.3$ (MW calculated=4254 g/mol)

Synthesis of 52

Raw material 51b was dissolved in 500 µl 1/1 (v/v) acetonitrile/0.25 M sodium phosphate pH 7 and 8 mg N,N'-bis(3-maleimidopropionyl)-2-hydroxy-1,3-propanediamine were added. The solution was stirred at RT for 15 min and 52 was purified by RP-HPLC and lyophilized.

52: Yield: 5.1 mg
MS $[M+3H]^{4+}=1162.8$, $[M+2H]^{3+}=1549.4$ (MW calculated=4645 g/mol)

Synthesis of Compound 53a

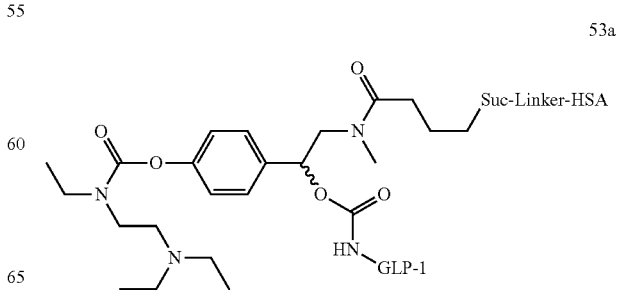

53a

30 µl 1.57 mM 48 (47 nmol) in 10 mM HEPES buffer pH 7.4, 150 mM NaCl, 3 mM EDTA, and 0.005% Tween were mixed with 10 µl 0.5 M sodium phosphate buffer pH 7.4. A mixture of 2 µl DMSO and 12 µl of 6.06 mM 51a (73 nmol) in water/acetonitrile 9/1 (v/v) was added and the solution was incubated at RT for 30 min. 53a was purified by SEC (column: Superdex 200, flow rate: 0.75 ml/min) using 10 mM phosphate buffer pH 7.4, 150 mM NaCl, and 0.005% Tween as mobile phase.

SEC retention time: 17.7 min (280 nm)

ESI-MS=70745 (MW calculated=70734 g/mol)

Synthesis of 53b

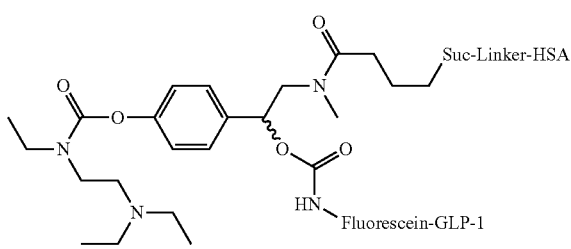

100 µl 3 mM 52 (300 nmol) in 9/1 50 mM sodium phosphate pH 7.0/acetonitrile were mixed with 100 µl 3 mM HSA (300 nmol) and the solution was incubated at RT for 30 min. 53b was purified by SEC (column: Superdex 200, flow rate: 0.75 ml/min) using 10 mM HEPES buffer pH 7.4, 150 mM NaCl, 3 mM EDTA, and 0.005% Tween as mobile phase.

SEC retention time: 17.7 min (500 nm)

Synthesis of Compounds 54a and 54b

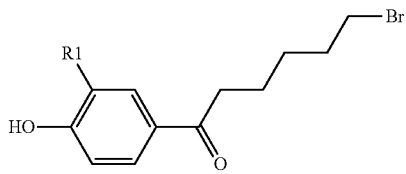

54a R1=Me
54b R1=H

AlCl$_3$ (1.05 eq) was suspended in DCM and 6-bromohexanoic acid chloride (1 eq) was added. After stirring at RT for 20 min o-cresol (1 eq) was added and the mixture was reacted at RT for 25 min. The reaction mixture was poured into ice water and extracted with ethyl acetate. The separated organic phase was dried over Na$_2$SO$_4$ and concentrated in vacuo. Product 54a was purified by silica gel column chromatography using heptane/ethyl acetate (4/1) as mobile phase.

54b was synthesized as described above using 6-bromohexanoic acid chloride and phenol.

54a: Yield 3.7 g (33%)

MS [M+H]$^+$=285.1 and 287.2 (MW+H calculated=386.2 g/mol)

54b: Yield 620 mg (15%)

MS [M+H]$^+$=271.2 (MW calculated=271.0 g/mol)

Synthesis of Compounds 55a and 55b

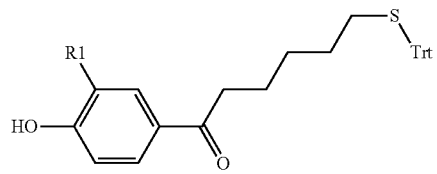

55a R1=Me
55b R1=H

DBU (105 µl, 701 µmol) was added to a solution of bromide 54a (105 mg, 369 µmol) and tritylthiol (204 mg, 738 µmol) in 50 ml dry DMSO. The reaction mixture was stirred at RT for 40 min and acidified with 1 N H$_2$SO$_4$. The aqueous layer was extracted with ethyl acetate and evaporated. 55a was purified by RP-HPLC, 55b was synthesized according to the same protocol using 54b (180 mg, 0.66 mmol).

55a: Yield 173 mg (97%)

MS [M+Na]$^+$=503.6 (MW+Na calculated=503.7 g/mol)

55b: Yield 160 mg (85%)

MS [M+Na]$^+$=489.5 (MW+Na calculated=489.3 g/mol)

Synthesis of Compounds 56a and 56b

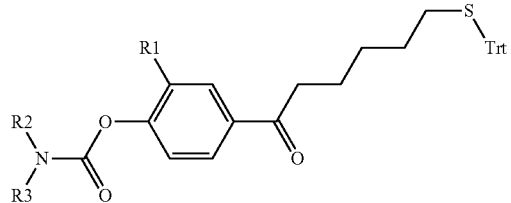

56a R1=Me, R2=R3=3-(dimethylamino)propyl,
56b R1=H, R2=Me, R3=3-(N-ethyl-N-methylamino)propyl 56a was prepared from 55a (9 mg, 19 µmol), p-nitrophenyl-chloroformate and bis(3-dimethylamino-propyl)amine (21 µl, 94 µmol) as described for compound 16a.

56b was synthesized from 55b (160 mg, 0.34 mmol), p-nitrophenyl-chloroformate and N-ethyl-N,N' dimethyl-1,3-propanediamine (15c) as described for compound 16a.

56a: yield 12 mg (70%) as TFA salt

MS [M+Na]$^+$=716.8 (MW+Na calculated=717.0 g/mol)

56b: Yield 80 mg (32%) as TFA salt

MS [M+Na]$^+$=645.6 (MW+Na calculated=645.4 g/mol)

Synthesis of Compounds 57a and 57b

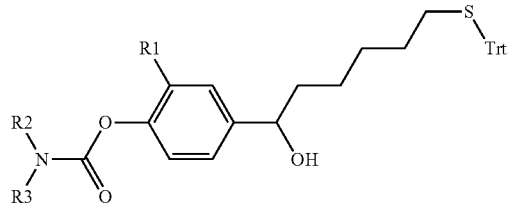

57a R1=Me, R2=R3=3-dimethylamino-propyl,
57b R1=H, R2=Me, R3=3-(N-ethyl-N-methylamino)propyl 57a and 57b were synthesized from 56a (12 mg, 13 µmol, double TFA salt) and 56b (80 mg, 110 µmol, TFA salt), respectively, as described for compound 16g.

57a: Yield 9 mg (75%) as TFA salt
MS [M+Na]$^+$=719.0 (MW+Na calculated=718.7 g/mol)
57b: Yield 60 mg (75%) as TFA salt
MS [M+Na]$^+$=647.4 (MW+Na calculated=647.4 g/mol)

Synthesis of Compounds 58a and 58b

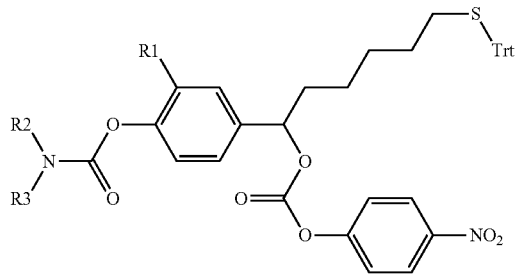

58a R1=Me, R2=R3=3-(dimethylamino)propyl,
58b R1=H, R2=Me, R3=3-N-ethyl-N-methylamino)propyl 57a (1 eq, 8 mg, 9 μmol), 4-nitrophenyl chloroformate (3.5 eq, 6 mg, 30 μmol), DIEA (6 eq, 9 μl, 52 μmol), and DMAP (1 eq, 1 mg, 9 μmol) were stirred in 1 ml dry DCM at RT for 45 min under nitrogen atmosphere. The volatiles were evaporated and acetic acid was added. The mixture was dissolved in 1/1 (v/v) acetonitrile/water and the carbonate 58a was purified by RP-HPLC.

Carbonate 58b was prepared likewise from 57b (135 mg, 0.18 mmol).

58a: Yield 7 mg (70%) as TFA salt
MS [M+Na]$^+$=883.8 (MW+Na calculated=884.1 g/mol)
58b: Yield 110 mg (77%) as TFA salt
MS [M+Na]$^+$=812.4 (MW+Na calculated=812.5 g/mol)

Synthesis of Compound 59

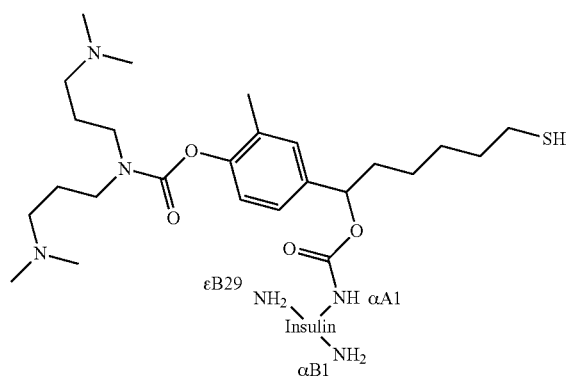

is Rh-Insulin (44.5 mg, 7.7 μmol), carbonate 58a (1 eq, 7 mg, 6.4 mmol), DIEA (15 μl, 88 μmol) and DMAP (1.5 mg, 12 μmol) in 0.3 ml DMSO were reacted at RT for 30 min. The reaction mixture was neutralized with acetic acid and diluted with 1/1 (v/v) acetonitrile/water. RP-HPLC purification gave the appropriate Trt-protected intermediate.

After lyophilization, the Trt-protected intermediate was mixed with 95/5 (v/v) TFA/triethylsilane and stirred for 5 min. Volatiles were removed under nitrogen flow and 59 was purified by RP-HPLC and lyophilized. Position of insulin modification was verified by DTT reduction and MS analysis.

59: MS [M+3H]$^{3+}$=2095.5 [M+4H]$^{4+}$=1572.2 (MW calculated=6288 g/mol)

Synthesis of Compound 60

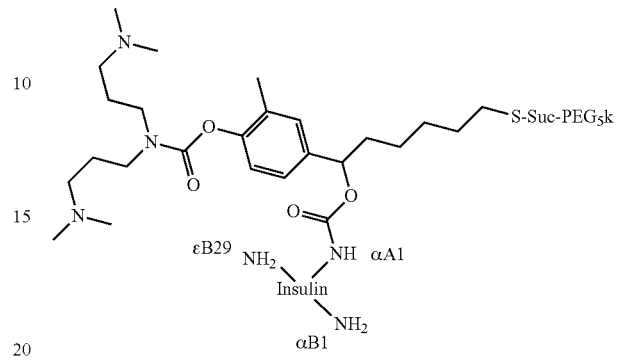

60 was prepared from 59 (0.17 μmol) as described for compound 9a.

60: SEC retention time: 19.5 min

Synthesis of Compound 61

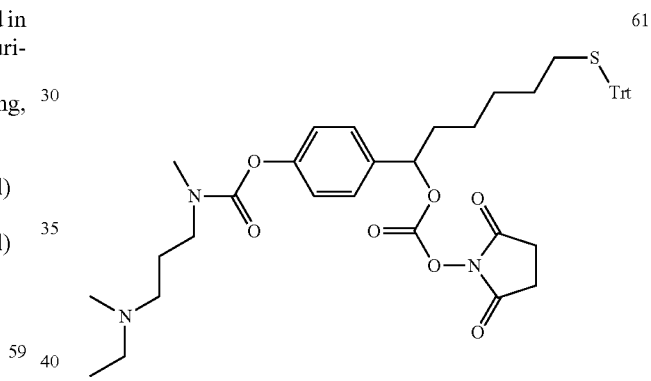

57b (70 mg, 90 μmol), DSC (161 mg, 630 μmol), DIEA (192 μl, 1.1 mmol), and DMAP (11 mg, 90 μmol) were stirred in 1 ml dry acetonitril at RT for 14 h under nitrogen atmosphere. The volatiles were evaporated and acetic acid was added. The mixture was dissolved in 1/1 (v/v) acetonitrile/water and the carbonate 61 was purified by RP-HPLC.

61: Yield 40 mg (51%) as TFA salt
MS [M+Na]$^+$=788.4 (MW+Na calculated=788.5 g/mol)

Synthesis of Compound 62

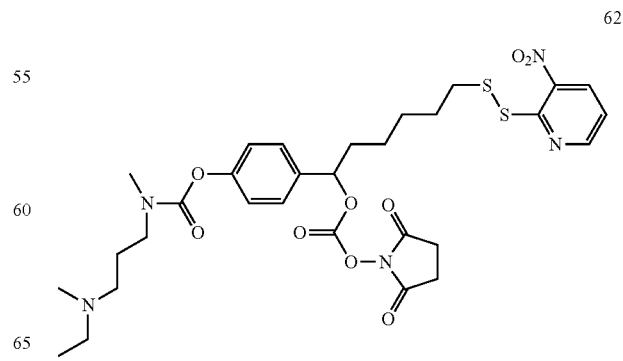

61 (12 mg, 13 μmol) and NPys-Cl (4 mg, 21 μmol) were stirred in 1 ml DCM at −10° C. for 2 h under nitrogen atmosphere. Volatiles were removed under nitrogen flow and 62 was purified by RP-HPLC.

62: Yield 7 mg (65%) as salt

MS [M+Na]$^+$=700.9 (MW+Na calculated=701.4 g/mol)

Synthesis of Compound 63

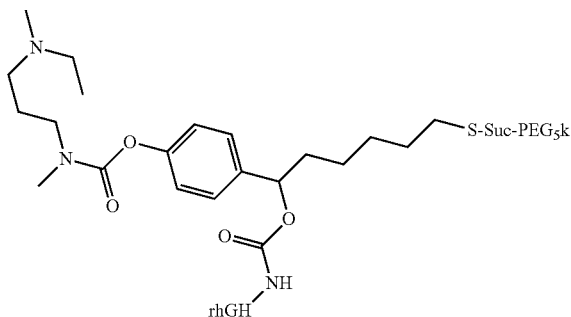

0.9 mg desalted rhGH (ProspecTany, Israel, MW 22250 g/mol, 40 nmol) in 200 μl 50 mM borate buffer (pH 8.0), 8 μl of carbonate 62 in acetonitrile (38 mM, 300 nmol), and 40 μl DMSO were reacted at RT for 3 h. The solvent mixture and low molecular weighed compounds were replaced by water and subsequently by acetate buffer (25 mM, pH 4.2, 0.005% Tween 20) by ultrafiltration using Centricon 5 filter (cutoff 5 kDa). 8 μl (80 nmol) 10 mM DTT in 25 mM acetate buffer pH 4.2, 0.005% Tween was added and incubated at RT for 30 min. Low molecular weight compounds were removed by ultrafiltration using Centricon 5 filter and 25 mM acetate buffer pH 4.2, 0.005% Tween as eluate. After concentration to a volume of 100 μl (Centricon 5) 20 μl (100 nmol) 5 mM maleimide-PEG5k in water and 80 μl 0.5 M phosphate buffer pH 7.0 were added. The mixture was incubated at RT for 5 min. Monoconjugate 63 was separated by SEC (column: Superdex 200, flow rate: 0.75 ml/min) using 10 mM phosphate buffer pH 7.4, 150 mM NaCl, and 0.005% Tween 20 as mobile phase. The collected eluate (approximately 1.0 ml) was diluted with 0.5 ml buffer containing 0.05% NaN$_3$ and directly used for release rate determination.

63: SEC retention time: 17.5 min

Release of Insulin or Fluorescein-insulin from Conjugates in Buffer pH 7.4

Release of (fluorescein)-insulin from (fluorescein)-insulin conjugates 9a to 9h, 21a to 21f, 30a, 30b, 43, 50, and 60, release of fluorescein-GLP-1 from 53b, and release of rhGH from 63 was effected by linker hydrolysis in aqueous buffer pH 7.4. Collected SEC eluates of (fluorescein)-insulin conjugates (see above), fluorescein-GLP-1 conjugate and rhGH-conjugate, respectively, were incubated at 37° C. and samples were taken at time intervals and analyzed by RP-HPLC (insulin conjugates) or SEC (rhGH conjugate, fluorescein insulin conjugates and fluorescein-GLP-1 conjugate) and UV detection at 215 or 280 nm or VIS detection at 500 nm. Peaks correlating with the retention time of native insulin, fluorescein-insulin, fluorescein-GLP-1, and rhGH, respectively, were integrated and plotted against incubation time, and curve-fitting software was applied to estimate the corresponding halftime of release.

Release of Insulin from Hydrogel Conjugates 45 and 46

4 mg of 45 or 2 mg 46 were weighed into a test tube and incubated with 1 ml 10 mM HEPES buffer pH 7.4, 150 mM NaCl, 0.005% Tween at 37° C. 45 μl samples were taken at different time intervals and quantitatively analyzed for rh-insulin by a RP-HPLC assay. The rh-insulin peaks were integrated and rh-insulin concentration was obtained from a standard curve. A first order release kinetic was fitted to the data points to give the linker half life.

MS-analysis of Released Insulin from Compound 9a, 9b and 30a

Figure 11:
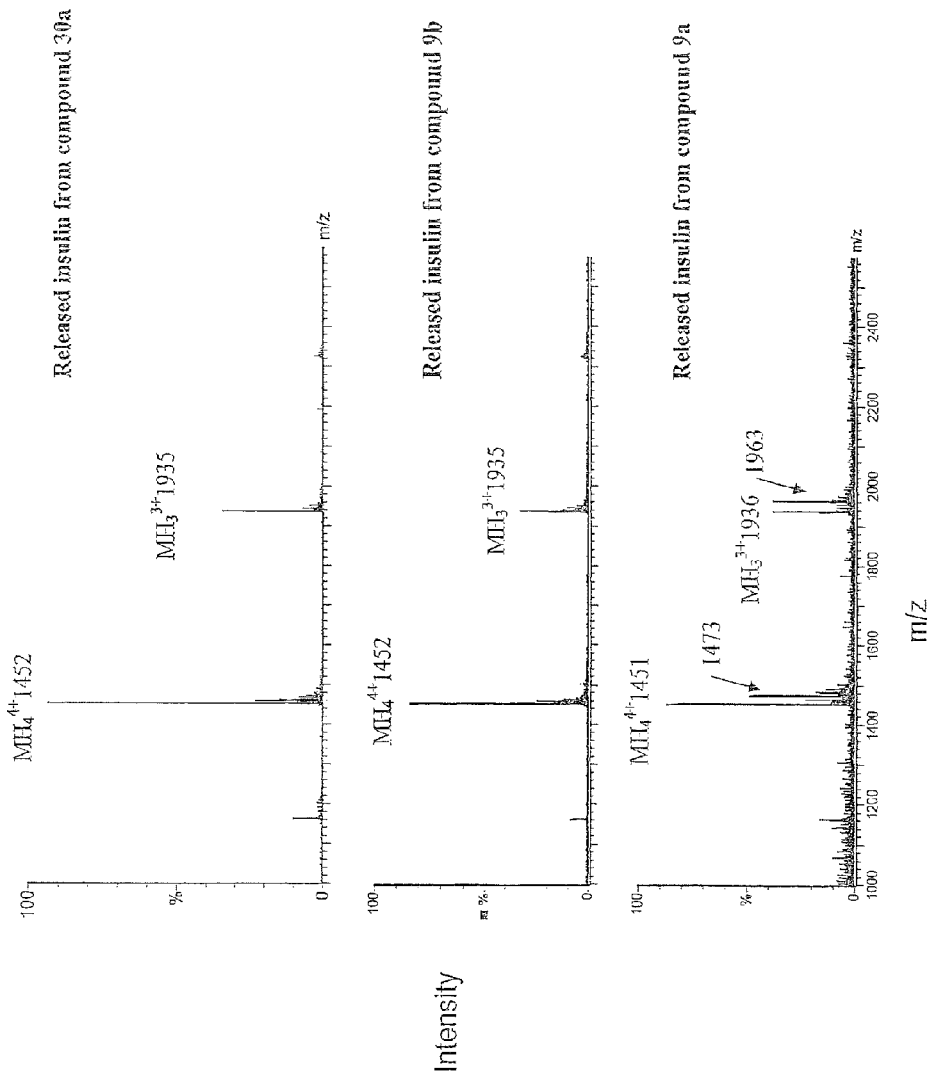
FIG. 11 shows mass spectra of prodrug released insulin molecules.

Samples of buffer released insulin (see above) were analyzed by mass spectrometry. FIG. 11 shows the mass spectra of released insulin from compound 9a, 9b, and 30a. The mass spectrum of insulin released from compound 9a clearly shows a major side product (indicated by arrows), corresponding to the irreversibly pentanoyl-modified insulin. In this case, removal of the pentanoyl masking group was not by hydrolysis but by acyl transfer to the insulin. The mass spectrum of insulin released from compound 9b and 30a shows no modification.

Release of Fluorescein-insulin from Conjugate 9d and 9e in 80% Human Plasma

Release of fluorescein-insulin from 9d or 9e was effected by hydrolysis in 80% human plasma in 20 mM HEPES pH 7.4 at 37° C. Samples were taken at time intervals and analyzed by SEC and VIS detection at 500 nm. Peaks correlating with the retention time of fluorescein-insulin were integrated and plotted against incubation time, and curve-fitting software was applied to estimate the corresponding halftime of release.

TABLE

Polymeric prodrug hydrolysis

| compound | $t_{1/2}$ buffer pH 7.4 | $t_{1/2}$ human plasma |
|---|---|---|
| 9a | 40 h | nd |
| 9b | 55 h | nd |
| 9c | 4.5 d | nd |
| 9d | 7 h | 4 h |
| 9e | 55 h | 30 h |
| 9f | 90 h | nd |
| 9g | 37 h | nd |
| 9h | 88 h | nd |
| 21a | 64 d | nd |
| 21b | 8 d | nd |
| 21c | 52 d | nd |
| 21d | 29 d | nd |
| 21e | 100 d | nd |
| 21f | 83 h | nd |
| 30a | 17 d | nd |
| 30b | >70 d | nd |
| 43 | 4 h | nd |
| 45 | 7 d | nd |
| 46 | 4 d | nd |
| 50 | 57 h | nd |
| 53b | 19 h | nd |
| 60 | 10 d | nd |
| 63 | 51 d | nd | nd = not determined

The foregoing is considered illustrative of the principles of the invention and since numerous modifications will occur to those skilled in the art, it is not intended to limit the invention to the exact construction and operation described. All suitable modifications and equivalents fall within the scope of the claims.

Abbreviations

Boc t-butyloxycarbonyl

DBU 1,3-diazabicyclo [5.4.0]undecene

DCM dichloromethane (iv)Dde 1-(4,4-dimethyl-2,6-dioxo-cyclohexyliden)3-methyl-butyl DIC diisopropylcarbodiimide DIEA diisopropylethylamine
DMAP dimethylamino-pyridine
DMF N,N-dimethylformamide
DMSO dimethylsulfoxide
Dpr diaminopropionic acid
DSC disuccinidylcarbonate
EDTA ethylenediaminetetraacetic acid
Et ethyl
eq stoichiometric equivalent
fmoc 9-fluorenylmethoxycarbonyl
Fmoc-Ado-OH Fmoc-8-amino-3,6-dioxaoctanoic acid
HFIP hexafluoroisopropanol
HEPES N-(2-hydroxyethyl)piperazine-N'-(2-ethanesulfonic acid)
HOBt N-hydroxybenzotriazole
LCMS mass spectrometry-coupled liquid chromatography
Mal maleimidopropionyl
Me methyl
Mmt 4-methoxytrityl
MS mass spectrum
MW molecular mass
Npys 3-nitro-2-pyridinesulfenyl
PyBOP benzotriazole-1-yl-oxy-tris-pyrrolidino-phosphonium hexafluorophosphate
rHSA recombinant human serum albumin
rhGH recombinant human growth hormone
RP-HPLC reversed-phase high performance liquid chromatography
RT room temperature
SEC size exclusion chromatography
Suc succinimidopropionyl
TES triethylsilane
TFA trifluoroacetic acid
THF tetrahydrofurane
UV ultraviolet
VIS visual
Z benzyloxycarbonyl

The invention claimed is:

1. A polymeric cascade prodrug wherein the prodrug corresponds to a structure selected from the general formula I and II:

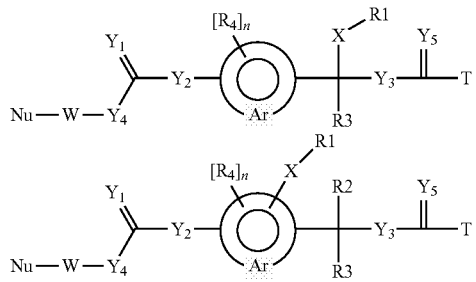

wherein X represents a spacer moiety; T represents a somatropin moiety; $Y_1$ and $Y_2$ each independently represent O, S or $NR_6$; $Y_3$ and $Y_5$ independently represent O or S; $Y_4$ represents O, $NR_6$ or —$C(R_7)(R_8)$; R2 and R3 represent a moiety selected from the group consisting of hydrogen, substituted or unsubstituted linear, branched or cyclical alkyl or heteroalkyl groups, aryls, substituted aryls, substituted or unsubstituted heteroaryls, cyano groups, nitro groups, halogens, carboxy groups, carboxyalkyl groups, alkylcarbonyl groups or carboxamidoalkyl groups; $R_4$ represents a moiety selected from the group consisting of hydrogen, substituted or unsubstituted linear, branched or cyclical alkyls or heteroalkyls, aryls, substituted aryls, substituted or unsubstituted heteroaryl, substituted or unsubstituted linear, branched or cyclical alkoxys, substituted or unsubstituted linear, branched or cyclical heteroalkyloxys, aryloxys or heteroaryloxys, cyano groups and halogens; $R_7$ and $R_8$ are each independently selected from the group consisting of hydrogen, substituted or unsubstituted linear, branched or cyclical alkyls or heteroalkyls, aryls, substituted aryls, substituted or unsubstituted heteroaryls, carboxyalkyl groups, alkylcarbonyl groups, carboxamidoalkyl groups, cyano groups, and halogens; $R_6$ represents a group selected from hydrogen, substituted or unsubstituted linear, branched or cyclical alkyls or heteroalkyls, aryls, substituted aryls and substituted or unsubstituted heteroaryls; $R_1$ represents a polymer; W represents a group selected from substituted or unsubstituted linear, branched or cyclical alkyls, aryls, substituted aryls, substituted or unsubstituted linear, branched or cyclical heteroalkyls, substituted or unsubstituted heteroaryls; Nu represents a nucleophile; n represents zero or a positive integer; and Ar represents a multi-substituted aromatic hydrocarbon or multi-substituted aromatic heterocycle.

2. The prodrug according to claim 1, wherein the somatropin is prepared by recombinant DNA technology.

3. The polymeric cascade prodrug according to claim 1, wherein each R4 independently represents a substituent selected from the group consisting of hydrogen, methyl, ethyl, ethoxy, methoxy, linear alkyls having three or more carbon atoms, cycloalkyls, branched alkyls and $C_{1-6}$ heteroalkyls.

4. The polymeric cascade prodrug according to claim 1, wherein R1 represents a polymer selected from the group consisting of polyalkyloxy polymers, dextran, chitosan, hyaluronic acid and derivatives thereof, alginate, xylan, mannan, carrageenan, agarose, cellulose, starch, hydroxyethyl starch, carbohydrate-based polymers, polyvinyl alcohols, polyoxazolines, polyanhydrides, poly(ortho esters), polycarbonates, polyurethanes, polyacrylic acids, polyacrylamides, polyacrylates, polymethacrylates, polyorganophosphazenes, polysiloxanes, polyvinylpyrrolidone, polycyanoacrylates, polyesters, polyiminocarbonates, polyaminoacids, collagen, gelatin, copolymers, grafted copolymers, cross-linked polymers, and block copolymers thereof.

5. The polymeric cascade prodrug according to claim 1, wherein R1 represents a hydrogel.

6. The polymeric cascade prodrug according to claim 1, wherein R1 represents a branched or hyperbranched polymer.

7. The polymeric cascade prodrug according to claim 1, wherein R1 represents a dendrimer or dense star polymer.

8. The polymeric cascade prodrug according to claim 1, wherein R1 represents a biopolymer.

9. The polymeric cascade prodrug according to claim 1, wherein R1 represents a protein.

10. The polymeric cascade prodrug according to claim 9, wherein the protein is selected from the group consisting of albumin, antibodies, fibrin, casein and plasma proteins.

11. The polymeric cascade prodrug according to claim 1, wherein R1 further includes one or more biologically active substances bound to the polymer.

12. The polymeric cascade prodrug according to claim 1, wherein R1 has at least one functional group for linkage to X, and wherein the at least one functional group is selected from the group consisting of carboxylic acid and activated derivatives thereof, amino groups, maleimide, thiol, sulfonic acid and derivatives thereof, carbonate and derivatives thereof, carbamate and derivatives thereof, hydroxyl, aldehyde, ketone, hydrazine, isocyanate, isothiocyanate, phosphoric acids and derivatives thereof, phosphonic acids and derivatives thereof, haloacetyls, alkyl halides, acryloyls, arylating agents, hydroxylamines, disulfides, vinyl sulfones, vinyl ketones, diazoalkanes, diazoacetyl compounds, epoxide, oxirane, and aziridine.

13. The polymeric cascade prodrug according to claim 12, wherein the at least one functional group is selected from the group consisting of thiol, maleimide, amino groups, carboxylic acid and derivatives thereof, carbonate and derivatives thereof, carbamate and derivatives thereof, aldehyde, and haloacetyls.

14. The polymeric cascade prodrug according to claim 12, wherein the bond formed between X and the at least one functional group is selected from the group consisting of disulfide, S-succinimido, amide, amino, carboxylic ester, sulphonamide, carbamate, carbonate, oxime, hydrazone, urea, thiourea, phosphate, and phosphonate.

15. The polymeric cascade prodrug according to claim 12, wherein the bond formed between X and the at least one functional group is selected from the group consisting of S-succinimido, amide, carbamate, and urea.

16. The polymeric cascade prodrug according to claim 1, wherein

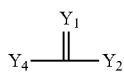

represents a moiety selected from the group consisting of

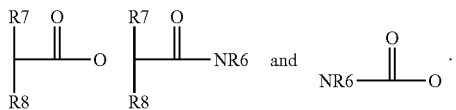

17. The polymeric cascade prodrug according to claim 1, wherein

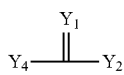

represents a moiety selected from the group consisting of

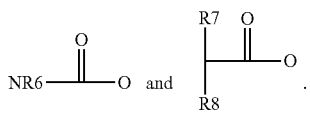

18. The polymeric cascade prodrug according to claim 1, wherein R6 represents an additional Nu-W.

19. The polymeric cascade prodrug according to claim 1, wherein

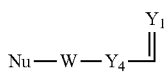

represents a structure selected from the group consisting of

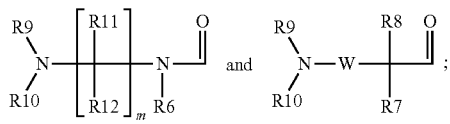

wherein R9, R10, R11 and R12 each independently represent a moiety selected from the group consisting of hydrogen, substituted or non-substituted alkyls or heteroalkyls, and substituted or non-substituted aryls or heteroaryls, and m represents an integer of 2 to 10.

20. The polymeric cascade prodrug or corresponding linker reagent according to claim 19, wherein R9, 10, R11 and R12 each independently represent a moiety selected from the group consisting of hydrogen and substituted or non-substituted alkyls.

21. The polymeric cascade prodrug according to claim 1, wherein Nu represents a nucleophile selected from the group consisting of primary, secondary and tertiary amino groups, thiols, carboxylic acids, hydroxylamines, hydrazine and nitrogen containing heteroaryls.

22. The polymeric cascade prodrug according to claim 1, wherein $Y_4$ represents —$C(R_7)(R_8)$ and at least one of R7 and R8 is not hydrogen.

23. The polymeric cascade prodrug according to claim 1, wherein Ar represents a structure selected from the group consisting of:

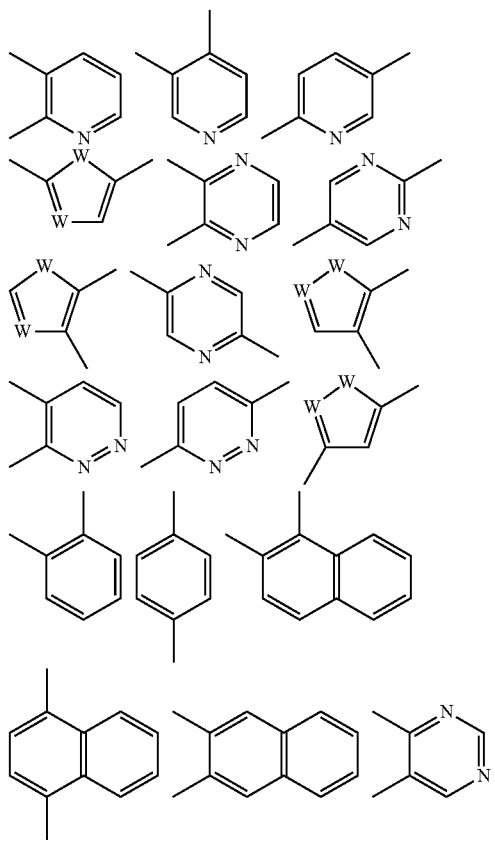

wherein each W independently represents O, S, or N.

24. The polymeric cascade prodrug according to claim 1, wherein Ar represents a monocyclic or dicyclic aromatic hydrocarbon or aromatic heterocycle.

25. The polymeric cascade prodrug according to claim 1, wherein the Ar represents a five-membered or six-membered aromatic hydrocarbon or aromatic heterocycle.

26. A method for synthesizing a polymeric prodrug, the method comprising:
(a) providing a starting molecule corresponding to the general Formula II or IIb:

(II)

(IIb)

(b) reacting the starting molecule with a masking group having a nucleophile to form at least one intermediate compound wherein the masking group is bound to $Y_2$; and
(c) reacting a somatropin moiety D with the at least one intermediate compound to form a polymeric prodrug;

wherein $Y_2$ is selected from O, S, or NR6; $Y_3$ is selected from O or S; X is a spacer moiety; R2 and R3 are selected independently from hydrogen, substituted or non-substituted linear, branched or cyclical alkyl or heteroalkyl, aryl, substituted aryl, substituted or non-substituted heteroaryl, cyano nitro, halogen, carboxy, carboxyalkyl, alkylcarbonyl or carboxamidoalkyl; R4 is selected from hydrogen, substituted or non-substituted linear, branched or cyclical alkyl or heteroalkyl, aryl, substituted aryl, substituted or non-substituted heteroaryl, substituted or non-substituted linear, branched, or cyclical alkoxy, substituted or non-substituted linear, branched, or cyclical heteroalkyloxy, aryloxy or heteroaryloxy, cyano, or halogen; R6 is selected from hydrogen, substituted or non-substituted linear, branched or cyclical alkyl or heteroalkyl, aryl, substituted aryl substituted or non-substituted heteroaryl; n is zero or a positive integer and Ar is a multi-substituted aromatic hydrocarbon or a multi-substituted aromatic heterocycle.

27. A method for hydrolyzing a polymeric cascade prodrug according to claim 1, comprising providing the prodrug and placing the prodrug in a solution with a pH of approximately 7.4.

28. A method of administering a somatropin moiety to an organism in need thereof, the method comprising providing a polymeric cascade prodrug according to claim 1, administering the polymeric cascade prodrug to the organism and cleaving the somatropin moiety from the polymeric cascade prodrug by means of a substantially non-enzymatic reaction.

* * * * *